(12) United States Patent
Benhar et al.

(10) Patent No.: US 10,822,428 B2
(45) Date of Patent: Nov. 3, 2020

(54) BI-AND MONOSPECIFIC, ASYMMETRIC ANTIBODIES AND METHODS OF GENERATING THE SAME

(71) Applicant: Ramot at Tel-Aviv University Ltd., Tel-Aviv (IL)

(72) Inventors: Itai Benhar, Rehovot (IL); Lilach Vaks, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 15/447,244

(22) Filed: Mar. 2, 2017

(65) Prior Publication Data

US 2017/0174791 A1    Jun. 22, 2017

Related U.S. Application Data

(63) Continuation of application No. 14/005,580, filed as application No. PCT/IL2012/050093 on Mar. 15, 2012, now Pat. No. 9,624,291.

(60) Provisional application No. 61/453,591, filed on Mar. 17, 2011.

(51) Int. Cl.
| | |
|---|---|
| *C07K 16/28* | (2006.01) |
| *C07K 16/46* | (2006.01) |
| *A61K 47/68* | (2017.01) |
| *C07K 16/32* | (2006.01) |
| *C07K 16/00* | (2006.01) |
| *A61K 39/00* | (2006.01) |

(52) U.S. Cl.
CPC ............ *C07K 16/468* (2013.01); *C07K 16/00* (2013.01); *C07K 16/2878* (2013.01); *C07K 16/32* (2013.01); *A61K 2039/507* (2013.01); *C07K 2317/31* (2013.01); *C07K 2317/522* (2013.01); *C07K 2317/526* (2013.01); *C07K 2317/55* (2013.01); *C07K 2317/56* (2013.01); *C07K 2317/60* (2013.01)

(58) Field of Classification Search
CPC .. C07K 16/468; C07K 16/2878; C07K 16/32; C07K 16/00; C07K 2317/522; C07K 2317/526; C07K 2317/55; C07K 2317/56; C07K 2317/31; C07K 2317/60; C07K 16/1275; A61K 2039/507; A61P 35/00; A61P 31/00; A61P 29/00
See application file for complete search history.

(56) References Cited

U.S. PATENT DOCUMENTS

| | | | |
|---|---|---|---|
| 5,747,654 A | 5/1998 | Pastan et al. | |
| 6,147,203 A | 11/2000 | Pastan et al. | |
| 6,558,672 B1 | 5/2003 | Pastan et al. | |
| 7,183,076 B2 | 2/2007 | Arathoon et al. | |
| 7,655,229 B2* | 2/2010 | Chan | C07K 16/283 424/136.1 |
| 7,919,257 B2 | 4/2011 | Hoogenboom et al. | |
| 2003/0078385 A1 | 4/2003 | Arathoon et al. | |
| 2008/0064025 A1* | 3/2008 | Su | G01N 33/542 435/5 |
| 2008/0125363 A1* | 5/2008 | Filpula | C07K 14/21 424/183.1 |
| 2009/0232811 A1 | 9/2009 | Klein et al. | |
| 2010/0081796 A1 | 4/2010 | Brinkmann et al. | |
| 2010/0226925 A1* | 9/2010 | Dillon | C07K 16/00 424/141.1 |
| 2010/0254986 A1 | 10/2010 | Carter et al. | |
| 2010/0256338 A1 | 10/2010 | Brinkmann et al. | |
| 2010/0256340 A1* | 10/2010 | Brinkmann | C07K 16/00 530/387.3 |
| 2014/0010814 A1 | 1/2014 | Benhar et al. | |

FOREIGN PATENT DOCUMENTS

| | | |
|---|---|---|
| EP | 0979281 | 2/2000 |
| WO | WO 94/29350 | 12/1994 |
| WO | WO 98/50431 | 11/1998 |
| WO | WO 2009/080253 | 7/2009 |
| WO | WO 2009/107129 | 9/2009 |
| WO | WO 2010/034441 | 4/2010 |
| WO | WO 2010/040508 | 4/2010 |
| WO | WO 2010/115553 | 10/2010 |
| WO | WO 2010/115589 | 10/2010 |
| WO | WO 2012/123949 | 9/2012 |

OTHER PUBLICATIONS

Cochran et al. J. Immunol. Meth. 287: 147-158 (Year: 2004).*
Stancovski et al., PNAS, 88: 8691-8695 (Year: 1991).*
Jiang et al. J. Biol. Chem. 280 (6): 4656-4662 (Year: 2005).*
Lloyd et al., Protein Engineering, Design & Selection 22:159-168 (Year: 2009).*
Edwards et al., J Mol Biol. 334(1): 103-118 (Year: 2003).*
Examiner's Response to Rule 312 Communication dated Jan. 23, 2017 From the US Patent and Trademark Office Re. U.S. Appl. No. 14/005,580.
Advisory Action Before the Filing of an Appeal Brief dated Jun. 2016 From the US Patent and Trademark Office Re. U.S. Appl. No. 14/005,580.

(Continued)

*Primary Examiner* — Phuong Huynh

(57) ABSTRACT

An antibody is provided. The antibody comprises an Fc region and a Fab region, wherein the Fab region comprises a first covalent link between a first heavy chain and a first light chain of the Fab region and a second covalent link between a second heavy chain and a second light chain of said Fab region, wherein a position of the first covalent link relative to the first heavy chain is different to a position of the second covalent link relative to the second heavy chain.

Methods of generating same and uses thereof are also provided.

11 Claims, 25 Drawing Sheets
(22 of 25 Drawing Sheet(s) Filed in Color)

Specification includes a Sequence Listing.

(56) References Cited

OTHER PUBLICATIONS

Communication Pursuant to Article 94(3) EPC dated Aug. 19, 2014 From the European Patent Office Re. Application No. 12716657.7.
International Search Report and the Written Opinion dated Jul. 5, 2012 From the International Searching Authority Re. Application No. PCT/IL2012/050093.
Notice of Allowance dated Nov. 23, 2016 From the US Patent and Trademark Office Re. U.S. Appl. No. 14/005,580. (8 pages).
Notification of Office Action dated Sep. 2, 2014 From the State Intellectual Property Office of the People's Republic of China Re. Application No. 201280013666.X and Its Translation Into English.
Office Action dated Jun. 1, 2016 From the Israel Patent Office Re. Application No. 228442.
Official Action dated Feb. 9, 2016 From the US Patent and Trademark Office Re. U.S. Appl. No. 14/005,580.
Official Action dated Jul. 30, 2015 From the US Patent and Trademark Office Re. U.S. Appl. No. 14/005,580.
Patent Examination Report dated Jun. 2, 2016 From the Australian Government, IP Australia Re. Application No. 2012227883.
Restriction Official Action dated Apr. 27, 2015 From the US Patent and Trademark Office Re. U.S. Appl. No. 14/005,580.
Search Report dated Sep. 2, 2014 From the State Intellectual Property Office of the People's Republic of China Re. Application No. 201280013666.X and Its Translation Into English.
Written Opinion dated Mar. 8, 2013 From the International Preliminary Examining Authority Re. Application No. PCT/IL2012/050093.
Written Opinion dated Aug. 26, 2013 From the International Preliminary Examining Authority Re. Application No. PCT/IL2012/050093.
Carter "Bispecific Human IgG by Design", Journal of Immunological Methods, XP002974199, 248(1-2): 7-15, Jan. 1, 2001.
Cochran et al. "Domain-Level Antibody Epitope Mapping Through Yeast Surface Display of Epidermal Growth Factor Receptor Fragments", Journal of Immunology, 287(1-2): 147-158, Apr. 2004.
Geisses et al. "Eukaryotic Expression Systems: A Comparison", Protein Expression and Purification 8:271-282,1996.
Glockshuber et al. "The Disulfide Bonds in Antibody Variable Domains: Effects on Stability, Folding in Vitro, and Functional Expression in *Escherichia Coli*", Biochemistry, 31(5): 1270-1278, 1992.
Gunasekaran et al. "Enhancing Antibody Fc Heterodimer Formation Through Electrostatic Steering Effects. Applications to Bispecific Molecules and Monovalent IgG", The Journal of Biological Chemistry, XP055001947, 285(25): 19637-19646, Jun. 18, 2010. Abstract.
Hakim et al. "'Inclonals': IgG Antibodies Produced in *E. Coli* in the Context of Targeted Anticancer Therapy", Abstracts of the 8th International Conference of Anticancer Research, Kos, Greece, Oct. 17-22, 2008, XP009120224, 28(5C): 3211-3212, #55, Oct. 22, 2008.
Hust et al. "Single Chain Fab (ScFab) Fragment", BMC Biotechnology, XP021023594, 7(14): 1-15, Mar. 8, 2007.
Jackman et al. "Development of a Two-Part Strategy to Identify a Therapeutic Human Bispecific Antibody That Inhibits IgE Receptor Signaling", The Journal of Biological Chemistry, 285(27): 20850-20859, Jul. 2, 2010.
Jiang et al. "A Novel Peptide Isolated From a Phage Display Peptide Library With Trastuzumab Can Mimic Antigen Epitope of HER-2", The Journal of Biological Chemistry, 280(6): 4656-4662, Feb. 11, 2005.
Kaufman "Overview of Vector Design for Mammalian Gene Expression", Molecular Biotechnology, 16: 151-160, 2000.
Kobayashi et al. "Similarities in the Biodistribution of Iodine-Labeled Anti-Tac Single-Chain Disulfide-Stabilized Fv Fragment and Anti-Tac Disulfide-Stabilized Fv Fragment", Nuclear Medicine and Biology, 25(4): 387-393, May 1998.
Makrides "Components of Vectors for Gene Transfer and Expression in Mammalian Cells", Protein Expression and Purification, 17: 183-202, 1999.
Mazor et al. "ChFRP5-ZZ-PE38, A Large IgG-Toxin Immunoconjugate Outperforms the Corresponding Smaller FRPS(Fv)-ETA Immunotoxin in Eradicating ErbB2-Expressing Tumor Xenografts", Cancer Letters, XP022276696, 257(1): 124-135, Sep. 27, 2007.
Merchant et al. "An Efficient Route to Human Bispecific IgG", Nature Biotechnology, XP002141015, 16(7): 677-681, Jul. 1, 1998.
Onda et al. "In Vitro and In Vivo Cytotoxic Activities of Recombinant Immunotoxin 8H9(Fv)-PE38 Against Breast Cancer, Osteosarcoma, and Neuroblastoma", Cancer Research, XP002348888, 64: 1419-1424, Feb. 15, 2004.
Rajagopal et al. "A Form of Anti-Tac (Fv) Which is Both Single-Chain and Disulfide Stabilized: Comparison With Its Single-Chain and Disulfide-Stabilized Homologs", Protein Engineering, 10(12): 1453-1459, 1997.
Roethlisberger et al. "Domain Interactions in Fab Fragment: A Comparative Evaluation of the Single-Chain Fv and Fab Format Engineered With Variable Domains of Different Stability", Journal of Molecular Biology, 347: 773-789, 2005.
Schaefer et al. "Immunoglobulin Domain Crossover as a Generic Approach for the Production of Bispecific IgG Antibodies", Proc. Natl. Acad. Sci. USA, PNAS, 108(27): 11187-11192, Jul. 5, 2011, Early Edition, Jun. 20, 2011.
Schmidt et al. "Suppression of Metastasis Formation by a Recombinant Single Chain Antibody-Toxin Targeted to Full-Length and Oncogenic Variant EGF Receptors", Oncogene, 18: 1711-1721, 1999.
Schmiedl et al. "Expression of a Bispecific DsFv-DsFv' Antibody Fragment in *Escherichia Coli*", Protein Engineering, XP002173476, 13(10): 725-734, Oct. 1, 2000. Abstract, Fig.7.
Segal et al. "Introduction: Bispecific Antibodies", Journal of Immunological Methods 248:1-6, 2001.
Werner et al. "Appropriate Mammalian Expression Systems for Biopharmaceuticals", Arzneimittelforschunq, 48(8): 2 Pages, Aug. 1998.
Yu et al. "Interaction Between Bevacizumab and Murine VEGF-A: A Reassessment", Investigative Ophthalmology & Visual Science, 49(2): 522-527, Feb. 2008.

\* cited by examiner

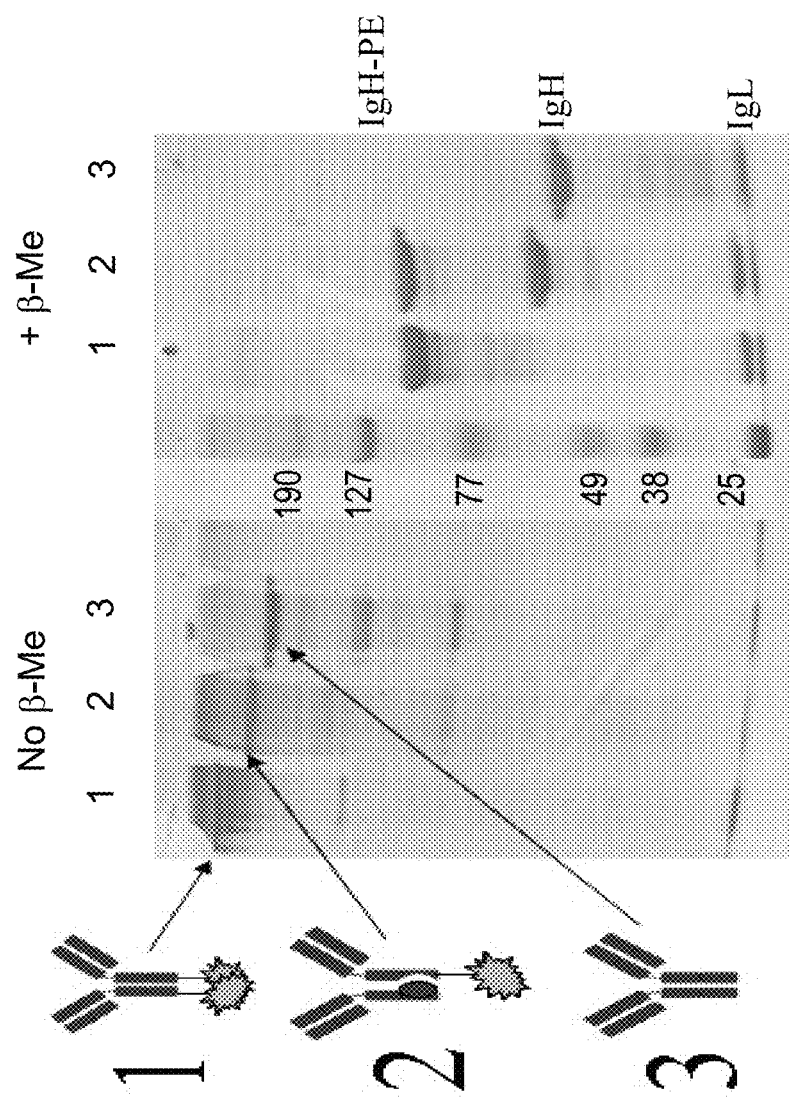
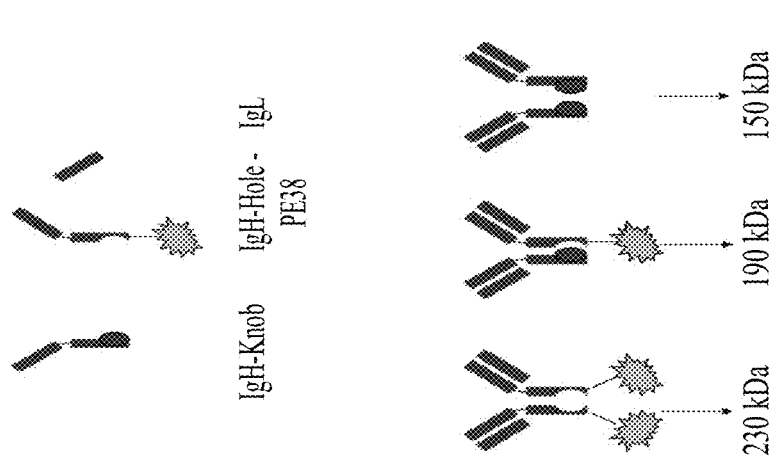

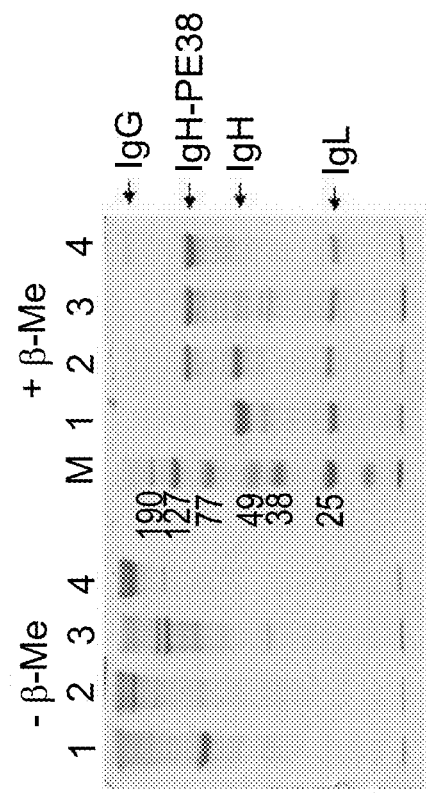

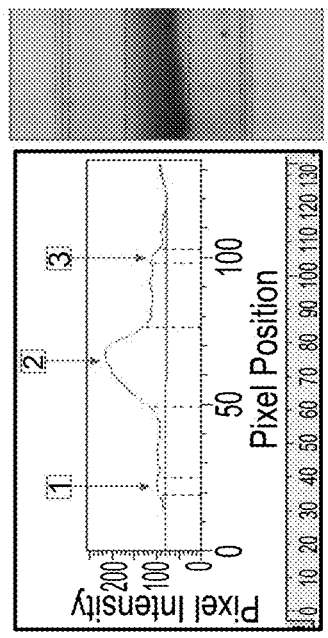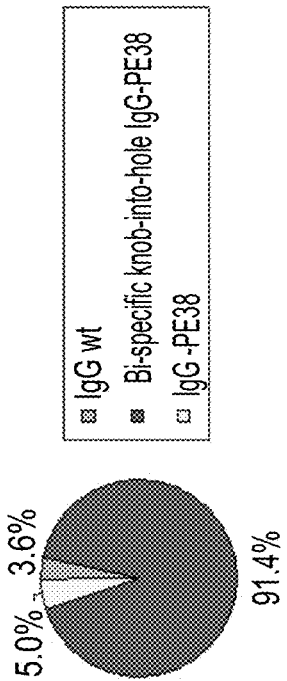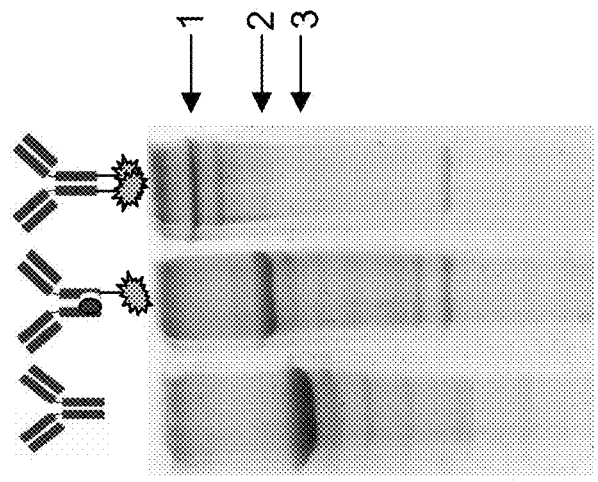

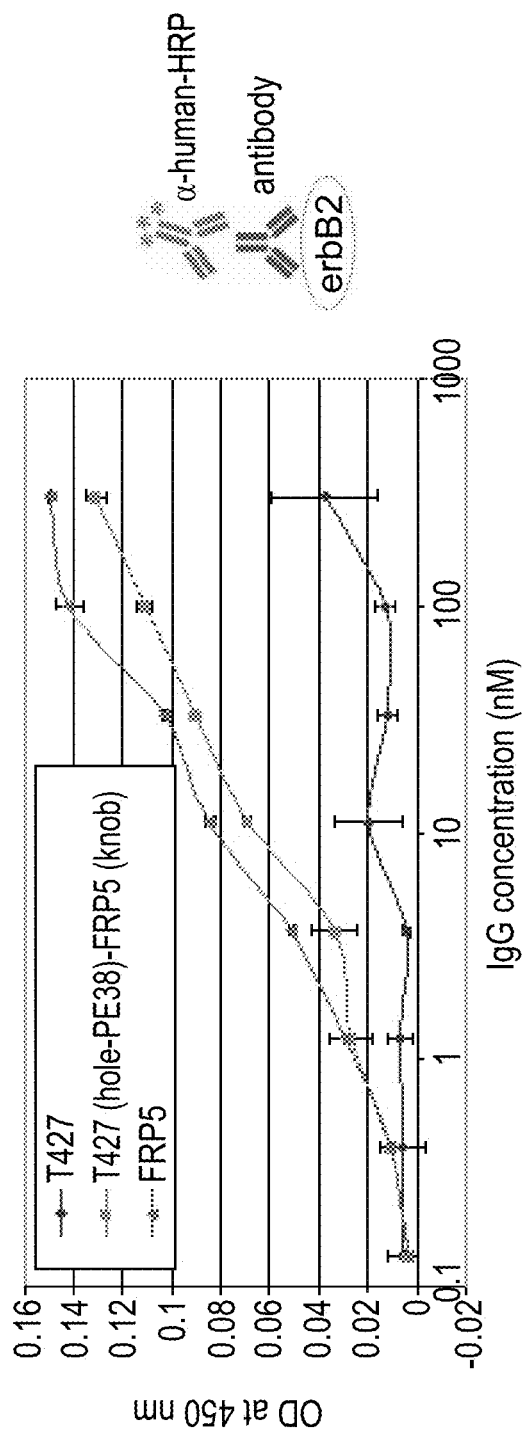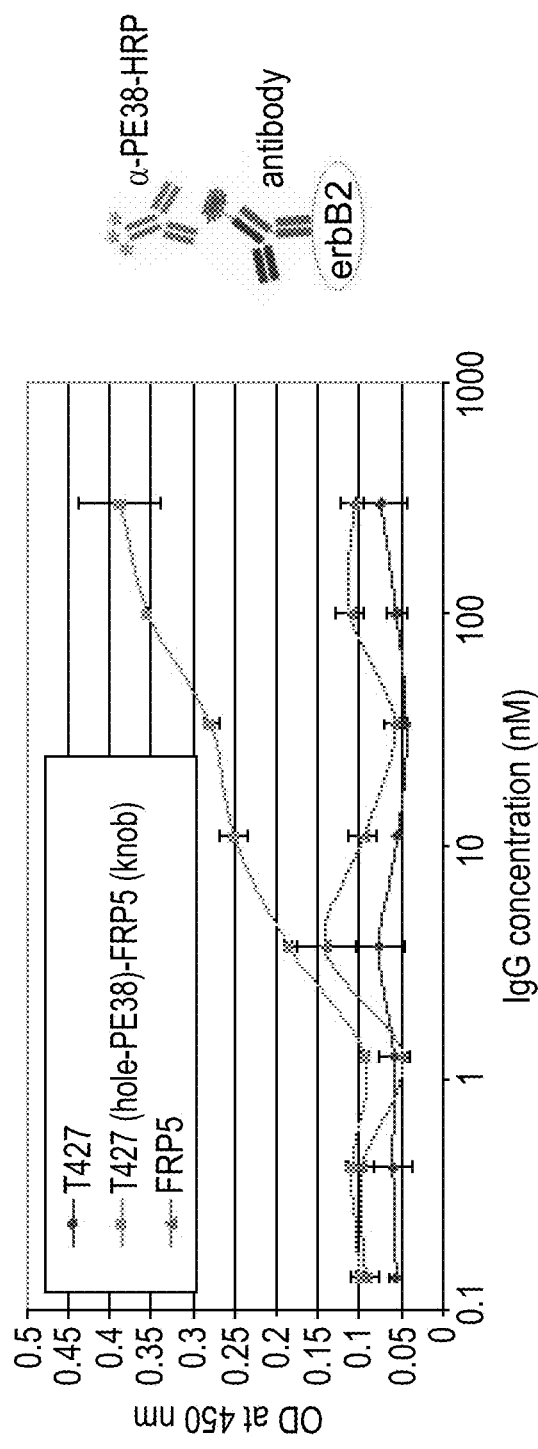
FIG. 8A
FIG. 8B

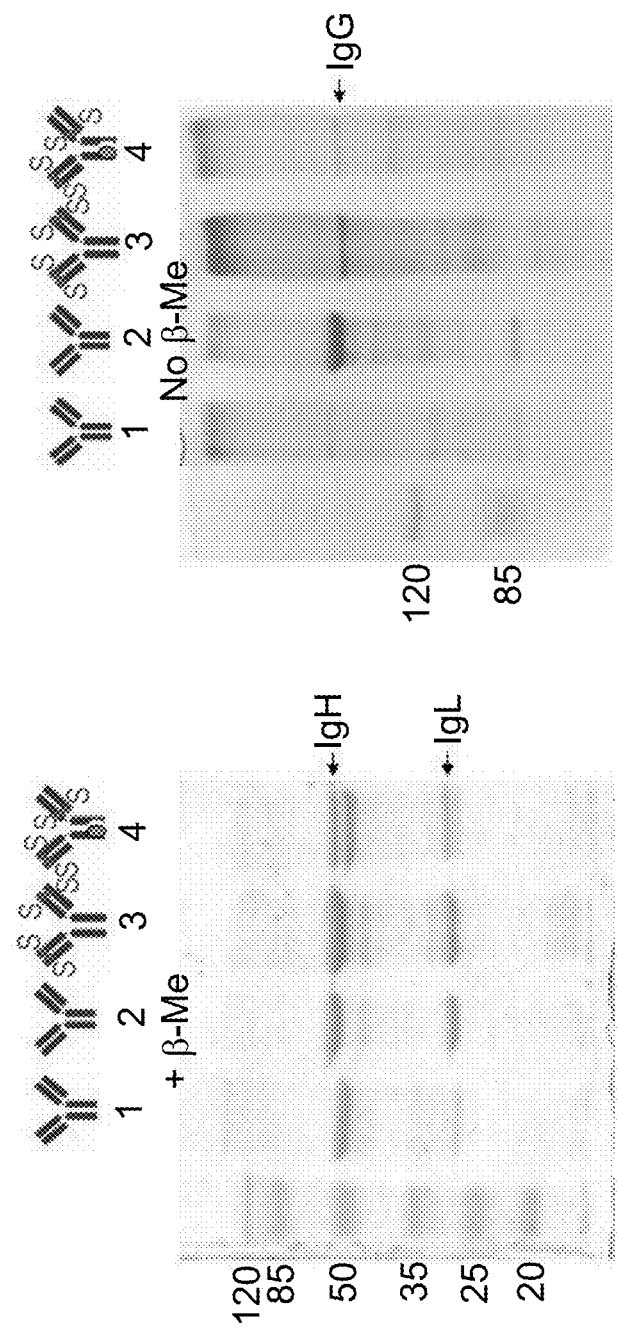

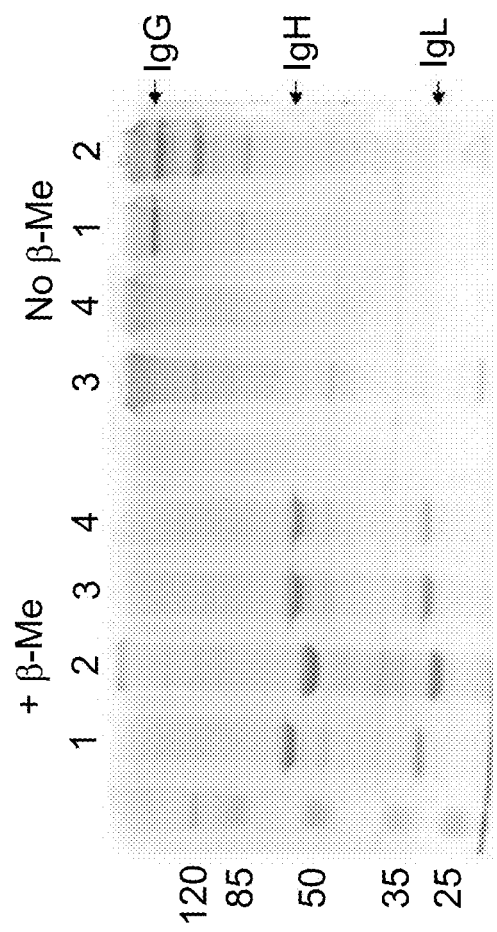

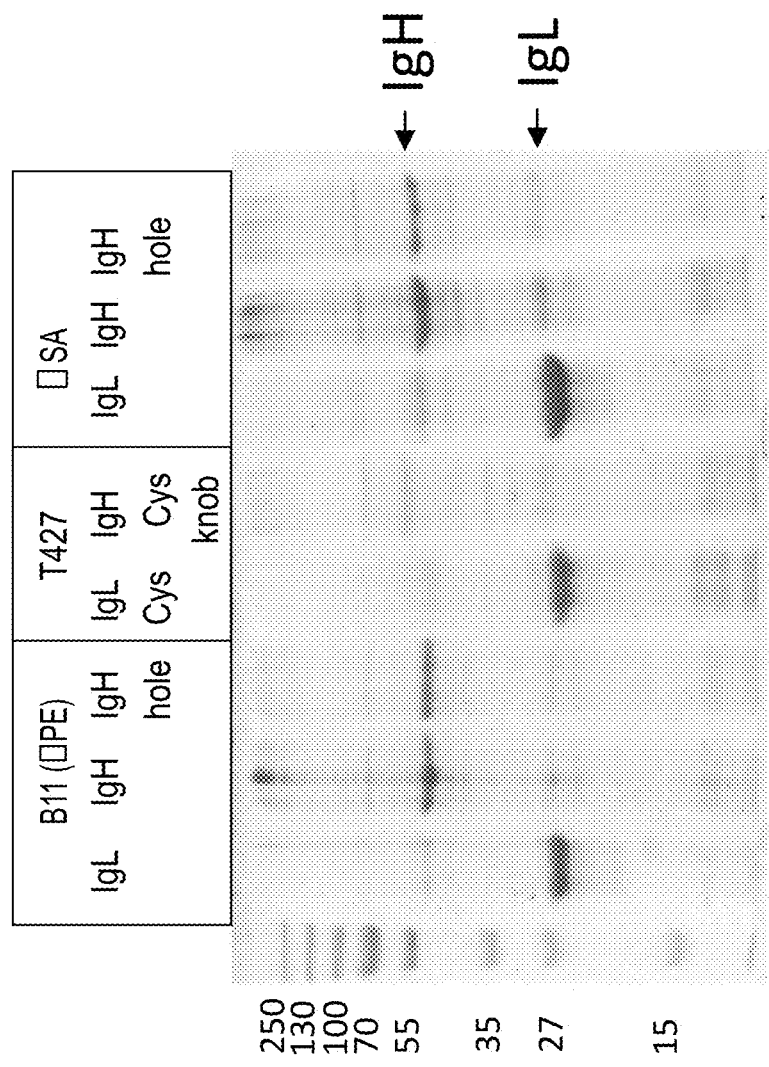

Binding to CD30-MBP

Binding to BSA

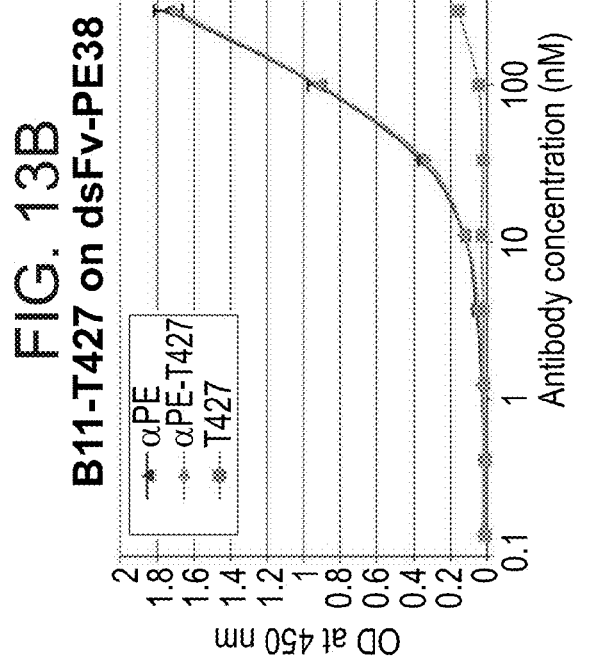
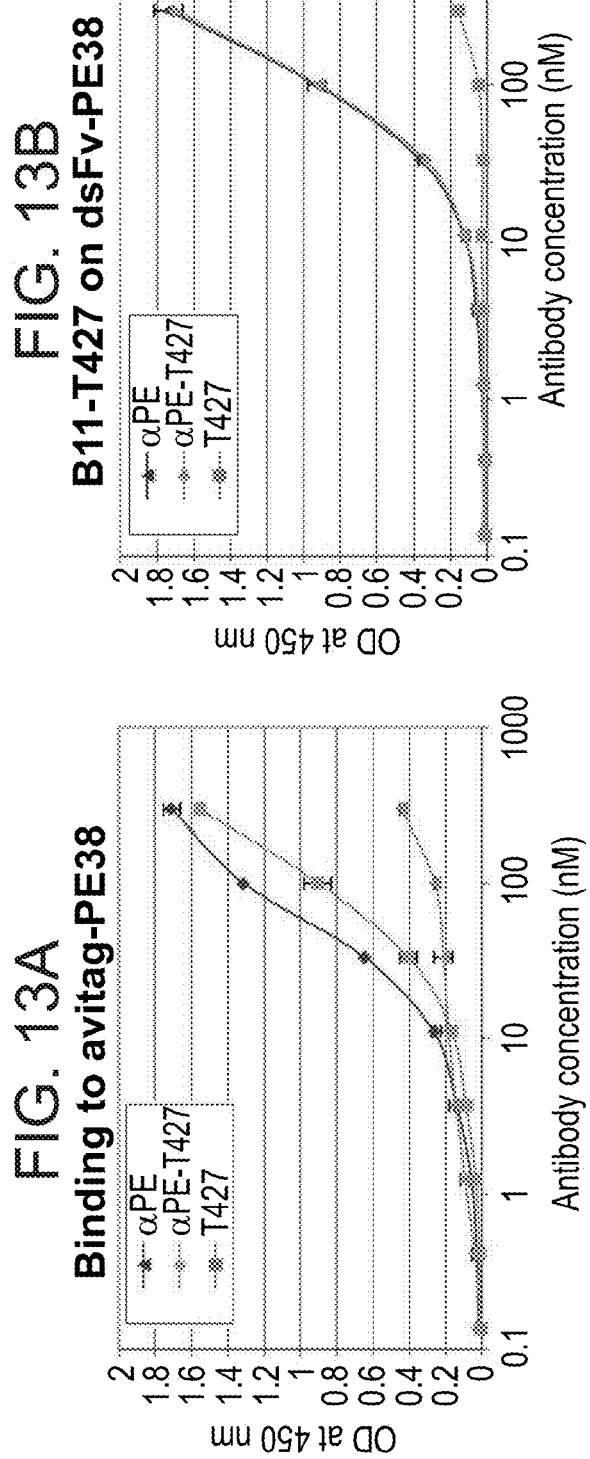
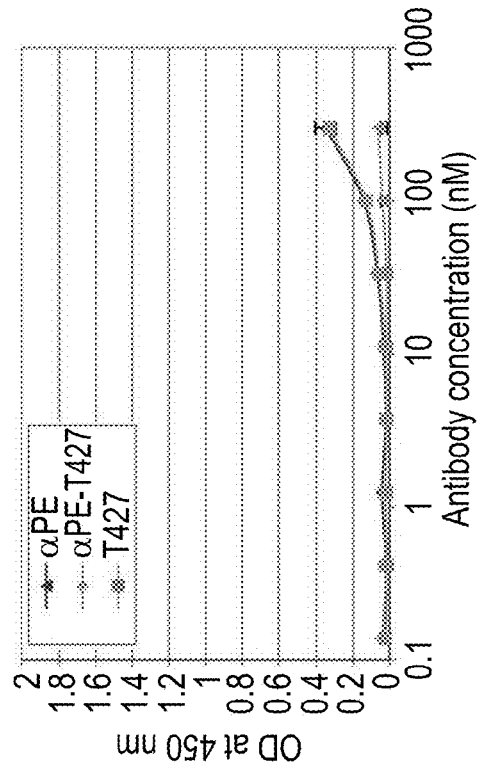

Binding ability to erbB2

Binding ability to CD30 antigen

FIG.24
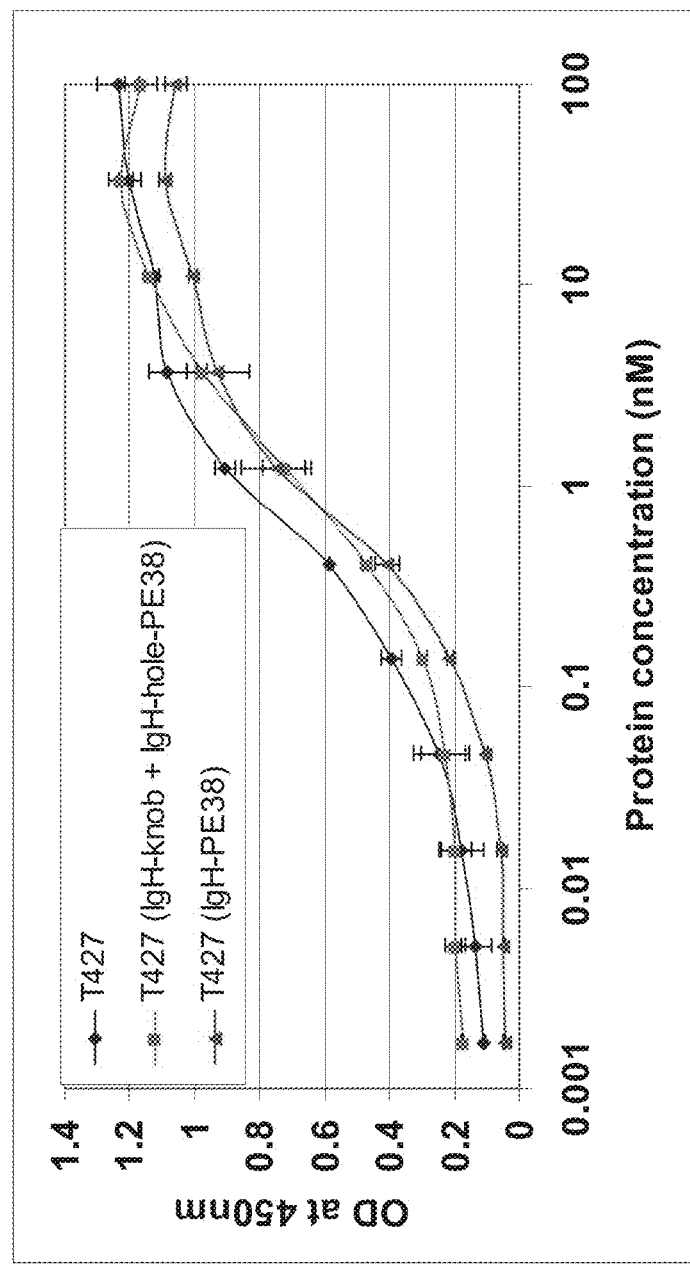
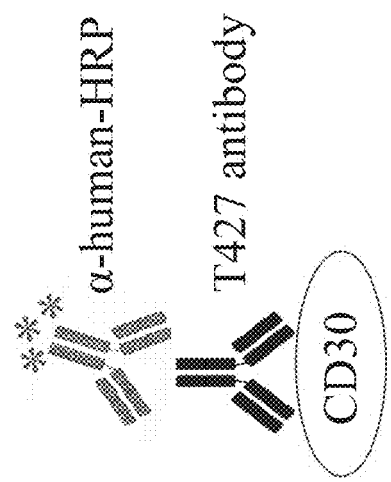

SEQUENCE LISTING

```
<160> NUMBER OF SEQ ID NOS: 75

<210> SEQ ID NO 1
<211> LENGTH: 75
<212> TYPE: DNA
<213> ORGANISM: Artificial sequence
<220> FEATURE:
<223> OTHER INFORMATION: Single strand DNA oligonucleotide

<400> SEQUENCE: 1
gaagcctttg accaggcacc acaggctgac ctggttcttg gtcatctcct cccggcatgg      60
gggcagggtg tacac                                                      75

<210> SEQ ID NO 2
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 2
ggatgggggc agggtgcaca cctgtggttc tcgg                                  34

<210> SEQ ID NO 3
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 3
ggatagaagc ctttgaccgc gcagctcagg ctgacctggt tcttg                      45

<210> SEQ ID NO 4
<211> LENGTH: 39
<212> TYPE: DNA
<213> ORGANISM: Artificial sequence
<220> FEATURE:
<223> OTHER INFORMATION: Single strand DNA oligonucleotide

<400> SEQUENCE: 4
gtccacggtg agcttgctaa cgaggaagaa ggagccgtc                             39

<210> SEQ ID NO 5
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 5
atatacatat ggacattgtg ctg                                              23

<210> SEQ ID NO 6
<211> LENGTH: 51
<212> TYPE: DNA
```

```
<213> ORGANISM: Artificial sequence
<220> FEATURE:
<223> OTHER INFORMATION: Single strand DNA oligonucleotide

<400> SEQUENCE: 6
tatatacgta cgtttgattt ccagtttggt gccgcaaccg aacgtccgag g       51

<210> SEQ ID NO 7
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 7
tatatagaat tcttactctc ccctgttgaa gctctttgtg                    40

<210> SEQ ID NO 8
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 8
aaacagaggc ctggacagtg tctggaatgg attg                          34

<210> SEQ ID NO 9
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 9
tatatagcta gcggaggaga ctgtgag                                  27

<210> SEQ ID NO 10
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 10
gcccaaatct gccgacaaaa ctcacacatg cccacc                        36

<210> SEQ ID NO 11
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 11
tgtgtgagtt ttgtcggcag atttgggctc aactctcttg                    40

<210> SEQ ID NO 12
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 12
gaggagatga ccaagaacca ggt                                     23
```

<210> SEQ ID NO 13
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 13

```
atatacatat gcaggtcaaa ctgc                                            24
```

<210> SEQ ID NO 14
<211> LENGTH: 660
<212> TYPE: DNA
<213> ORGANISM: Artificial sequence
<220> FEATURE:
<223> OTHER INFORMATION: Light chain T427 (wt IgG) coding sequence

<400> SEQUENCE: 14

```
atggacattg tgctgaccca atctccaact tctttggctg tgtctctagg gcagagggcc     60
accatatcct gcagagccag tgaaagtgtt gatagttatg caatagttta tatgcactgg    120
ttccagcaga aaccaggaca gccacccaaa ctcctcatct atcgtgcatc caacctagaa    180
tctgggatcc ctgccaggtt cagtggcagt gggtcttgga cagacttcac cctcaccatt    240
aatcctgtgg aggctgatga tgttgcaacc tattactgtc agcaaagtaa tgaggatcct    300
cggacgttcg gtggaggcac caaactggaa atcaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttaa    660
```

<210> SEQ ID NO 15
<211> LENGTH: 219
<212> TYPE: PRT
<213> ORGANISM: Artificial sequence
<220> FEATURE:
<223> OTHER INFORMATION: Light chain T427 (wt IgG)

<400> SEQUENCE: 15

```
Met Asp Ile Val Leu Thr Gln Ser Pro Thr Ser Leu Ala Val Ser Leu
1               5                   10                  15

Gly Gln Arg Ala Thr Ile Ser Cys Arg Ala Ser Glu Ser Val Asp Ser
            20                  25                  30

Tyr Gly Asn Ser Phe Met His Trp Phe Gln Gln Lys Pro Gly Gln Pro
        35                  40                  45

Pro Lys Leu Leu Ile Tyr Arg Ala Ser Asn Leu Glu Ser Gly Ile Pro
    50                  55                  60

Ala Arg Phe Ser Gly Ser Gly Ser Trp Thr Asp Phe Thr Leu Thr Ile
65                  70                  75                  80

Asn Pro Val Glu Ala Asp Asp Val Ala Thr Tyr Tyr Cys Gln Gln Ser
                85                  90                  95

Asn Glu Asp Pro Arg Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125
```

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 16
<211> LENGTH: 648
<212> TYPE: DNA
<213> ORGANISM: Artificial sequence
<220> FEATURE:
<223> OTHER INFORMATION: Light chain FRP5 (wt IgG) coding sequence

<400> SEQUENCE: 16

```
atggacatcc agctgaccca gtctcacaaa ttcctgtcca cttcagtagg agacagggtc      60
agcatcacct gcaaggccag tcaggatgtg tataatgctg ttgcctggta tcaacagaaa     120
ccaggacaat ctcctaaact tctgatttac tcggcatcct cccggtacac tggagtccct     180
tctcgcttca ctggcagtgg ctctgggccg gatttcactt tcaccatcag cagtgtgcag     240
gctgaagacc tggcagttta tttctgtcag caacattttc gtactccatt cacgttcggc     300
tcggggacaa aattggagat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgttaa                 648
```

<210> SEQ ID NO 17
<211> LENGTH: 215
<212> TYPE: PRT
<213> ORGANISM: Artificial sequence
<220> FEATURE:
<223> OTHER INFORMATION: Light chain FRP5 (wt IgG)

<400> SEQUENCE: 17

Met Asp Ile Gln Leu Thr Gln Ser His Lys Phe Leu Ser Thr Ser Val
1               5                   10                  15

Gly Asp Arg Val Ser Ile Thr Cys Lys Ala Ser Gln Asp Val Tyr Asn
            20                  25                  30

Ala Val Ala Trp Tyr Gln Gln Lys Pro Gly Ser Pro Lys Leu Leu
        35                  40                  45

Ile Tyr Ser Ala Ser Ser Arg Tyr Thr Gly Val Pro Ser Arg Phe Thr
    50                  55                  60

Gly Ser Gly Ser Gly Pro Asp Phe Thr Phe Thr Ile Ser Ser Val Gln
65                  70                  75                  80

Ala Glu Asp Leu Ala Val Tyr Phe Cys Gln Gln His Phe Arg Thr Pro
                85                  90                  95

Phe Thr Phe Gly Ser Gly Thr Lys Leu Glu Ile Lys Arg Thr Val Ala

```
                100               105                 110
Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 18
<211> LENGTH: 645
<212> TYPE: DNA
<213> ORGANISM: Artificial sequence
<220> FEATURE:
<223> OTHER INFORMATION: Light chain anti-Tac (wt IgG) coding sequence

<400> SEQUENCE: 18
atgcaaattg ttctcaccca gtctccagca atcatgtctg catctccagg ggagaaggtc      60
accataacct gcagtgccag ctcaagtata agttacatgc actggttcca gcagaagcca     120
ggcacttctc ccaaactctg gatttatacc acatccaacc tggcttctgg agtccctgct     180
cgcttcagtg gcagtggatc tgggacctct tactctctca caatcagccg aatggaggct     240
gaagatgctg ccacttatta ctgccatcaa aggagtactt acccactcac gttcggttct     300
gggaccaagc tggaaataaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac agggagagt gttaa                       645

<210> SEQ ID NO 19
<211> LENGTH: 214
<212> TYPE: PRT
<213> ORGANISM: Artificial sequence
<220> FEATURE:
<223> OTHER INFORMATION: Light chain anti-Tac (wt IgG)

<400> SEQUENCE: 19

Met Gln Ile Val Leu Thr Gln Ser Pro Ala Ile Met Ser Ala Ser Pro
1               5                   10                  15

Gly Glu Lys Val Thr Ile Thr Cys Ser Ala Ser Ser Ile Ser Tyr
            20                  25                  30

Met His Trp Phe Gln Gln Lys Pro Gly Thr Ser Pro Lys Leu Trp Ile
        35                  40                  45

Tyr Thr Thr Ser Asn Leu Ala Ser Gly Val Pro Ala Arg Phe Ser Gly
    50                  55                  60

Ser Gly Ser Gly Thr Ser Tyr Ser Leu Thr Ile Ser Arg Met Glu Ala
65                  70                  75                  80
```

Glu Asp Ala Ala Thr Tyr Tyr Cys His Gln Arg Ser Thr Tyr Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 657
<212> TYPE: DNA
<213> ORGANISM: Artificial sequence
<220> FEATURE:
<223> OTHER INFORMATION: Light chain T427 A104C:Cys218del (Cys) coding
      sequence

<400> SEQUENCE: 20
atggacattg tgctgaccca atctccaact tctttggctg tgtctctagg gcagagggcc      60
accatatcct gcagagccag tgaaagtgtt gatagttatg caatagttta tatgcactgg     120
ttccagcaga aaccaggaca gccacccaaa ctcctcatct atcgtgcatc caacctagaa     180
tctgggatcc ctgccaggtt cagtggcagt gggtcttgga cagacttcac cctcaccatt     240
aatcctgtgg aggctgatga tgttgcaacc tattactgtc agcaaagtaa tgaggatcct     300
cggacgttcg gttgtggcac caaactggaa atcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtaa       657

<210> SEQ ID NO 21
<211> LENGTH: 218
<212> TYPE: PRT
<213> ORGANISM: Artificial sequence
<220> FEATURE:
<223> OTHER INFORMATION: Light chain T427 A104C:Cys218del (Cys)

<400> SEQUENCE: 21

Met Asp Ile Val Leu Thr Gln Ser Pro Thr Ser Leu Ala Val Ser Leu
1               5                   10                  15

Gly Gln Arg Ala Thr Ile Ser Cys Arg Ala Ser Glu Ser Val Asp Ser
            20                  25                  30

Tyr Gly Asn Ser Phe Met His Trp Phe Gln Gln Lys Pro Gly Gln Pro
        35                  40                  45

```
Pro Lys Leu Leu Ile Tyr Arg Ala Ser Asn Leu Glu Ser Gly Ile Pro
 50                  55                  60
Ala Arg Phe Ser Gly Ser Gly Ser Trp Thr Asp Phe Thr Leu Thr Ile
 65                  70                  75                  80
Asn Pro Val Glu Ala Asp Asp Val Ala Thr Tyr Tyr Cys Gln Gln Ser
                 85                  90                  95
Asn Glu Asp Pro Arg Thr Phe Gly Cys Gly Thr Lys Leu Glu Ile Lys
                100                 105                 110
Arg Thr Val Ala Ala Pro Ser Val Phe Ile Phe Pro Pro Ser Asp Glu
            115                 120                 125
Gln Leu Lys Ser Gly Thr Ala Ser Val Val Cys Leu Leu Asn Asn Phe
        130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu
    210                 215
```

<210> SEQ ID NO 22
<211> LENGTH: 1353
<212> TYPE: DNA
<213> ORGANISM: Artificial sequence
<220> FEATURE:
<223> OTHER INFORMATION: Heavy chain T427 (wt IgG human gamma 1) coding sequence

<400> SEQUENCE: 22

```
atgcaggtcc aactgcagca gccggggact gaactggtga ggcctggagc ttcagtgaag    60
ctgtcctgca aggcttctgg cttctccttc accagttact ggatgaactg ggtgaagcag   120
aggcctggaa aaggccttga gtggattggc atgattcatc cttccgatag tgaaactagg   180
ttaaatcaga agttcaagga cagggccaca ttgactgtag acaaatcctc cagcacagcc   240
tacatgcaac tcagcagccc gacatctgag gactctgcgg tctattactg tgcaagtgag   300
atggattatt actttgctat ggactactgg ggtcaaggaa cctcagtcac cgtctcctca   360
gctagcacca agggcccatc ggtcttcccc ctggcaccct cctccaagag cacctctggg   420
ggcacagcgg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacccagacc   600
tacatctgca acgtgaatca caagcccagc aacaccaagg tggacaagaa agttgagccc   660
aaatcttgtg acaaaactca cacatgccca ccgtgcccag cacctgaact cctggggggga   720
ccgtcagtct tcctcttccc cccaaaaccc aaggacaccc tcatgatctc ccggacccct   780
gaggtcacat gcgtggtggt ggacgtgagc cacgaagacc ctgaggtcaa gttcaactgg   840
tacgtggacg gcgtggaggt gcataatgcc aagacaaagc cgcgggagga gcagtacaac   900
agcacgtacc gtgtggtcag cgtcctcacc gtcctgcacc aggactggct gaatggcaag   960
gagtacaagt gcaaggtctc caacaaagcc ctcccagccc ccatcgagaa aaccatctcc  1020
```

```
aaagccaaag ggcagccccg agaaccacag gtgtacaccc tgcccccatc ccgggaggag    1080
atgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctat agcaagctca ccgtggacaa gagcaggtgg    1260 cagcaggga acgtcttctc atgctccgtg atgcatgagg ctctgcacaa ccactacacg    1320
cagaagagcc tctccctgtc cccgggtaaa tga                                 1353
```

<210> SEQ ID NO 23
<211> LENGTH: 450
<212> TYPE: PRT
<213> ORGANISM: Artificial sequence
<220> FEATURE:
<223> OTHER INFORMATION: Heavy chain T427 (wt IgG human gamma 1)

<400> SEQUENCE: 23

```
Met Gln Val Gln Leu Gln Gln Pro Gly Thr Glu Leu Val Arg Pro Gly
1               5                   10                  15

Ala Ser Val Lys Leu Ser Cys Lys Ala Ser Gly Phe Ser Phe Thr Ser
            20                  25                  30

Tyr Trp Met Asn Trp Val Lys Gln Arg Pro Gly Gln Gly Leu Glu Trp
        35                  40                  45

Ile Gly Met Ile His Pro Ser Asp Ser Glu Thr Arg Leu Asn Gln Lys
    50                  55                  60

Phe Lys Asp Arg Ala Thr Leu Thr Val Asp Lys Ser Ser Ser Thr Ala
65                  70                  75                  80

Tyr Met Gln Leu Ser Ser Pro Thr Ser Glu Asp Ser Ala Val Tyr Tyr
                85                  90                  95

Cys Ala Ser Glu Met Asp Tyr Tyr Phe Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 24
<211> LENGTH: 1353
<212> TYPE: DNA
<213> ORGANISM: Artificial sequence
<220> FEATURE:
<223> OTHER INFORMATION: Heavy chain FRP5 (wt IgG human gamma 1) coding
      sequence

<400> SEQUENCE: 24
atgcaggtac aactgcagca gtctggacct gaactgaaga agcctggaga gacagtcaag      60
atctcctgca aggcctctgg gtatcctttc acaaactatg gaatgaactg ggtgaagcag     120
gctccaggac agggtttaaa gtggatgggc tggattaaca cctccactgg agagtcaaca     180
tttgctgatg acttcaaggg acggtttgac ttctctttgg aaacctctgc caacactgcc     240
tatttgcaga tcaacaacct caaaagtgaa gacatggcta catatttctg tgcaagatgg     300
gaggtttacc acggctacgt tccttactgg ggccaaggga ccacggtcac cgtttcctct     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctggggga      720 ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag ggcagccccg agaaccacag gtgtacaccc tgcccccatc ccgggaggag    1080
atgaccaaga accaggtcag cctgacctgc ctggtcaaag gcttctatcc cagcgacatc    1140
```

-continued

```
gccgtggagt gggagagcaa tgggcagccg gagaacaact acaagaccac gcctcccgtg    1200
ctggactccg acggctcctt cttcctctat agcaagctca ccgtggacaa gagcaggtgg    1260
cagcagggga acgtcttctc atgctccgtg atgcatgagg ctctgcacaa ccactacacg    1320
cagaagagcc tctccctgtc cccgggtaaa tga                                 1353
```

<210> SEQ ID NO 25
<211> LENGTH: 450
<212> TYPE: PRT
<213> ORGANISM: Artificial sequence
<220> FEATURE:
<223> OTHER INFORMATION: Heavy chain FRP5 (wt IgG human gamma 1)

<400> SEQUENCE: 25

```
Met Gln Val Gln Leu Gln Gln Ser Gly Pro Glu Leu Lys Lys Pro Gly
1               5                   10                  15

Glu Thr Val Lys Ile Ser Cys Lys Ala Ser Gly Tyr Pro Phe Thr Asn
            20                  25                  30

Tyr Gly Met Asn Trp Val Lys Gln Ala Pro Gly Gln Gly Leu Lys Trp
        35                  40                  45

Met Gly Trp Ile Asn Thr Ser Thr Gly Glu Ser Thr Phe Ala Asp Asp
    50                  55                  60

Phe Lys Gly Arg Phe Asp Phe Ser Leu Glu Thr Ser Ala Asn Thr Ala
65                  70                  75                  80

Tyr Leu Gln Ile Asn Asn Leu Lys Ser Glu Asp Met Ala Thr Tyr Phe
                85                  90                  95

Cys Ala Arg Trp Glu Val Tyr His Gly Tyr Val Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

```
              325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
                355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
    450

<210> SEQ ID NO 26
<211> LENGTH: 1344
<212> TYPE: DNA
<213> ORGANISM: Artificial sequence
<220> FEATURE:
<223> OTHER INFORMATION: Heavy chain anti-Tac (wt IgG human gamma 1)
      coding sequence

<400> SEQUENCE: 26
atgcaggtca aactgcagga gtctggggct gaactggcaa acctggggc ctcagtgaag      60 atgtcctgca aggcttctgg ctacaccttt actagctaca ggatgcactg ggtaaaacag    120
aggcctggac agggtctgga atggattgga tatattaatc ctagcactgg gtatactgaa    180
tacaatcaga agttcaagga caaggccaca ttgactgcag acaaatcctc cagcacagcc    240
tacatgcaac tgagcagcct gacatttgag gactctgcag tctattactg tgcaagaggg    300 ggggggtct ttgactactg gggccaagga ccactctca cagtctcctc cgctagcacc      360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660 gacaaaactc acacatgccc accgtgccca gcacctgaac tcctgggggg accgtcagtc    720
ttcctcttcc cccaaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaccatctc caaagccaaa   1020 gggcagcccc gagaaccaca ggtgtacacc ctgcccccat cccgggagga gatgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta tagcaagctc accgtggaca agagcaggtg gcagcagggg   1260
```

```
aacgtcttct catgctccgt gatgcatgag gctctgcaca accactacac gcagaagagc    1320 ctctcccctgt ccccgggtaa atga                                          1344
```

<210> SEQ ID NO 27
<211> LENGTH: 447
<212> TYPE: PRT
<213> ORGANISM: Artificial sequence
<220> FEATURE:
<223> OTHER INFORMATION: Heavy chain anti-Tac (wt IgG human gamma 1)

<400> SEQUENCE: 27

```
Met Gln Val Lys Leu Gln Glu Ser Gly Ala Glu Leu Ala Lys Pro Gly
1               5                   10                  15

Ala Ser Val Lys Met Ser Cys Lys Ala Ser Gly Tyr Thr Phe Thr Ser
            20                  25                  30

Tyr Arg Met His Trp Val Lys Gln Arg Pro Gly Gln Gly Leu Glu Trp
        35                  40                  45

Ile Gly Tyr Ile Asn Pro Ser Thr Gly Tyr Thr Glu Tyr Asn Gln Lys
    50                  55                  60

Phe Lys Asp Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Tyr
                85                  90                  95

Cys Ala Arg Gly Gly Gly Val Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 28
<211> LENGTH: 1353
<212> TYPE: DNA
<213> ORGANISM: Artificial sequence
<220> FEATURE:
<223> OTHER INFORMATION: Heavy chain T427 T366W:S354C (knob) coding
      sequence

<400> SEQUENCE: 28
atgcaggtcc aactgcagca gccggggact gaactggtga ggcctggagc ttcagtgaag      60
ctgtcctgca aggcttctgg cttctccttc accagttact ggatgaactg ggtgaagcag     120
aggcctggac aaggccttga gtggattggc atgattcatc cttccgatag tgaaactagg     180
ttaaatcaga agttcaagga cagggccaca ttgactgtag acaaatcctc cagcacagcc     240
tacatgcaac tcagcagccc gacatctgag gactctgcgg tctattactg tgcaagtgag     300
atggattatt actttgctat ggactactgg ggtcaaggaa cctcagtcac cgtctcctca     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctgggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc catcgagaaa accatctcc    1020
aaagccaaag gcagccccg agaaccacag gtgtacaccc tgcccccatg ccggaggag    1080
atgaccaaga accaggtcag cctgtggtgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctat agcaagctca ccgtggacaa gagcaggtgg    1260
cagcagggga acgtcttctc atgctccgtg atgcatgagg ctctgcacaa ccactacacg    1320
cagaagagcc tctccctgtc cccgggtaaa tga                                 1353

<210> SEQ ID NO 29
<211> LENGTH: 465
```

<212> TYPE: PRT
<213> ORGANISM: Artificial sequence
<220> FEATURE:
<223> OTHER INFORMATION: Heavy chain T427 T366W:S354C (knob) coding sequence

<400> SEQUENCE: 29

Met Gln Val Gln Leu Gln Gln Pro Gly Thr Glu Leu Val Arg Pro Gly
1               5                   10                  15

Ala Ser Val Lys Leu Ser Cys Lys Ala Ser Gly Phe Ser Phe Thr Ser
            20                  25                  30

Tyr Trp Met Asn Trp Val Lys Gln Arg Pro Gly Gln Gly Leu Glu Trp
        35                  40                  45

Ile Gly Met Ile His Pro Ser Asp Ser Glu Thr Arg Leu Asn Gln Lys
50                  55                  60

Phe Lys Asp Arg Ala Thr Leu Thr Val Asp Lys Ser Ser Ser Thr Ala
65                  70                  75                  80

Tyr Met Gln Leu Ser Ser Pro Thr Ser Glu Asp Ser Ala Val Tyr Tyr
                85                  90                  95

Cys Ala Ser Glu Met Asp Tyr Tyr Phe Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Glu Pro
                245                 250                 255

Lys Ser Cys Asp Lys Thr His Thr Cys Pro Pro Cys Pro Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Cys Arg Glu Glu Met Thr Lys Asn Gln Val Ser Leu Trp
370                 375                 380

```
Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Lys Leu Thr Val Asp Lys
        420                 425                 430

Ser Arg Trp Gln Gln Gly Asn Val Phe Ser Cys Ser Val Met His Glu
    435                 440                 445

Ala Leu His Asn His Tyr Thr Gln Lys Ser Leu Ser Leu Ser Pro Gly
    450                 455                 460

Lys
465

<210> SEQ ID NO 30
<211> LENGTH: 1352
<212> TYPE: DNA
<213> ORGANISM: Artificial sequence
<220> FEATURE:
<223> OTHER INFORMATION: Heavy chain T427 T366S:L368A:Y407V:Y349C (hole)
      coding sequence

<400> SEQUENCE: 30
atgcaggtcc aactgcagca gccggggact gaactggtga ggcctggagc ttcagtgaag      60
ctgtcctgca aggcttctgg cttctccttc accagttact ggatgaactg ggtgaagcag     120
aggcctggac aaggccttga gtggattggc atgattcatc cttccgatag tgaaactagg     180
ttaaatcaga agttcaagga cagggccaca ttgactgtag acaaatcctc cagcacagcc     240
tacatgcaac tcagcagccc gacatctgag gactctgcgg tctattactg caagtgagag     300
atggattatt actttgctat ggactactgg ggtcaaggaa cctcagtcac cgtctcctca     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact gaacaaggac     720
cgtcagtctt cctcttcccc ccaaaaccca aggacaccct catgatctcc cggacccctg     780
aggtcacatg cgtggtggtg gacgtgagcc acgaagaccc tgaggtcaag ttcaactggt     840
acgtggacgg cgtggaggtg cataatgcca agacaaagcc gcgggaggag cagtacaaca     900
gcacgtaccg tgtggtcagc gtcctcaccg tcctgcacca ggactggctg aatggcaagg     960
agtacaagtg caaggtctcc aacaaagccc tcccagcccc catcgagaaa accatctcca    1020
aagccaaagg gcagccccga gaaccacagg tgtgcaccct gcccccatcc cgggaggaga    1080
tgaccaagaa ccaggtcagc ctgagctgcg cggtcaaagg cttctatccc agcgacatcg    1140
ccgtggagtg ggagagcaat gggcagccgg agaacaacta caagaccacg cctcccgtgc    1200
tggactccga cggctccttc ttcctcgtta gcaagctcac cgtggacaag agcaggtggc    1260
agcaggggaa cgtcttctca tgctccgtga tgcatgaggc tctgcacaac cactacacgc    1320
agaagagcct ctccctgtcc ccgggtaaat ga                                  1352

<210> SEQ ID NO 31
<211> LENGTH: 450
```

```
<212> TYPE: PRT
<213> ORGANISM: Artificial sequence
<220> FEATURE:
<223> OTHER INFORMATION: Heavy chain T427 T366S:L368A:Y407V:Y349C (hole)

<400> SEQUENCE: 31
```

| | | | | | | | | | | | | | | |
|---|---|---|---|---|---|---|---|---|---|---|---|---|---|---|
| Met | Gln | Val | Gln | Leu | Gln | Gln | Pro | Gly | Thr | Glu | Leu | Val | Arg | Pro | Gly |
| 1 | | | | 5 | | | | | 10 | | | | | 15 | |
| Ala | Ser | Val | Lys | Leu | Ser | Cys | Lys | Ala | Ser | Gly | Phe | Ser | Phe | Thr | Ser |
| | | | 20 | | | | | 25 | | | | | 30 | | |
| Tyr | Trp | Met | Asn | Trp | Val | Lys | Gln | Arg | Pro | Gly | Gln | Gly | Leu | Glu | Trp |
| | | | 35 | | | | | 40 | | | | | 45 | | |
| Ile | Gly | Met | Ile | His | Pro | Ser | Asp | Ser | Glu | Thr | Arg | Leu | Asn | Gln | Lys |
| | | 50 | | | | | 55 | | | | | 60 | | | |
| Phe | Lys | Asp | Arg | Ala | Thr | Leu | Thr | Val | Asp | Lys | Ser | Ser | Ser | Thr | Ala |
| 65 | | | | | 70 | | | | | 75 | | | | | 80 |
| Tyr | Met | Gln | Leu | Ser | Ser | Pro | Thr | Ser | Glu | Asp | Ser | Ala | Val | Tyr | Tyr |
| | | | | 85 | | | | | 90 | | | | | 95 | |
| Cys | Ala | Ser | Glu | Met | Asp | Tyr | Tyr | Phe | Ala | Met | Asp | Tyr | Trp | Gly | Gln |
| | | | 100 | | | | | 105 | | | | | 110 | | |
| Gly | Thr | Ser | Val | Thr | Val | Ser | Ser | Ala | Ser | Thr | Lys | Gly | Pro | Ser | Val |
| | | | 115 | | | | | 120 | | | | | 125 | | |
| Phe | Pro | Leu | Ala | Pro | Ser | Ser | Lys | Ser | Thr | Ser | Gly | Gly | Thr | Ala | Ala |
| | | 130 | | | | | 135 | | | | | 140 | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Gln | Thr | Tyr | Ile | Cys | Asn | Val | Asn | His | Lys |
| | | 195 | | | | | 200 | | | | | 205 | | | |
| Pro | Ser | Asn | Thr | Lys | Val | Asp | Lys | Lys | Val | Glu | Pro | Lys | Ser | Cys | Asp |
| 210 | | | | | 215 | | | | | 220 | | | | | |
| Lys | Thr | His | Thr | Cys | Pro | Pro | Cys | Pro | Ala | Pro | Glu | Leu | Leu | Gly | Gly |
| 225 | | | | | 230 | | | | | 235 | | | | | 240 |
| Pro | Ser | Val | Phe | Leu | Phe | Pro | Pro | Lys | Pro | Lys | Asp | Thr | Leu | Met | Ile |
| | | | | 245 | | | | | 250 | | | | | 255 | |
| Ser | Arg | Thr | Pro | Glu | Val | Thr | Cys | Val | Val | Val | Asp | Val | Ser | His | Glu |
| | | | 260 | | | | | 265 | | | | | 270 | | |
| Asp | Pro | Glu | Val | Lys | Phe | Asn | Trp | Tyr | Val | Asp | Gly | Val | Glu | Val | His |
| | | 275 | | | | | 280 | | | | | 285 | | | |
| Asn | Ala | Lys | Thr | Lys | Pro | Arg | Glu | Glu | Gln | Tyr | Asn | Ser | Thr | Tyr | Arg |
| 290 | | | | | 295 | | | | | 300 | | | | | |
| Val | Val | Ser | Val | Leu | Thr | Val | Leu | His | Gln | Asp | Trp | Leu | Asn | Gly | Lys |
| 305 | | | | | 310 | | | | | 315 | | | | | 320 |
| Glu | Tyr | Lys | Cys | Lys | Val | Ser | Asn | Lys | Ala | Leu | Pro | Ala | Pro | Ile | Glu |
| | | | | 325 | | | | | 330 | | | | | 335 | |
| Lys | Thr | Ile | Ser | Lys | Ala | Lys | Gly | Gln | Pro | Arg | Glu | Pro | Gln | Val | Cys |
| | | | 340 | | | | | 345 | | | | | 350 | | |
| Thr | Leu | Pro | Pro | Ser | Arg | Glu | Glu | Met | Thr | Lys | Asn | Gln | Val | Ser | Leu |
| | | 355 | | | | | 360 | | | | | 365 | | | |
| Ser | Cys | Ala | Val | Lys | Gly | Phe | Tyr | Pro | Ser | Asp | Ile | Ala | Val | Glu | Trp |
| | | 370 | | | | | 375 | | | | | 380 | | | |

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 32
<211> LENGTH: 2406
<212> TYPE: DNA
<213> ORGANISM: Artificial sequence
<220> FEATURE:
<223> OTHER INFORMATION: Heavy chain T427-PE38 coding sequence

<400> SEQUENCE: 32
```

| | | |
|---|---|---|
| atgcaggtcc aactgcagca gccggggact gaactggtga ggcctggagc ttcagtgaag | 60 |
| ctgtcctgca aggcttctgg cttctccttc accagttact ggatgaactg ggtgaagcag | 120 |
| aggcctggac aaggccttga gtggattggc atgattcatc cttccgatag tgaaactagg | 180 |
| ttaaatcaga gagttcaagga cagggccaca ttgactgtag acaaatcctc cagcacagcc | 240 |
| tacatgcaac tcagcagccc gacatctgag gactctgcgg tctattactg tgcaagtgag | 300 |
| atggattatt actttgctat ggactactgg ggtcaaggaa cctcagtcac cgtctcctca | 360 |
| gctagcacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagaa agttgagccc | 660 |
| aaatcttgtg acaaaactca cacatgccca ccgtgcccag cacctgaact cctggggggga | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacaac | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |
| aaagccaaag ggcagccccg agaaccacag gtgtacaccc tgcccccatc ccgggaggag | 1080 |
| atgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctat agcaagctca ccgtggacaa gagcaggtgg | 1260 |
| cagcagggga acgtcttctc atgctccgtg atgcatgagg ctctgcacaa ccactacacg | 1320 |
| cagaagagcc tctccctgtc cccgggtaaa gcttccggag gtcccgaggg cggcagcctg | 1380 |
| gccgcgctga ccgcgcacca ggcttgccac ctgccgctgg agactttcac ccgtcatcgc | 1440 |
| cagccgcgcg gctgggaaca actggagcag tgcggctatc cggtgcagcg gctggtcgcc | 1500 |
| ctctacctgg cggcgcggct gtcgtggaac caggtcgacc aggtgatccg caacgccctg | 1560 |
| gccagccccg gcagcggcgg cgacctgggc gaagcgatcc gcgagcagcc ggagcaggcc | 1620 |

```
cgtctggccc tgaccctggc cgccgccgag agcgagcgct tcgtccggca gggcaccggc    1680
aacgacgagg ccggcgcggc caacggcccg gcggacagcg cgacgcccct gctggagcgc    1740
aactatccca ctggcgcgga gttcctcggc gacggcggcg acgtcagctt cagcacccgc    1800
ggcacgcaga actggacggt ggagcggctg ctccaggcgc accgccaact ggaggagcgc    1860
ggctatgtgt tcgtcggcta ccacggcacc ttcctcgaag cggcgcaaag catcgtcttc    1920
ggcggggtgc gcgcgcgcag ccaggacctc gacgcgatct ggcgcggttt ctatatcgcc    1980
ggcgatccgg cgctggccta cggctacgcc caggaccagg aacccgacgc acgcggccgg    2040
atccgcaacg gtgccctgct gcgggtctat gtgccgcgct cgagcctgcc gggcttctac    2100
cgcaccagcc tgaccctggc cgcgccggag gcggcgggcg aggtcgaacg gctgatcggc    2160
catccgctgc cgctgcgcct ggacgccatc accggccccg aggaggaagg cgggcgcctg    2220
gagaccattc tcggctggcc gctggccgag cgcaccgtgg tgattccctc ggcgatcccc    2280
accgacccgc gcaacgtcgg cggcgacctc gacccgtcca gcatccccga caaggaacag    2340
gcgatcagcg ccctgccgga ctacgccagc agcccggca  accgccgcg cgaggacctg    2400 aagtaa                                                              2406
```

<210> SEQ ID NO 33
<211> LENGTH: 800
<212> TYPE: PRT
<213> ORGANISM: Artificial sequence
<220> FEATURE:
<223> OTHER INFORMATION: Heavy chain T427-PE38

<400> SEQUENCE: 33

```
Gln Val Gln Leu Gln Gln Pro Gly Thr Glu Leu Val Arg Pro Gly Ala
  1               5                  10                  15

Ser Val Lys Leu Ser Cys Lys Ala Ser Gly Phe Ser Phe Thr Ser Tyr
             20                  25                  30

Trp Met Asn Trp Val Lys Gln Arg Pro Gly Gln Gly Leu Glu Trp Ile
         35                  40                  45

Gly Met Ile His Pro Ser Asp Ser Glu Thr Arg Leu Asn Gln Lys Phe
     50                  55                  60

Lys Asp Arg Ala Thr Leu Thr Val Asp Lys Ser Ser Ser Thr Ala Tyr
 65                  70                  75                  80

Met Gln Leu Ser Ser Pro Thr Ser Glu Asp Ser Ala Val Tyr Tyr Cys
                 85                  90                  95

Ala Ser Glu Met Asp Tyr Tyr Phe Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

-continued

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Ala Ser Gly Gly Pro Glu Gly Gly Ser Leu Ala Ala Leu Thr Ala
    450                 455                 460

His Gln Ala Cys His Leu Pro Leu Glu Thr Phe Thr Arg His Arg Gln
465                 470                 475                 480

Pro Arg Gly Trp Glu Gln Leu Glu Gln Cys Gly Tyr Pro Val Gln Arg
                485                 490                 495

Leu Val Ala Leu Tyr Leu Ala Ala Arg Leu Ser Trp Asn Gln Val Asp
            500                 505                 510

Gln Val Ile Arg Asn Ala Leu Ala Ser Pro Gly Ser Gly Gly Asp Leu
        515                 520                 525

Gly Glu Ala Ile Arg Glu Gln Pro Glu Gln Ala Arg Leu Ala Leu Thr
530                 535                 540

Leu Ala Ala Ala Glu Ser Glu Arg Phe Val Arg Gln Gly Thr Gly Asn
545                 550                 555                 560

Asp Glu Ala Gly Ala Ala Asn Gly Pro Ala Asp Ser Gly Asp Ala Leu
                565                 570                 575

Leu Glu Arg Asn Tyr Pro Thr Gly Ala Glu Phe Leu Gly Asp Gly Gly
            580                 585                 590

Asp Val Ser Phe Ser Thr Arg Gly Thr Gln Asn Trp Thr Val Glu Arg
        595                 600                 605

Leu Leu Gln Ala His Arg Gln Leu Glu Glu Arg Gly Tyr Val Phe Val
610                 615                 620

Gly Tyr His Gly Thr Phe Leu Glu Ala Ala Gln Ser Ile Val Phe Gly
625                 630                 635                 640
```

```
Gly Val Arg Ala Arg Ser Gln Asp Leu Asp Ala Ile Trp Arg Gly Phe
            645                 650                 655

Tyr Ile Ala Gly Asp Pro Ala Leu Ala Tyr Gly Tyr Ala Gln Asp Gln
        660                 665                 670

Glu Pro Asp Ala Arg Gly Arg Ile Arg Asn Gly Ala Leu Leu Arg Val
    675                 680                 685

Tyr Val Pro Arg Ser Ser Leu Pro Gly Phe Tyr Arg Thr Ser Leu Thr
690                 695                 700

Leu Ala Ala Pro Glu Ala Gly Glu Val Glu Arg Leu Ile Gly His
705                 710                 715                 720

Pro Leu Pro Leu Arg Leu Asp Ala Ile Thr Gly Pro Glu Glu Gly
                725                 730                 735

Gly Arg Leu Glu Thr Ile Leu Gly Trp Pro Leu Ala Glu Arg Thr Val
            740                 745                 750

Val Ile Pro Ser Ala Ile Pro Thr Asp Pro Arg Asn Val Gly Gly Asp
        755                 760                 765

Leu Asp Pro Ser Ser Ile Pro Asp Lys Glu Gln Ala Ile Ser Ala Leu
    770                 775                 780

Pro Asp Tyr Ala Ser Gln Pro Gly Lys Pro Pro Arg Glu Asp Leu Lys
785                 790                 795                 800

<210> SEQ ID NO 34
<211> LENGTH: 2406
<212> TYPE: DNA
<213> ORGANISM: Artificial sequence
<220> FEATURE:
<223> OTHER INFORMATION: Heavy chain T427-PE38 T366S:L368A:Y407V:Y349C
      (hole) coding sequence

<400> SEQUENCE: 34
atgcaggtcc aactgcagca gccgggggact gaactggtga ggcctggagc ttcagtgaag    60
ctgtcctgca aggcttctgg cttctccttc accagttact ggatgaactg ggtgaagcag   120
aggcctggaa aggccttga gtggattggc atgattcatc cttccgatag tgaaactagg   180
ttaaatcaga agttcaagga cagggccaca ttgactgtag acaaatcctc cagcacagcc   240
tacatgcaac tcagcagccc gacatctgag gactctgcgg tctattactg tgcaagtgag   300
atggattatt actttgctat ggactactgg ggtcaaggaa cctcagtcac cgtctcctca   360
gctagcacca agggcccatc ggtcttcccc ctggcaccct cctccaagag cacctctggg   420
ggcacagcgg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacccagacc   600
tacatctgca acgtgaatca caagcccagc aacaccaagg tggacaagaa agttgagccc   660
aaatcttgtg acaaaactca cacatgccca ccgtgcccag cacctgaact cctggggggga   720 ccgtcagtct tcctcttccc cccaaaaccc aaggacaccc tcatgatctc ccggacccct   780
gaggtcacat gcgtggtggt ggacgtgagc cacgaagacc ctgaggtcaa gttcaactgg   840
tacgtggacg gcgtggaggt gcataatgcc aagacaaagc cgcgggagga gcagtacaac   900
agcacgtacc gtgtggtcag cgtcctcacc gtcctgcacc aggactggct gaatggcaag   960
gagtacaagt gcaaggtctc caacaaagcc ctcccagccc ccatcgagaa aaccatctcc  1020
aaagccaaag ggcagccccg agaaccacag gtgtgcaccc tgcccccatc ccgggaggag  1080
atgaccaaga accaggtcag cctgagctgc gcggtcaaag gcttctatcc cagcgacatc  1140
```

-continued

```
gccgtggagt gggagagcaa tgggcagccg agaacaact acaagaccac gcctcccgtg      1200
ctggactccg acggctcctt cttcctcgtt agcaagctca ccgtggacaa gagcaggtgg     1260
cagcagggga acgtcttctc atgctccgtg atgcatgagg ctctgcacaa ccactacacg     1320
cagaagagcc tctccctgtc cccgggtaaa gcttccggag gtcccgaggg cggcagcctg     1380
gccgcgctga ccgcgcacca ggcttgccac ctgccgctgg agactttcac ccgtcatcgc     1440
cagccgcgcg gctgggaaca actggagcag tgcggctatc cggtgcagcg gctggtcgcc     1500
ctctacctgg cggcgcggct gtcgtggaac caggtcgacc aggtgatccg caacgccctg     1560
gccagccccg gcagcggcgg cgacctgggc gaagcgatcc gcgagcagcc ggagcaggcc     1620
cgtctggccc tgaccctggc cgccgccgag agcgagcgct tcgtccggca gggcaccggc     1680
aacgacgagg ccggcgcggc caacggcccg gcggacagcg gcgacgccct gctggagcgc     1740
aactatccca ctggcgcgga gttcctcggc gacggcggcg acgtcagctt cagcacccgc     1800
ggcacgcaga actggacggt ggagcggctg ctccaggcgc accgccaact ggaggagcgc     1860
ggctatgtgt tcgtcggcta ccacggcacc ttcctcgaag cggcgcaaag catcgtcttc     1920
ggcggggtgc cgcgcgcgcag ccaggacctc gacgcgatct ggcgcggttt ctatatcgcc    1980
ggcgatccgc cgctggccta cggctacgcc caggaccagg aacccgacgc acgcggccgg    2040
atccgcaacg gtgccctgct gcgggtctat gtgccgcgct cgagcctgcc gggcttctac    2100
cgcaccagcc tgaccctggc cgccgccgag gcggcgggcg aggtcgaacg gctgatcggc    2160
catccgctgc cgctgcgcct ggacgccatc accggccccg aggaggaagg cgggcgcctg    2220
gagaccattc tcggctggcc gctggccgag cgcaccgtgg tgattccctc ggcgatcccc    2280
accgacccgc gcaacgtcgg cggcgacctc gacccgtcca gcatccccga caaggaacag    2340
gcgatcagcg ccctgccgga ctacgccagc cagcccggca accgccgcg cgaggacctg     2400
aagtaa                                                                2406
```

<210> SEQ ID NO 35
<211> LENGTH: 800
<212> TYPE: PRT
<213> ORGANISM: Artificial sequence
<220> FEATURE:
<223> OTHER INFORMATION: Heavy chain T427-PE38 T366S:L368A:Y407V:Y349C (hole)

<400> SEQUENCE: 35

```
Gln Val Gln Leu Gln Gln Pro Gly Thr Glu Leu Val Arg Pro Gly Ala
1               5                   10                  15

Ser Val Lys Leu Ser Cys Lys Ala Ser Gly Phe Ser Phe Thr Ser Tyr
            20                  25                  30

Trp Met Asn Trp Val Lys Gln Arg Pro Gly Gln Gly Leu Glu Trp Ile
        35                  40                  45

Gly Met Ile His Pro Ser Asp Ser Glu Thr Arg Leu Asn Gln Lys Phe
    50                  55                  60

Lys Asp Arg Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Ser Glu Met Asp Tyr Tyr Phe Ala Met Asp Tyr Trp Gly Gln Gly
            100                 105                 110

Thr Ser Val Thr Val Ser Ser Ala Ser Thr Lys Gly Pro Ser Val Phe
        115                 120                 125
```

```
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Cys Thr
            340                 345                 350
Leu Pro Pro Ser Arg Glu Glu Met Thr Lys Asn Gln Val Ser Leu Ser
        355                 360                 365
Cys Ala Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Val Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys Ala Ser Gly Gly Pro Glu Gly Gly Ser Leu Ala Ala Leu Thr Ala
    450                 455                 460
His Gln Ala Cys His Leu Pro Leu Glu Thr Phe Thr Arg His Arg Gln
465                 470                 475                 480
Pro Arg Gly Trp Glu Gln Leu Glu Gln Cys Gly Tyr Pro Val Gln Arg
                485                 490                 495
Leu Val Ala Leu Tyr Leu Ala Ala Arg Leu Ser Trp Asn Gln Val Asp
            500                 505                 510
Gln Val Ile Arg Asn Ala Leu Ala Ser Pro Gly Ser Gly Gly Asp Leu
        515                 520                 525
Gly Glu Ala Ile Arg Glu Gln Pro Glu Gln Ala Arg Leu Ala Leu Thr
    530                 535                 540
Leu Ala Ala Ala Glu Ser Glu Arg Phe Val Arg Gln Gly Thr Gly Asn
```

Asp Glu Ala Gly Ala Ala Asn Gly Pro Ala Asp Ser Gly Asp Ala Leu
545                 550                 555                 560
                565                 570                 575

Leu Glu Arg Asn Tyr Pro Thr Gly Ala Glu Phe Leu Gly Asp Gly Gly
                580                 585                 590

Asp Val Ser Phe Ser Thr Arg Gly Thr Gln Asn Trp Thr Val Glu Arg
                595                 600                 605

Leu Leu Gln Ala His Arg Gln Leu Glu Arg Gly Tyr Val Phe Val
    610                 615                 620

Gly Tyr His Gly Thr Phe Leu Glu Ala Ala Gln Ser Ile Val Phe Gly
625                 630                 635                 640

Gly Val Arg Ala Arg Ser Gln Asp Leu Asp Ala Ile Trp Arg Gly Phe
                645                 650                 655

Tyr Ile Ala Gly Asp Pro Ala Leu Ala Tyr Gly Tyr Ala Gln Asp Gln
                660                 665                 670

Glu Pro Asp Ala Arg Gly Arg Ile Arg Asn Gly Ala Leu Leu Arg Val
                675                 680                 685

Tyr Val Pro Arg Ser Ser Leu Pro Gly Phe Tyr Arg Thr Ser Leu Thr
                690                 695                 700

Leu Ala Ala Pro Glu Ala Ala Gly Glu Val Glu Arg Leu Ile Gly His
705                 710                 715                 720

Pro Leu Pro Leu Arg Leu Asp Ala Ile Thr Gly Pro Glu Glu Glu Gly
                725                 730                 735

Gly Arg Leu Glu Thr Ile Leu Gly Trp Pro Leu Ala Glu Arg Thr Val
                740                 745                 750

Val Ile Pro Ser Ala Ile Pro Thr Asp Pro Arg Asn Val Gly Gly Asp
                755                 760                 765

Leu Asp Pro Ser Ser Ile Pro Asp Lys Glu Gln Ala Ile Ser Ala Leu
                770                 775                 780

Pro Asp Tyr Ala Ser Gln Pro Gly Lys Pro Pro Arg Glu Asp Leu Lys
785                 790                 795                 800

<210> SEQ ID NO 36
<211> LENGTH: 1353
<212> TYPE: DNA
<213> ORGANISM: Artificial sequence
<220> FEATURE:
<223> OTHER INFORMATION: Heavy chain FRP5 T366W:S354C (knob) coding
      sequence

<400> SEQUENCE: 36
atgcaggtac aactgcagca gtctggacct gaactgaaga agcctggaga gacagtcaag      60
atctcctgca aggcctctgg gtatcctttc acaaactatg gaatgaactg ggtgaagcag     120
gctccaggac agggtttaaa gtggatgggc tggattaaca cctccactgg agagtcaaca     180
tttgctgatg acttcaaggg acggtttgac ttctctttgg aaacctctgc aacactgcc      240 tatttgcaga tcaacaacct caaaagtgaa gacatggcta catatttctg tgcaagatgg     300
gaggtttacc acggctacgt tccttactgg ggccaaggga ccacggtcac cgtttcctct     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660

```
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcggaggga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020 aaagccaaag␣gcagccccg agaaccacag gtgtacaccc tgcccccatg ccgggaggag   1080
atgaccaaga accaggtcag cctgtggtgc ctggtcaaag␣cttctatcc cagcgacatc   1140 gccgtggagt gggagagcaa tgggcagccg gagaacaact acaagaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagcc tctccctgtc cccgggtaaa tga                                1353
```

<210> SEQ ID NO 37
<211> LENGTH: 450
<212> TYPE: PRT
<213> ORGANISM: Artificial sequence
<220> FEATURE:
<223> OTHER INFORMATION: Heavy chain FRP5 T366W:S354C (knob)

<400> SEQUENCE: 37

```
Met Gln Val Gln Leu Gln Gln Ser Gly Pro Glu Leu Lys Lys Pro Gly
1               5                   10                  15

Glu Thr Val Lys Ile Ser Cys Lys Ala Ser Gly Tyr Pro Phe Thr Asn
            20                  25                  30

Tyr Gly Met Asn Trp Val Lys Gln Ala Pro Gly Gln Gly Leu Lys Trp
        35                  40                  45

Met Gly Trp Ile Asn Thr Ser Thr Gly Glu Ser Thr Phe Ala Asp Asp
    50                  55                  60

Phe Lys Gly Arg Phe Asp Phe Ser Leu Glu Thr Ser Ala Asn Thr Ala
65                  70                  75                  80

Tyr Leu Gln Ile Asn Asn Leu Lys Ser Glu Asp Met Ala Thr Tyr Phe
                85                  90                  95

Cys Ala Arg Trp Glu Val Tyr His Gly Tyr Val Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255
Ser Arg Thr Pro Glu Val Thr Cys Val Val Asp Val Ser His Glu
        260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
            340                 345                 350
Thr Leu Pro Pro Cys Arg Glu Glu Met Thr Lys Asn Gln Val Ser Leu
        355                 360                 365
Trp Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Lys
    450

<210> SEQ ID NO 38
<211> LENGTH: 1353
<212> TYPE: DNA
<213> ORGANISM: Artificial sequence
<220> FEATURE:
<223> OTHER INFORMATION: Heavy chain FRP5 T366S:L368A:Y407V:Y349C (hole)
      coding sequence

<400> SEQUENCE: 38
atgcaggtac aactgcagca gtctggacct gaactgaaga agcctggaga gacagtcaag      60
atctcctgca aggcctctgg gtatccttc acaaactatg gaatgaactg ggtgaagcag     120
gctccaggac agggtttaaa gtggatgggc tggattaaca cctccactgg agagtcaaca     180
tttgctgatg acttcaaggg acggtttgac ttctctttgg aaacctctgc aacactgcc      240 tatttgcaga tcaacaacct caaaagtgaa gacatggcta catatttctg tgcaagatgg     300
gaggtttacc acggctacgt tccttactgg ggccaaggga ccacggtcac cgtttcctct     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctggggga      720 ccgtcagtct tcctcttccc cccaaaaccc aaggacaccc tcatgatctc ccggaccct      780
```

-continued

```
gaggtcacat gcgtggtggt ggacgtgagc cacgaagacc ctgaggtcaa gttcaactgg      840
tacgtggacg gcgtggaggt gcataatgcc aagacaaagc cgcgggagga gcagtacaac      900
agcacgtacc gtgtggtcag cgtcctcacc gtcctgcacc aggactggct gaatggcaag      960
gagtacaagt gcaaggtctc caacaaagcc ctcccagccc ccatcgagaa aaccatctcc     1020
aaagccaaag ggcagccccg agaaccacag gtgtgcaccc tgcccccatc ccgggaggag     1080
atgaccaaga accaggtcag cctgagctgc gcggtcaaag gcttctatcc cagcgacatc     1140
gccgtggagt gggagagcaa tgggcagccg gagaacaact acaagaccac gcctcccgtg     1200
ctggactccg acggctcctt cttcctcgtt agcaagctca ccgtggacaa gagcaggtgg     1260
cagcagggga acgtcttctc atgctccgtg atgcatgagg ctctgcacaa ccactacacg     1320
cagaagagcc tctccctgtc cccgggtaaa tga                                 1353
```

<210> SEQ ID NO 39
<211> LENGTH: 450
<212> TYPE: PRT
<213> ORGANISM: Artificial sequence
<220> FEATURE:
<223> OTHER INFORMATION: Heavy chain FRP5 T366S:L368A:Y407V:Y349C (hole)

<400> SEQUENCE: 39

```
Met Gln Val Gln Leu Gln Gln Ser Gly Pro Glu Leu Lys Lys Pro Gly
1               5                   10                  15

Glu Thr Val Lys Ile Ser Cys Lys Ala Ser Gly Tyr Pro Phe Thr Asn
            20                  25                  30

Tyr Gly Met Asn Trp Val Lys Gln Ala Pro Gly Gln Gly Leu Lys Trp
        35                  40                  45

Met Gly Trp Ile Asn Thr Ser Thr Gly Glu Ser Thr Phe Ala Asp Asp
    50                  55                  60

Phe Lys Gly Arg Phe Asp Phe Ser Leu Glu Thr Ser Ala Asn Thr Ala
65                  70                  75                  80

Tyr Leu Gln Ile Asn Asn Leu Lys Ser Glu Asp Met Ala Thr Tyr Phe
                85                  90                  95

Cys Ala Arg Trp Glu Val Tyr His Gly Tyr Val Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Cys
            340                 345                 350
Thr Leu Pro Pro Ser Arg Glu Glu Met Thr Lys Asn Gln Val Ser Leu
        355                 360                 365
Ser Cys Ala Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Val Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 40
<211> LENGTH: 1353
<212> TYPE: DNA
<213> ORGANISM: Artificial sequence
<220> FEATURE:
<223> OTHER INFORMATION: Heavy chain T427 T366W:S354C (knob) and
      A44C:C222A (Cys) coding sequence

<400> SEQUENCE: 40
atgcaggtcc aactgcagca gccggggact gaactggtga ggcctggagc ttcagtgaag      60
ctgtcctgca aggcttctgg cttctccttc accagttact ggatgaactg ggtgaagcag     120
aggcctggac aatgccttga gtggattggc atgattcatc cttccgatag tgaaactagg     180
ttaaatcaga agttcaagga cagggccaca ttgactgtag acaaatcctc cagcacagcc     240
tacatgcaac tcagcagccc gacatctgag gactctgcgg tctattactg tgcaagtgag     300
atggattatt actttgctat ggactactgg ggtcaaggaa cctcagtcac cgtctcctca     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatctgccg acaaaactca cacatgccca ccgtgcccag cacctgaact cctgggggga     720
ccgtcagtct tcctcttccc cccaaaaccc aaggacaccc tcatgatctc ccggaccct      780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
```

```
agcacgtacc gtgtggtcag cgtcctcacc gtcctgcacc aggactggct gaatggcaag        960
gagtacaagt gcaaggtctc caacaaagcc ctcccagccc ccatcgagaa aaccatctcc       1020
aaagccaaag gcagccccg agaaccacag gtgtacaccc tgccccccatg ccggggaggag      1080 atgaccaaga accaggtcag cctgtggtgc ctggtcaaag gcttctatcc cagcgacatc      1140
gccgtggagt gggagagcaa tgggcagccg gagaacaact acaagaccac gcctcccgtg       1200
ctggactccg acggctcctt cttcctctat agcaagctca ccgtggacaa gagcaggtgg       1260
cagcagggga acgtcttctc atgctccgtg atgcatgagg ctctgcacaa ccactacacg       1320
cagaagagcc tctccctgtc cccgggtaaa tga                                    1353
```

<210> SEQ ID NO 41
<211> LENGTH: 450
<212> TYPE: PRT
<213> ORGANISM: Artificial sequence
<220> FEATURE:
<223> OTHER INFORMATION: Heavy chain T427 T366W:S354C (knob) and
      A44C:C222A (Cys)

<400> SEQUENCE: 41

```
Met Gln Val Gln Leu Gln Gln Pro Gly Thr Glu Leu Val Arg Pro Gly
1               5                   10                  15

Ala Ser Val Lys Leu Ser Cys Lys Ala Ser Gly Phe Ser Phe Thr Ser
            20                  25                  30

Tyr Trp Met Asn Trp Val Lys Gln Arg Pro Gly Gln Cys Leu Glu Trp
        35                  40                  45

Ile Gly Met Ile His Pro Ser Asp Ser Glu Thr Arg Leu Asn Gln Lys
    50                  55                  60

Phe Lys Asp Arg Ala Thr Leu Thr Val Asp Lys Ser Ser Ser Thr Ala
65                  70                  75                  80

Tyr Met Gln Leu Ser Ser Pro Thr Ser Glu Asp Ser Ala Val Tyr Tyr
                85                  90                  95

Cys Ala Ser Glu Met Asp Tyr Tyr Phe Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Ala Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Glu Glu Met Thr Lys Asn Gln Val Ser Leu
        355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 42
<211> LENGTH: 216
<212> TYPE: PRT
<213> ORGANISM: Pseudomonas aeruginosa

<400> SEQUENCE: 42

Ala Glu Phe Leu Gly Asp Gly Gly Asp Val Ser Phe Ser Thr Arg Gly
1               5                   10                  15

Thr Gln Asn Trp Thr Val Glu Arg Leu Leu Gln Ala His Arg Gln Leu
            20                  25                  30

Glu Glu Arg Gly Tyr Val Phe Val Gly Tyr His Gly Thr Phe Leu Glu
        35                  40                  45

Ala Ala Gln Ser Ile Val Phe Gly Gly Val Arg Ala Arg Ser Gln Asp
    50                  55                  60

Leu Asp Ala Ile Trp Arg Gly Phe Tyr Ile Ala Gly Asp Pro Ala Leu
65                  70                  75                  80

Ala Tyr Gly Tyr Ala Gln Asp Gln Glu Pro Asp Ala Arg Gly Arg Ile
                85                  90                  95

Arg Asn Gly Ala Leu Leu Arg Val Tyr Val Pro Arg Ser Ser Leu Pro
            100                 105                 110

Gly Phe Tyr Arg Thr Gly Leu Thr Leu Ala Ala Pro Glu Ala Ala Gly
        115                 120                 125

Glu Val Glu Arg Leu Ile Gly His Pro Leu Pro Leu Arg Leu Asp Ala
    130                 135                 140

Ile Thr Gly Pro Glu Glu Glu Gly Gly Arg Leu Glu Thr Ile Leu Gly
145                 150                 155                 160

Trp Pro Leu Ala Glu Arg Thr Val Val Ile Pro Ser Ala Ile Pro Thr
                165                 170                 175

Asp Pro Arg Asn Val Gly Gly Asp Leu Ala Pro Ser Ser Ile Pro Asp
            180                 185                 190
```

```
Gln Glu Gln Ala Ile Ser Ala Leu Pro Asp Tyr Ala Ser Gln Pro Gly
        195                 200                 205

Lys Pro Ser Arg Glu Asp Leu Lys
    210                 215

<210> SEQ ID NO 43
<211> LENGTH: 536
<212> TYPE: PRT
<213> ORGANISM: Corynebacterium diphtheriae

<400> SEQUENCE: 43

Met Gly Ala Asp Asp Val Val Asp Ser Lys Ser Phe Val Met Glu
1               5                   10                  15

Asn Phe Ser Ser Tyr His Gly Thr Lys Pro Gly Tyr Val Asp Ser Ile
                20                  25                  30

Gln Lys Gly Ile Gln Lys Pro Lys Ser Gly Thr Gln Gly Asn Tyr Asp
            35                  40                  45

Asp Asp Trp Lys Gly Phe Tyr Ser Thr Asp Asn Lys Tyr Asp Ala Ala
        50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
```

```
              340                 345                 350
Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
370                 375                 380

His Lys Thr Gln Pro Phe Leu His Asp Gly Tyr Ala Val Ser Trp Asn
385                 390                 395                 400

Thr Val Glu Asp Ser Ile Ile Arg Thr Gly Phe Gln Gly Glu Ser Gly
                405                 410                 415

His Asp Ile Lys Ile Thr Ala Glu Asn Thr Pro Leu Pro Ile Ala Gly
            420                 425                 430

Val Leu Leu Pro Thr Ile Pro Gly Lys Leu Asp Val Asn Lys Ser Lys
        435                 440                 445

Thr His Ile Ser Val Asn Gly Arg Lys Ile Arg Met Arg Cys Arg Ala
    450                 455                 460

Ile Asp Gly Asp Val Thr Phe Cys Arg Pro Lys Ser Pro Val Tyr Val
465                 470                 475                 480

Gly Asn Gly Val His Ala Asn Leu His Val Ala Phe His Arg Ser Ser
                485                 490                 495

Ser Glu Lys Ile His Ser Asn Glu Ile Ser Ser Asp Ser Ile Gly Val
            500                 505                 510

Leu Gly Tyr Gln Lys Thr Val Asp His Thr Lys Val Asn Ser Lys Leu
        515                 520                 525

Ser Leu Phe Phe Glu Ile Lys Ser
    530                 535

<210> SEQ ID NO 44
<211> LENGTH: 127
<212> TYPE: PRT
<213> ORGANISM: Artificial sequence
<220> FEATURE:
<223> OTHER INFORMATION: interleukin 2

<400> SEQUENCE: 44

Thr Lys Lys Thr Gln Leu Gln Leu Glu His Leu Leu Leu Asp Leu Gln
1               5                   10                  15

Met Ile Leu Asn Gly Ile Asn Asn Tyr Lys Asn Pro Lys Leu Thr Arg
            20                  25                  30

Met Leu Thr Phe Lys Phe Tyr Met Pro Lys Lys Ala Thr Glu Leu Lys
        35                  40                  45

His Leu Gln Cys Leu Glu Glu Glu Leu Lys Pro Leu Glu Glu Val Leu
    50                  55                  60

Asn Leu Ala Gln Ser Lys Asn Phe His Leu Arg Pro Arg Asp Leu Ile
65                  70                  75                  80

Ser Asn Ile Asn Val Ile Val Leu Glu Leu Lys Gly Ser Glu Thr Thr
                85                  90                  95

Phe Met Cys Glu Tyr Ala Asp Glu Thr Ala Thr Ile Val Glu Phe Leu
            100                 105                 110

Asn Arg Trp Ile Thr Phe Cys Gln Ser Ile Ile Ser Thr Leu Thr
        115                 120                 125

<210> SEQ ID NO 45
<211> LENGTH: 207
<212> TYPE: PRT
<213> ORGANISM: Homo sapiens

<400> SEQUENCE: 45
```

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Ile Thr
            20                  25                  30

Gln Thr Pro Tyr Lys Val Ser Ile Ser Gly Thr Thr Val Ile Leu Thr
            35                  40                  45

Cys Pro Gln Tyr Pro Gly Ser Glu Ile Leu Trp Gln His Asn Asp Lys
50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
            115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
            195                 200                 205

<210> SEQ ID NO 46
<211> LENGTH: 290
<212> TYPE: PRT
<213> ORGANISM: Homo sapiens

<400> SEQUENCE: 46

Met Gly Gly Gly Ala Gly Glu Arg Leu Phe Thr Ser Ser Cys Leu Val
1               5                   10                  15

Gly Leu Val Pro Leu Gly Leu Arg Ile Ser Leu Val Thr Cys Pro Leu
            20                  25                  30

Gln Cys Gly Ile Met Trp Gln Leu Leu Pro Thr Ala Leu Leu Leu
            35                  40                  45

Leu Val Ser Ala Gly Met Arg Thr Glu Asp Leu Pro Lys Ala Val Val
50                  55                  60

Phe Leu Glu Pro Gln Trp Tyr Arg Val Leu Lys Asp Ser Val Thr
65                  70                  75                  80

Leu Lys Cys Gln Gly Ala Tyr Ser Pro Glu Asp Asn Ser Thr Gln Trp
                85                  90                  95

Phe His Asn Glu Ser Leu Ile Ser Ser Gln Ala Ser Ser Tyr Phe Ile
                100                 105                 110

Asp Ala Ala Thr Val Asp Asp Ser Gly Glu Tyr Arg Cys Gln Thr Asn
            115                 120                 125

Leu Ser Thr Leu Ser Asp Pro Val Gln Leu Glu Val His Ile Gly Trp
130                 135                 140

Leu Leu Leu Gln Ala Pro Arg Trp Val Phe Lys Glu Glu Asp Pro Ile
145                 150                 155                 160

His Leu Arg Cys His Ser Trp Lys Asn Thr Ala Leu His Lys Val Thr 165                 170                 175
Tyr Leu Gln Asn Gly Lys Gly Arg Lys Tyr Phe His His Asn Ser Asp
                 180                 185                 190

Phe Tyr Ile Pro Lys Ala Thr Leu Lys Asp Ser Gly Ser Tyr Phe Cys
            195                 200                 205

Arg Gly Leu Phe Gly Ser Lys Asn Val Ser Ser Glu Thr Val Asn Ile
        210                 215                 220

Thr Ile Thr Gln Gly Leu Ala Val Ser Thr Ile Ser Ser Phe Phe Pro
225                 230                 235                 240

Pro Gly Tyr Gln Val Ser Phe Cys Leu Val Met Val Leu Leu Phe Ala
                245                 250                 255

Val Asp Thr Gly Leu Tyr Phe Ser Val Lys Thr Asn Ile Arg Ser Ser
            260                 265                 270

Thr Arg Asp Trp Lys Asp His Lys Phe Lys Trp Arg Lys Asp Pro Gln
        275                 280                 285

Asp Lys
    290

<210> SEQ ID NO 47
<211> LENGTH: 153
<212> TYPE: PRT
<213> ORGANISM: Homo sapiens

<400> SEQUENCE: 47

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150

<210> SEQ ID NO 48
<211> LENGTH: 365
<212> TYPE: PRT
<213> ORGANISM: Homo sapiens

<400> SEQUENCE: 48

Met Ala Val Met Ala Pro Arg Thr Leu Val Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala

```
            35                  40                  45
Val Gly Tyr Val Asp Asp Thr Gln Phe Val Arg Phe Asp Ser Asp Ala
     50                  55                  60

Ala Ser Gln Arg Met Glu Pro Arg Ala Pro Trp Ile Glu Gln Glu Gly
 65                  70                  75                  80

Pro Glu Tyr Trp Asp Gly Glu Thr Arg Lys Val Lys Ala His Ser Gln
                 85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
        355                 360                 365

<210> SEQ ID NO 49
<211> LENGTH: 178
<212> TYPE: PRT
<213> ORGANISM: Homo sapiens

<400> SEQUENCE: 49

Met His Ser Ser Ala Leu Leu Cys Cys Leu Val Leu Leu Thr Gly Val
 1               5                  10                  15

Arg Ala Ser Pro Gly Gln Gly Thr Gln Ser Glu Asn Ser Cys Thr His
                20                  25                  30

Phe Pro Gly Asn Leu Pro Asn Met Leu Arg Asp Leu Arg Asp Ala Phe
            35                  40                  45
```

Ser Arg Val Lys Thr Phe Phe Gln Met Lys Asp Gln Leu Asp Asn Leu
50 55 60

Leu Leu Lys Glu Ser Leu Leu Glu Asp Phe Lys Gly Tyr Leu Gly Cys
65 70 75 80

Gln Ala Leu Ser Glu Met Ile Gln Phe Tyr Leu Glu Glu Val Met Pro
85 90 95

Gln Ala Glu Asn Gln Asp Pro Asp Ile Lys Ala His Val Asn Ser Leu
100 105 110

Gly Glu Asn Leu Lys Thr Leu Arg Leu Arg Leu Arg Arg Cys His Arg
115 120 125

Phe Leu Pro Cys Glu Asn Lys Ser Lys Ala Val Glu Gln Val Lys Asn
130 135 140

Ala Phe Asn Lys Leu Gln Glu Lys Gly Ile Tyr Lys Ala Met Ser Glu
145 150 155 160

Phe Asp Ile Phe Ile Asn Tyr Ile Glu Ala Tyr Met Thr Met Lys Ile
165 170 175

Arg Asn

<210> SEQ ID NO 50
<211> LENGTH: 576
<212> TYPE: PRT
<213> ORGANISM: Ricinus communis

<400> SEQUENCE: 50

Met Lys Pro Gly Gly Asn Thr Ile Val Ile Trp Met Tyr Ala Val Ala
1 5 10 15

Thr Trp Leu Cys Phe Gly Ser Thr Ser Gly Trp Ser Phe Thr Leu Glu
20 25 30

Asp Asn Asn Ile Phe Pro Lys Gln Tyr Pro Ile Ile Asn Phe Thr Thr
35 40 45

Ala Gly Ala Thr Val Gln Ser Tyr Thr Asn Phe Ile Arg Ala Val Arg
50 55 60

Gly Arg Leu Thr Thr Gly Ala Asp Val Arg His Glu Ile Pro Val Leu
65 70 75 80

Pro Asn Arg Val Gly Leu Pro Ile Asn Gln Arg Phe Ile Leu Val Glu
85 90 95

Leu Ser Asn His Ala Glu Leu Ser Val Thr Leu Ala Leu Asp Val Thr
100 105 110

Asn Ala Tyr Val Val Gly Tyr Arg Ala Gly Asn Ser Ala Tyr Phe Phe
115 120 125

His Pro Asp Asn Gln Glu Asp Ala Glu Ala Ile Thr His Leu Phe Thr
130 135 140

Asp Val Gln Asn Arg Tyr Thr Phe Ala Phe Gly Gly Asn Tyr Asp Arg
145 150 155 160

Leu Glu Gln Leu Ala Gly Asn Leu Arg Glu Asn Ile Glu Leu Gly Asn
165 170 175

Gly Pro Leu Glu Glu Ala Ile Ser Ala Leu Tyr Tyr Tyr Ser Thr Gly
180 185 190

Gly Thr Gln Leu Pro Thr Leu Ala Arg Ser Phe Ile Ile Cys Ile Gln
195 200 205

Met Ile Ser Glu Ala Ala Arg Phe Gln Tyr Ile Glu Gly Glu Met Arg
210 215 220

Thr Arg Ile Arg Tyr Asn Arg Arg Ser Ala Pro Asp Pro Ser Val Ile
225 230 235 240

```
Thr Leu Glu Asn Ser Trp Gly Arg Leu Ser Thr Ala Ile Gln Glu Ser
                245                 250                 255

Asn Gln Gly Ala Phe Ala Ser Pro Ile Gln Leu Gln Arg Arg Asn Gly
            260                 265                 270

Ser Lys Phe Ser Val Tyr Asp Val Ser Ile Leu Ile Pro Ile Ile Ala
        275                 280                 285

Leu Met Val Tyr Arg Cys Ala Pro Pro Ser Ser Gln Phe Ser Leu
    290                 295                 300

Leu Ile Arg Pro Val Val Pro Asn Phe Asn Ala Asp Val Cys Met Asp
305                 310                 315                 320

Pro Glu Pro Ile Val Arg Ile Val Gly Arg Asn Gly Leu Cys Val Asp
                325                 330                 335

Val Arg Asp Gly Arg Phe His Asn Gly Asn Ala Ile Gln Leu Trp Pro
            340                 345                 350

Cys Lys Ser Asn Thr Asp Ala Asn Gln Leu Trp Thr Leu Lys Arg Asp
        355                 360                 365

Asn Thr Ile Arg Ser Asn Gly Lys Cys Leu Thr Thr Tyr Gly Tyr Ser
    370                 375                 380

Pro Gly Val Tyr Val Met Ile Tyr Asp Cys Asn Thr Ala Ala Thr Asp
385                 390                 395                 400

Ala Thr Arg Trp Gln Ile Trp Asp Asn Gly Thr Ile Ile Asn Pro Arg
                405                 410                 415

Ser Ser Leu Val Leu Ala Ala Thr Ser Gly Asn Ser Gly Thr Thr Leu
            420                 425                 430

Thr Val Gln Thr Asn Ile Tyr Ala Val Ser Gln Gly Trp Leu Pro Thr
        435                 440                 445

Asn Asn Thr Gln Pro Phe Val Thr Thr Ile Val Gly Leu Tyr Gly Leu
    450                 455                 460

Cys Leu Gln Ala Asn Ser Gly Gln Val Trp Ile Glu Asp Cys Ser Ser
465                 470                 475                 480

Glu Lys Ala Glu Gln Trp Ala Leu Tyr Ala Asp Gly Ser Ile Arg
                485                 490                 495

Pro Gln Gln Asn Arg Asp Asn Cys Leu Thr Ser Asp Ser Asn Ile Arg
            500                 505                 510

Glu Thr Val Val Lys Ile Leu Ser Cys Gly Pro Ala Ser Ser Gly Gln
        515                 520                 525

Arg Trp Met Phe Lys Asn Asp Gly Thr Ile Leu Asn Leu Tyr Ser Gly
    530                 535                 540

Leu Val Leu Asp Val Arg Ala Ser Asp Pro Ser Leu Lys Gln Ile Ile
545                 550                 555                 560

Leu Tyr Pro Leu His Gly Asp Pro Asn Gln Ile Trp Leu Pro Leu Phe
                565                 570                 575

<210> SEQ ID NO 51
<211> LENGTH: 651
<212> TYPE: DNA
<213> ORGANISM: Pseudomonas aeruginosa

<400> SEQUENCE: 51
gcggagttcc tcggcgacgg cggcgacgtc agcttcagca cccgcggcac gcagaactgg    60
acggtggagc ggctgctcca ggcgcaccgc caactggagg agcgcggcta tgtgttcgtc   120
ggctaccacg gcaccttcct cgaagcggcg caaagcatcg tcttcggcgg ggtgcgcgcg   180
cgcagccagg accttgacgc gatctggcgc ggtttctata tcgccggcga tccggcgctg   240
```

```
gcctacggct acgcccagga ccaggaaccc gacgcgcgcg gccggatccg caacggtgcc    300
ctgctgcggg tctatgtgcc gcgctcgagt ctgccgggct tctaccgcac cggcctgacc    360
ctggccgcgc cggaggcggc gggcgaggtc gaacggctga tcggccatcc gctgccgctg    420
cgcctggacg ccatcaccgg ccccgaggag gaaggcgggc gcctggagac cattctcggc    480
tggccgctgg ccgagcgcac cgtggtgatt ccctcggcga tccccaccga cccacgcaac    540
gtcggcggcg acctcgcccc gtccagcatc cccgaccagg aacaggcgat cagcgccctg    600
ccggactacg ccagccagcc cggcaaaccg tcgcgcgagg acctgaagta a             651
```

<210> SEQ ID NO 52
<211> LENGTH: 1611
<212> TYPE: DNA
<213> ORGANISM: Corynebacterium diphtheriae

<400> SEQUENCE: 52
atgggcgctg atgatgttgt tgattcttct aaatcttttg tgatggaaaa cttttcttcg 60
taccacggga ctaaacctgg ttatgtagat tccattcaaa aaggtataca aaagccaaaa 120
tctggtacac aaggaaatta tgacgatgat tggaaagggt tttatagtac cgacaataaa 180
tacgacgctg cgggatactc tgtagataat gaaaacccgc tctctggaaa agctggaggc 240
gtggtcaaag tgacgtatcc aggactgacg aaggttctcg cactaaaagt ggataatgcc 300
gaaactatta agaaagagtt aggtttaagt ctcactgaac cgttgatgga gcaagtcgga 360
acggaagagt ttatcaaaag gttcggtgat ggtgcttcgc gtgtagtgct cagccttccc 420
ttcgctgagg ggagttctag cgttgaatat attaataact gggaacaggc gaaagcgtta 480
agcgtagaac ttgagattaa ttttgaaacc cgtggaaaac gtggccaaga tgcgatgtat 540
gagtatatgg ctcaagcctg tgcaggaaat cgtgtcaggc gatcagtagg tagctcattg 600
tcatgcataa atcttgattg ggatgtcata agggataaaa ctaagacaaa gatagagtct 660
ttgaaagagc atggccctat caaaaataaa atgagcgaaa gtcccaataa aacagtatct 720
gaggaaaaag ctaaacaata cctagaagaa tttcatcaaa cggcattaga gcatcctgaa 780
ttgtcagaac ttaaaaccgt tactgggacc aatcctgtat tcgctggggc taactatgcg 840
gcgtgggcag taaacgttgc gcaagttatc gatagcgaaa cagctgataa tttggaaaag 900
acaactgctg ctctttcgat acttcctggt atcggtagcg taatgggcat tgcagacggt 960
gccgttcacc acaatacaga agagatagtg gcacaatcaa tagctttatc atctttaatg 1020
gttgctcaag ctattccatt ggtaggagag ctagttgata ttggtttcgc tgcatataat 1080
tttgtagaga gtattatcaa tttatttcaa gtagttcata attcgtataa tcgtcccgcg 1140
tattctccgg ggcataaaac gcaaccattt cttcatgacg ggtatgctgt cagttggaac 1200
actgttgaag attcgataat ccgaactggt tttcaagggg agagtgggca cgacataaaa 1260
attactgctg aaaatacccc gcttccaatc gcgggtgtcc tactaccgac tattcctgga 1320
aagctggacg ttaataagtc caagactcat atttccgtaa atggtcggaa aataaggatg 1380
cgttgcagag ctatagacgg tgatgtaact tttgtcgcc ctaaatctcc tgtttatgtt 1440
ggtaatggtg tgcatgcgaa tcttcacgtg gcatttcaca gaagcagctc ggagaaaatt 1500
cattctaatg aaatttcatc ggattccata ggcgttcttg ggtaccagaa aacagtagat 1560
cacaccaagg ttaattctaa gctatcgcta ttttttgaaa tcaaaagctg a 1611

<210> SEQ ID NO 53
<211> LENGTH: 698

```
<212> TYPE: DNA
<213> ORGANISM: Artificial sequence
<220> FEATURE:
<223> OTHER INFORMATION: interleukin 2
<220> FEATURE:
<221> NAME/KEY: misc_feature
<222> LOCATION: (4)..(4)
<223> OTHER INFORMATION: n is a, c, g, or t

<400> SEQUENCE: 53 gggngggga caaagaaaac acagctacaa ctggagcatt tacttctgga tttacagatg      60
attttgaatg gaattaataa ttacaagaat cccaaactca ccaggatgct cacatttaag    120
ttttacatgc ccaagaaggc cacagaactg aaacatcttc agtgtctaga agaagaactc    180
aaacctctgg aggaagtgct aaatttagct caaagcaaaa actttcactt aagacccagg    240
gacttaatca gcaatatcaa cgtaatagtt ctggaactaa agggatctga acaacattc     300
atgtgtgaat atgctgatga cagcaacc attgtagaat ttctgaacag atggattacc     360
ttttgtcaaa gcatcatctc aacactgact tgataattaa gtgcttccca cttaaaacat    420
atcaggcctt ctatttattt aaatatttaa attttatatt tattgttgaa tgtatggttt    480
gctacctatt gtaactatta ttcttaatct taaaactata aatatggatc ttttatgatt    540
cttttgtaa gccctagggg ctctaaaatg gtttcactta tttatcccaa aatatttatt     600
attatgttga atgttaaata tagtatctat gtagattggt tagtaaaact atttaataaa   660
tttgataaat ataaacaaaa aaaaaaaaac cccccccc                           698

<210> SEQ ID NO 54
<211> LENGTH: 1311
<212> TYPE: DNA
<213> ORGANISM: Homo sapiens

<400> SEQUENCE: 54
gtaagtctgc tggcctccgc catcttagta aagtaacagt cccatgaaac aaagatgcag     60
tcgggcactc actggagagt tctgggcctc tgcctcttat cagttggcgt ttgggggcaa    120
gatggtaatg aagaaatggg tggtattaca cagacaccat ataaagtctc catctctgga   180
accacagtaa tattgacatg ccctcagtat cctggatctg aaatactatg caacacaat    240
gataaaaaca taggcggtga tgaggatgat aaaaacatag gcagtgatga ggatcacctg    300
tcactgaagg aattttcaga attggagcaa agtggttatt atgtctgcta ccccagagga   360
agcaaaccag aagatgcgaa cttttatctc tacctgaggg caagagtgtg tgagaactgc    420
atggagatgt atgtgatgtc ggtggccaca attgtcatag tggacatctg catcactggg   480
ggcttgctgc tgctggttta ctactggagc aagaatagaa aggccaaggc caagcctgtg   540
acacgaggag cgggtgctgg cggcaggcaa agggacaaa acaaggagag gccaccacct   600
gttcccaacc cagactatga gcccatccgg aaaggccagc gggacctgta ttctggcctg   660
aatcagagac gcatctgacc ctctggagaa cactgcctcc gctggccca ggtctcctct    720
ccagtccccc tgcgactccc tgtttcctgg gctagtcttg accccacga gagagaatcg    780
ttcctcagcc tcatggtgaa ctcgcgccct ccagcctgat ccccgctcc ctcctccctg    840
ccttctctgc tggtacccag tcctaaaata ttgctgcttc ctcttccttt gaagcatcat    900
cagtagtcac accctcacag ctggcctgcc ctcttgccag gatatttatt tgtgctattc    960
actcccttcc ctttggatgt aacttctccg ttcagttccc tccttttctt gcatgtaagt   1020
tgtcccccat cccaaagtat tccatctact tttctatcgc cgtcccctttt tgcagccctc   1080
```

| | |
|---|---|
| tctggggatg gactgggtaa atgttgacag aggccctgcc ccgttcacag atcctggccc | 1140 |
| tgagccagcc ctgtgctcct ccctccccca acactcccta ccaaccccct aatcccctac | 1200 |
| tccctccaac cccccctccc actgtaggcc actggatggt catttggcat ctccgtatat | 1260 |
| gtgctctggc tcctcagctg agagagaaaa aaataaactg tatttggctg c | 1311 |

```
<210> SEQ ID NO 55
<211> LENGTH: 2406
<212> TYPE: DNA
<213> ORGANISM: Homo sapiens

<400> SEQUENCE: 55
```

| | |
|---|---|
| gattctgtgt gtgtcctcag atgctcagcc acagaccttt gagggagtaa aggggcaga | 60 |
| cccacccacc ttgcctccag gctctttcct tcctggtcct gttctatggt ggggctccct | 120 |
| tgccagactt cagactgaga agtcagatga agtttcaaga aaaggaaatt ggtgggtgac | 180 |
| agagatgggt ggaggggctg ggaaaaggct gtttacttcc tcctgtctag tcggtttggt | 240 |
| ccctttaggg ctccggatat cctttggtgac ttgtccactc cagtgtggca tcatgtggca | 300 |
| gctgctcctc ccaactgctc tgctacttct agtttcagct ggcatgcgga ctgaagatct | 360 |
| cccaaaggct gtggtgttcc tggagcctca atggtacagg gtgctcgaga aggacagtgt | 420 |
| gactctgaag tgccagggag cctactcccc tgaggacaat tccacacagt ggtttcacaa | 480 |
| tgagagcctc atctcaagcc aggcctcgag ctacttcatt gacgctgcca cagtcgacga | 540 |
| cagtggagag tacaggtgcc agacaaacct ctccaccctc agtgacccgg tgcagctaga | 600 |
| agtccatatc ggctggctgt tgctccaggc ccctcgtggg gtgttcaagg aggagaccc | 660 |
| tattcacctg aggtgtcaca gctggaagaa cactgctctg cataaggtca catatttaca | 720 |
| gaatggcaaa gcaggaagt attttcatca taattctgac ttctacattc aaaagccac | 780 |
| actcaaagac agcggctcct acttctgcag ggggctttt gggagtaaaa atgtgtcttc | 840 |
| agagactgtg aacatcacca tcactcaagg tttggcagtg tcaaccatct catcattctt | 900 |
| tccacctggg taccaagtct ctttctgctt ggtgatggta ctccttttg cagtggacac | 960 |
| aggactatat ttctctgtga agacaaacat tcgaagctca acaagagact ggaaggacca | 1020 |
| taaatttaaa tggagaaagg accctcaaga caaatgaccc ccatcccatg ggggtaataa | 1080 |
| gagcagtagc agcagcatct ctgaacattt ctctggattt gcaaccccat catcctcagg | 1140 |
| cctctctaca agcagcagga acatagaac tcagagccag atcccttatc caactctcga | 1200 |
| cttttccttg gtctccagtg aagggaaaa gcccatgatc ttcaagcagg gaagccccag | 1260 |
| tgagtagctg cattcctaga aattgaagtt tcagagctac acaaacactt tttctgtccc | 1320 |
| aaccgttccc tcacagcaaa gcaacaatac aggctaggga tggtaatcct ttaaacatac | 1380 |
| aaaaattgct cgtgttataa attacccagt ttagagggga aaaaaaaaca attattccta | 1440 |
| aataaatgga taagtagaat taatggttga ggcaggacca tacagagtgt gggaactgct | 1500 |
| ggggatctag ggaattcagt gggaccaatg aaagcatggc tgagaaatag caggtagtcc | 1560 |
| aggatagtct aagggaggtg ttcccatctg agcccagaga taagggtgtc ttcctagaac | 1620 |
| attagccgta gtggaattaa caggaaatca tgagggtgac gtagaattga gtcttccagg | 1680 |
| ggactctatc agaactggac catctccaag tatataacga tgagtcctct taatgctagg | 1740 |
| agtagaaaat ggtcctagga aggggactga ggattgcggt gggggggtggg gtggaaaaga | 1800 |
| aagtacagaa caaaccctgt gtcactgtcc caagttgcta agtgaacaga actatctcag | 1860 |
| catcagaatg agaaagcctg agaagaaaga accaaccaca agcacacagg aaggaaagcg | 1920 |

-continued

```
caggaggtga aaatgctttc ttggccaggg tagtaagaat tagaggttaa tgcagggact   1980
gtaaaaccac cttttctgct tcaatatcta attcctgtgt agctttgttc attgcattta   2040
ttaaacaaat gttgtataac caatactaaa tgtactactg agcttcgctg agttaagtta   2100
tgaaactttc aaatccttca tcatgtcagt tccaatgagg tggggatgga gaagacaatt   2160
gttgcttatg aaagaaagct ttagctgtct ctgttttgta agctttaagc gcaacatttc   2220
ttggttccaa taaagcattt tacaagatct tgcatgctac tcttagatag aagatgggaa   2280
aaccatggta ataaaatatg aatgataaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaa                                                             2406

<210> SEQ ID NO 56
<211> LENGTH: 921
<212> TYPE: DNA
<213> ORGANISM: Homo sapiens

<400> SEQUENCE: 56
ttctatgcaa agcaaaaagc cagcagcagc cccaagctga taagattaat ctaaagagca     60
aattatggtg taatttccta tgctgaaact ttgtagttaa ttttttaaaa aggtttcatt    120
ttcctattgg tctgatttca caggaacatt ttacctgttt gtgaggcatt ttttctcctg    180
gaagagaggt gctgattggc cccaagtgac tgacaatctg gtgtaacgaa aatttccaat    240
gtaaactcat tttccctcgg tttcagcaat tttaaatcta tatatagaga tatctttgtc    300
agcattgcat cgttagcttc tcctgataaa ctaattgcct cacattgtca ctgcaaatcg    360
acacctatta atgggtctca cctcccaact gcttccccct ctgttcttcc tgctagcatg    420
tgccggcaac tttgtccacg gacacaagtg cgatatcacc ttacaggaga tcatcaaaac    480
tttgaacagc ctcacagagc agaagactct gtgcaccgag ttgaccgtaa cagacatctt    540
tgctgcctcc aagaacacaa ctgagaagga aaccttctgc agggctgcga ctgtgctccg    600
gcagttctac agccaccatg agaaggacac tcgctgcctg ggtgcgactg cacagcagtt    660
ccacaggcac aagcagctga tccgattcct gaaacggctc gacaggaacc tctgggggcct    720 ggcgggcttg aattcctgtc ctgtgaagga agccaaccag agtacgttgg aaaacttctt    780
ggaaaggcta aagacgatca tgagagagaa atattcaaag tgttcgagct gaatatttta    840
atttatgagt ttttgatagc tttattttt aagtatttat atatttataa ctcatcataa    900
aataaagtat atatagaatc t                                              921

<210> SEQ ID NO 57
<211> LENGTH: 4000
<212> TYPE: DNA
<213> ORGANISM: Homo sapiens

<400> SEQUENCE: 57
aagcttactc tctggcacca aactccatgg gatgattttt ccttcctaga agagtccagg     60
tggacaggta aggagtggga gtcagggagt ccagttccag ggacagagat tacgggataa    120
aaagtgaaag gagagggacg gggcccatgc cgagggtttc tcccttgttt ctcagacagc    180
tcttgggcca agactcaggg agacattgag acagagcgct tggcacagaa gcagaggggt    240
cagggcgaag tccagggccc caggcgttgg ctctcagggt ctcaggcccc gaaggcggtg    300
tatggattgg ggagtcccag ccttggggat tccccaactc cgcagtttct tttctccctc    360
```

| | |
|---|---|
| tcccaaccta tgtagggtcc ttcttcctgg atactcacga cgcggaccca gttctcactc | 420 |
| ccattgggtg tcgggtttcc agagaagcca atcagtgtcg tcgcggtcgc ggttctaaag | 480 |
| tccgcacgca cccaccggga ctcagattct ccccagacgc cgaggatggc cgtcatggcg | 540 |
| ccccgaaccc tcgtcctgct actctcgggg gctctggccc tgacccagac ctgggcgggt | 600 |
| gagtgcgggg tcgggaggga aacggcctct gtggggagaa gcaacgggcc gcctggcggg | 660 |
| ggcgcaggac ccgggaagcc gcgccgggag gagggtcggg cgggtctcag ccactcctcg | 720 |
| tccccaggct ctcactccat gaggtatttc ttcacatccg tgtcccggcc cggccgcggg | 780 |
| gagccccgct tcatcgcagt gggctacgtg gacgacacgc agttcgtgcg gttcgacagc | 840 |
| gacgccgcga gccagaggat ggagccgcgg gcgccgtgga tagagcagga gggtccggag | 900 |
| tattgggacg gggagacacg gaaagtgaag gcccactcac agactcaccg agtggacctg | 960 |
| gggaccctgc gcggctacta caaccagagc gaggccggtg agtgaccccg gcccggggcg | 1020 |
| caggtcacga cctctcatcc cccacgacg ggccaggtcg cccacagtct ccgggtccga | 1080 |
| gatccgcccc gaagccgcgg gaccccgaga cccttgcccc gggagaggcc caggcgcctt | 1140 |
| tacccggttt cattttcagt ttaggccaaa aatcccccca ggttggtcgg ggcggggcgg | 1200 |
| ggctcggggg accgggctga ccgcggggtc cgggccaggt tctcacaccg tccagaggat | 1260 |
| gtatggctgc gacgtggggt cggactggcg cttcctccgc gggtaccacc agtacgccta | 1320 |
| cgacggcaag gattacatcg ccctgaaaga ggacctgcgc tcttggaccg cggcggacat | 1380 |
| ggcagctcag accaccaagc acaagtggga ggcggcccat gtggcggagc agttgagagc | 1440 |
| ctacctggag ggcacgtgcg tggagtggct ccgcagatac ctggagaacg ggaaggagac | 1500 |
| gctgcagcgc acgggtacca ggggccacgg ggcgcctccc tgatcgcctg tagatctccc | 1560 |
| gggctggcct cccacaagga ggggagacaa ttgggaccaa cactagaata tcgccctccc | 1620 |
| tctggtcctg agggagagga atcctcctgg gtttccagat cctgtaccag agagtgactc | 1680 |
| tgaggttccg ccctgctctc tgacacaatt aagggataaa atctctgaag gaatgacggg | 1740 |
| aagacgatcc ctcgaatact gatgagtggt ccctttgac acacacaggc agcagccttg | 1800 |
| ggcccgtgac ttttcctctc aggccttgtt ctctgcttca cactcaatgt gtgtgggggt | 1860 |
| ctgagtccag cacttctgag tccttcagcc tccactcagg tcaggaccag aagtcgctgt | 1920 |
| tccctcttca gggactagaa tttccacgga ataggagatt atcccaggtg cctgtgtcca | 1980 |
| ggctggtgtc tgggttctgt gctcccttcc ccatcccagg tgtcctgtcc attctcaaga | 2040 |
| tagccacatg tgtgctggag gagtgtccca tgacagatcg aaaatgcctg aatgatctga | 2100 |
| ctcttcctga cagacgcccc caaaacgcat atgactcacc acgctgtctc tgaccatgaa | 2160 |
| gccaccctga ggtgctgggc cctgagcttc taccctgcgg agatcacact gacctggcag | 2220 |
| cgggatgggg aggaccagac ccaggacacg gagctcgtgg agaccaggcc tgcagggat | 2280 |
| ggaaccttcc agaagtgggc ggctgtggtg gtgccttctg gacaggagca gagatacacc | 2340 |
| tgccatgtgc agcatgaggg tttgcccaag cccctcaccc tgagatgggg taaggaggga | 2400 |
| gacggggtg tcatgtcttt tagggaaagc aggagcctct ctgacccttta gcagggtcag | 2460 |
| ggcccctcac cttcccctct tttcccagag ccgtcttccc agcccaccat ccccatcgtg | 2520 |
| ggcatcattg ctggcctggt tctctttgga gctgtgatca ctggagctgt ggtcgctgct | 2580 |
| gtgatgtgga ggaggaagag ctcaggtggg aaggggtga agggtgggtc tgagatttct | 2640 |
| tgtctcactg agggttccaa gacccaggta gaagtgtgcc ctgcctcgtt actgggaagc | 2700 |
| accacccaca attatgggcc tacccagcct gggccctgtg tgccagcact tactcttttg | 2760 |

| | |
|---|---|
| taaagcacct gttaaaatga aggacagatt tatcaccttg attacagcgg tgatgggacc | 2820 |
| tgatcccagc agtcacaagt cacaggggaa ggtccctgag gaccttcagg agggcggttg | 2880 |
| gtccaggacc cacacctgct ttcttcatgt ttcctgatcc cgccctgggt ctgcagtcac | 2940 |
| acatttctgg aaacttctct gaggtccaag acttggaggt tcctctagga ccttaaggcc | 3000 |
| ctgactcttt tctggtatct cacaggacat tttcttccca cagatagaaa aggagggagc | 3060 |
| tactctcagg ctgcaagtaa gtatgaagga ggctgatgcc tgaggtcctt gggatattgt | 3120 |
| gtttgggagc ccatggggga gctcacccac cccacaattc ctcctctagc cacatcttct | 3180 |
| gtgggatctg accaggttct gttttgttc taccccaggc agtgacagtg cccagggctc | 3240 |
| tgatgtgtct ctcacagctt gtaaaggtga gagcctggag ggcctgatgt gtgttgggtg | 3300 |
| ttgggcggaa cagtggacac agctgtgcta tggggtttct ttccattgga tgtattgagc | 3360 |
| atgcgatggg ctgtttaaag tgtgaccct cactgtgaca gatacgaatt tgttcatgaa | 3420 |
| tattttttc tatagtgtga acagctgcc ttgtgtggga ctgagaggca agagttgttc | 3480 |
| ctgcccttcc ctttgtgact tgaagaaccc tgactttgtt tctgcaaagg cacctgcatg | 3540 |
| tgtctgtgtt cgtgtaggca taatgtgagg aggtggggag accacccac ccccatgtcc | 3600 |
| accatgaccc tcttcccacg ctgacctgtg ctccctcccc aatcatcttt cctgttccag | 3660 |
| agaggtgggg ctgaggtgtc tccatctctg tctcaacttc atggtgcact gagctgtaac | 3720 |
| ttcttccttc cctattaaaa ttagaacctg agtataaatt tactttctca aattcttgcc | 3780 |
| atgagaggtt gatgagttaa ttaaaggaga agattcctaa aatttgagag acaaaataaa | 3840 |
| tggaacacat gagaaccttc cagagtccac gtgttgctta tgctgatttg ttgcagggga | 3900 |
| ggagagtaga tggggctgtg cccagtttct gttccggcca ctatgggctt tatgtggtca | 3960 |
| ctgcttggct gggtcatctt tgctgctcca ttgtccttgg | 4000 |

<210> SEQ ID NO 58
<211> LENGTH: 1601
<212> TYPE: DNA
<213> ORGANISM: Homo sapiens

<400> SEQUENCE: 58

| | |
|---|---|
| aaaccacaag acagacttgc aaaagaaggc atgcacagct cagcactgct ctgttgcctg | 60 |
| gtcctcctga ctggggtgag ggccagccca ggccagggca cccagtctga aacagctgc | 120 |
| acccacttcc caggcaacct gcctaacatg cttcgagatc tccgagatgc cttcagcaga | 180 |
| gtgaagactt tctttcaaat gaaggatcag ctggacaact tgttgttaaa ggagtccttg | 240 |
| ctggaggact ttaagggtta cctgggttgc aagccttgt ctgagatgat ccagttttac | 300 |
| ctggaggagg tgatgcccca agctgagaac caagacccag acatcaaggc gcatgtgaac | 360 |
| tccctggggg agaacctgaa gaccctcagg ctgaggctac ggcgctgtca tcgatttctt | 420 |
| ccctgtgaaa acaagagcaa ggccgtggag caggtgaaga atgcctttaa taagctccaa | 480 |
| gagaaaggca tctacaaagc catgagtgag tttgacatct tcatcaacta catagaagcc | 540 |
| tacatgacaa tgaagatacg aaactgagac atcagggtgg cgactctata gactctagga | 600 |
| cataaattag aggtctccaa aatcggatct ggggctctgg gatagctgac ccagccctt | 660 |
| gagaaacctt attgtaccctc tcttatagaa tatttattac ctctgatacc tcaacccca | 720 |
| tttctattta tttactgagc ttctctgtga acgattaga aagaagccca atattataat | 780 |
| ttttttcaat atttattatt ttcacctgtt tttaagctgt ttccataggg tgacacacta | 840 |

| | |
|---|---|
| tggtatttga gtgttttaag ataaattata agttacataa gggaggaaaa aaaatgttct | 900 |
| ttggggagcc aacagaagct tccattccaa gcctgaccac gctttctagc tgttgagctg | 960 |
| ttttccctga cctccctcta atttatcttg tctctgggct tggggcttcc taactgctac | 1020 |
| aaatactctt aggaagagaa accagggagc ccctttgatg attaattcac cttccagtgt | 1080 |
| ctcggaggga ttcccctaac ctcattcccc aaccacttca ttcttgaaag ctgtggccag | 1140 |
| cttgttattt ataacaacct aaatttggtt ctaggccggg cgcggtggct cacgcctgta | 1200 |
| atcccagcac tttgggaggc tgaggcgggt ggatcacttg aggtcaggag ttcctaacca | 1260 |
| gcctggtcaa catggtgaaa ccccgtctct actaaaaata caaaaattag ccgggcatgg | 1320 |
| tggcgcgcac ctgtaatccc agctacttgg gaggctgagg caagagaatt gcttgaaccc | 1380 |
| aggagatgga agttgcagtg agctgatatc atgcccctgt actccagcct gggtgacaga | 1440 |
| gcaagactct gtctcaaaaa aataaaaata aaaataaatt tggttctaat agaactcagt | 1500 |
| tttaactaga atttattcaa ttcctctggg aatgttacat tgtttgtctg tcttcatagc | 1560 |
| agattttaat tttgaataaa taaatgtatc ttattcacat c | 1601 |

<210> SEQ ID NO 59
<211> LENGTH: 12150
<212> TYPE: DNA
<213> ORGANISM: Ricinus communis

<400> SEQUENCE: 59

| | |
|---|---|
| atatttcacg aactgataca atatagcaag agattgaaaa aactcaaatt cttacaaaac | 60 |
| tgaactgaaa taaacaaga gatgcataat aaaaaaatac aaatcttgat acttattaca | 120 |
| actggaatat gcgactaagc tgaaataaac tgacattaaa gacatgacag aaatacatgt | 180 |
| tttggtctat aacaacctaa gtagaaatcg cagcctgttg atgcacagat acatgtattc | 240 |
| ttatatattt gtattaatat tttaatttat gtacatatcg agatgaatga aaataagcta | 300 |
| atatttgtca tttagaaatt attccaaaac tgaatcatct tacttgagtt atttaattaa | 360 |
| taaaattaaa tatatttcat taaacaatgc attttctctt taaaacaatc catttgaatc | 420 |
| ttactttata ggaagacctt gatagataaa caatgtattg gatatacgtt ttttttagat | 480 |
| gctctaaaga ttgcattaga atgaaataaa acttttttact tttaagatttt ttgctctttta | 540 |
| aaataaaaag tacaaacttt gataagtttt atataaccta aaaagaaatt gtaacatgtg | 600 |
| agtttgagat gtcttatata atctacaaag atatttaaag agtataaaca gtaaagcaat | 660 |
| aatacttagg tgatgaaaat acctcactta gtactaatac aacaaagcaa gatatcgaac | 720 |
| aaatcttaaa tctttgcaaa actgaactga agtaaaacaa gaaatgcata ataataagac | 780 |
| aaatcttgga acttattata gctggaatat gccagtaagc tgaaataaat tgatactaag | 840 |
| gacacaacag aaacacatgc gtctgcaacc taagaagaag ttgcaacctg tcgatgcata | 900 |
| aatatacata tgcgacgtat attgctatgt atgaaaataa gcgaatactt atcatttgga | 960 |
| atttattcca aaattggatc atcttgctga gttattcaat taataataat gaatatattt | 1020 |
| tattaagaaa taaaaaattt accttttcct ctttaaaacg atttatttga atattacttt | 1080 |
| atgagaaagac ttttttataat cagaaaactt gatatataaa gaatgtattt gataatgttt | 1140 |
| ctttagagat gctctaaaga ttgtattgca cttaaataaa acctttttact cttaatagtt | 1200 |
| tagtatttct caaaattatt actctttaaa gtaaatagct caaactttga gaagtcttat | 1260 |
| gtaaactaaa caaaaattgt aacctacgag tttgagatgt cttatacaac ctaaaataaa | 1320 |
| atttaaagaa tataaacttt aagatgtctt tttctatata atcaattta ttttgaaaaa | 1380 |

```
ccaccaaagc aaaaaaaatt taggtgatgg aaatatccta cctagaacta ataaaatata    1440
gcaaaagatt aaacaaatct caaattctta taaaattgaa ctgaagtaaa acaagagatg    1500
tataataaca aattttggta cttaatacaa aaatatgtca ttaagctaaa gtaaagtgat    1560
aataaggaca caatataaac acatgctttg gcctccagca atctaataag aaattgcaac    1620
ctatcgatgc acaaatacac gtatctttat atgcttatat aagtatttta atttgtgtac    1680
gtgtattcaa atgactgaaa ataaactaaa acttgtcata taaaattttt tcaaaattaa    1740
atgatcttgc taagttattc actaataata ataaatatat ttcattaaaa ataaaaattt    1800
gtcctttctc tataaaagag tccattagaa tcttactata tatgaaggct ttttataatt    1860
aaaaaacttg atatataaag aatgtattgg aggtgcattt ttttttgag atgttctgaa    1920 gattgcattg gactacaata aaagttttta cttttacttc ttagaattct tgctctttaa    1980
aataataagc acaaactttg agatgtcttg tagaacctaa gaaaaaaatt acaatttgtg    2040 attttttagat gttttataca atctaaaaag agatttgaag agtataaatt ttaagatgtt    2100
ttatacaacc taaaacaaat tgtaatctgt cgacgcacag acacgtattt ttatatattt    2160
ataaagatca ttttaattta tgtacttata tttagataaa taaaaataag ctaatatttg    2220
tcatatataa attatttcat aactgaattg tctgatttgt tagtgttatt aaattaataa    2280
taatagttat attttattaa ataataaaag atttacctttt tctctataaa aaggggaaga    2340
aatgtggtta ctaaaaccat ctcatattcc tccgctttct tcctcagctg ctcactttgt    2400
aagtattacg actttctcaa acttcctact tgttttcaat taatgttatt ctacctgact    2460
tcatatatat ctcttttctt ttgggatcat tattactgct actgtaatga tcgagaaaaa    2520
tctcttcttc ttatcattat gacttcatat attatcatct tctatcactt catataatgt    2580
ttttgatttt atgattcaat atatttataa ttaagttcta tctttaaacg agagcaacca    2640
attaaagaaa caagagtaaa tatatataaa ttgtaaggta ttatttgttt gatttaaatc    2700
attaaatagc tagatcttct ttttcttttc ttttttttctt tctcatccaa agtttttatg    2760
aattgcaggc tattagtaat atagatggta gaaagaaaat taaaattaaa acttcttcaa    2820
tcatcacaaa tgagagtacc aactaaaacta tgtgattttg gtaaaaaatg caaaacaagt    2880
acttatatat atatatatat atatatatat atatatatat atatatatat tctttttataa    2940 atcagtatat acattttact ctgattacca taatattata gatttactaa aggtgacact    3000
aatgttatat attttggtta gaatggtagt gttttctttt cttaaagatg ctctagagga    3060
ttcttaacaa aagaatataa tatataaata atatattaaa gatgccctag aaaatgcatt    3120
tactgtactt aaataaacctg ttttgctctt aatattttat tattttattt tctataataa    3180
aaaatatttt aagaaatatt taagtataaa aaataaagta ttttattgat gtccactgta    3240 cttttttatat tttatttctt attttacttt tgtttccaag ggcatcaata tcttcttctt    3300
ttttctgttt aattttttatt aataaaaaaa ataattacaa atattaatta atcaaataca    3360
tagaaattta ttttttataaa aaaaatcctt caaattcttt taaaatgtca ttttgaccct    3420
aaatttcttt taatagttag tgttctaata aaaaaaattt acccaataat ttttctaata    3480
tttcattatt cttttataag acaaactctt agcctctaga attattttaa ggatatatat    3540
aatttgtctc tctttctctt taacatagcc ttagtttcca ataaataaat aatgaaatat    3600
atttcactct tcatttcttt aaacttctta cattttttt tgtagcattc tttgtaagtg    3660
gaatgacaaa accgttaatg atgttctttt aaaagtgaaa gatgtttata tattgcagta    3720
```

```
cagataatga tatatctact gcactacata aaacaattta aatctccctg tttattttaa    3780
gaagttatat tttctttctt tctcatccta agaaagttaa attactgtaa tcgacattat    3840
atgaatttta actaattccg tttctaattt ataattattt cgttaaacca atcaattccc    3900
tttaaacact gcttatgcat attctgtctc aatttatata tggcatgcat cttccgtatt    3960
aatttataag ttcattttta ttgatcaagt atttgtggtt ttctttatat aaaaaaatgt    4020
attagtgttt ttctgtatta attttataag ttcatcttta tgagaatgct aatgtatttg    4080
gacagccaat aaaattccaa gaattgctgc aatcaaagat gaaaccggga ggaaatacta    4140
ttgtaatatg gatgtatgca gtggcaacat ggctttgttt tggatccacc tcagggtggt    4200
ctttcacatt agaggataac aacatattcc ccaaacaata cccaattata aactttacca    4260
cagcgggtgc cactgtgcaa agctacacaa actttatcag agctgttcgc ggtcgtttaa    4320
caactggagc tgatgtgaga catgaaatac cagtgttgcc aaacagagtt ggtttgccta    4380
taaaccaacg gttttatttta gttgaactct caaatcatgc agagctttct gttacattag    4440
cgctggatgt caccaatgca tatgtggtcg gctaccgtgc tggaaatagc gcatatttct    4500
ttcatcctga caatcaggaa gatgcagaag caatcactca tcttttcact gatgttcaaa    4560
atcgatatac attcgccttt ggtggtaatt atgatagact tgaacaactt gctggtaatc    4620
tgagagaaaa tatcgagttg ggaaatggtc cactagagga ggctatctca gcgctttatt    4680
attacagtac tggtggcact cagcttccaa ctctggctcg ttcctttata atttgcatcc    4740
aaatgatttc agaagcagca agattccaat atattgaggg agaaatgcgc acgagaatta    4800
ggtacaaccg gagatctgca ccagatccta gcgtaattac acttgagaat agttggggga    4860
gactttccac tgcaattcaa gagtctaacc aaggagcctt tgctagtcca attcaactgc    4920
aaagacgtaa tggttccaaa ttcagtgtgt acgatgtgag tatattaatc cctatcatag    4980
ctctcatggt gtatagatgc gcacctccac catcgtcaca gttttctttg cttataaggc    5040
cagtggtacc aaattttaat gctgatgttt gtatggatcc tgagcccata gtgcgtatcg    5100
taggtcgaaa tggtctatgt gttgatgtta gggatggaag attccacaac ggaaacgcaa    5160
tacagttgtg gccatgcaag tctaatacag atgcaaatca gctctggact ttgaaaagag    5220
acaatactat tcgatctaat ggaaagtgtt taactactta cgggtacagt ccgggagtct    5280
atgtgatgat ctatgattgc aatactgctg caactgatgc cacccgctgg caaatatggg    5340
ataatggaac catcataaat cccagatcta gtctagtttt agcagcgaca tcagggaaca    5400
gtggtaccac acttacagtg caaaccaaca tttatgccgt tagtcaaggt tggcttccta    5460
ctaataatac acaaccttt gtgacaacca ttgttgggct atatggtctg tgcttgcaag    5520
caaatagtgg acaagtatgg atagaggact gtagcagtga aaaggctgaa caacagtggg    5580
ctctttatgc agatggttca atacgtcctc agcaaaaccg agataattgc cttacaagtg    5640
attctaatat acgggaaaca gttgtcaaga tcctctcttg tggccctgca tcctctggcc    5700
aacgatggat gttcaagaat gatggaacca ttttaaattt gtatagtggg ttggtgttag    5760
atgtgagggc atcggatccg agccttaaac aaatcattct ttaccctctc catggtgacc    5820
caaaccaaat atggttacca ttattttgat agacagatta ctctcttgca gtgtgtatgt    5880
cctgccatga aaatagatgg cttaaataaa aaggacattg taaattttgt aactgaaagg    5940
acagcaagtt attgcagtcc agtatctaat aagagcacaa ctattgtctt gtgcattcta    6000
aatttatgga tgaattgtat gaattaagct aattattttg gtcatcagac ttgatatctt    6060
tttgaataaa ataaataata tgttttttca aacttataaa actatgaatg atatgaatat    6120
```

```
aatgcggaga ctagtcaatc ttttatgtaa ttctatgatg ataaaagctt gtctcttaac   6180
ttagtgaatt tgtatccaag taaaaaacag cctactaagt catggattcc ttcaaattta   6240
cgctcttatt ataagcttaa ttttcatcca cgatcatccc tattcatgtg atgcacaaga   6300
acttaaggta tatagatttg aagtaattcc ttaattataa tttttaagtt tatcactttc   6360
tttactttct aatttctttt tctcaaattg tactaattaa ctcattgaag aatttaacaa   6420
cttgttcatc agttccatag taattctcaa taaatttatg gtctcacaac tcaagcatcc   6480
atgggttcat aagttgtgat aatcaggcag cttcatatat attgaaatta acataaggag   6540
taaagtgggt tgagcaatgc caggtggtac atccaggtgg tacatccata tatacttctt   6600
cctccaaatc accatgtaaa aaagtatttt ttacatcaaa ttgtcttaat gcccatcctt   6660
tagttgctgc aatagaaatc agtattcaaa tcgtaccaag tttcgccaca ggtgcaaacg   6720
tttcctggta gtcaattcca tacttctgag taaatccttt cgctaccagt ctcgcttttc   6780
gcctgtctag actcccatct gccttaagct tcactgtata gatccattta cagccaatcg   6840
tattcttccc ctctggtaat ttcacaaact cccatgttgc attcttctct agggctttca   6900
cctcttcctc catcgcctct tttcatttca agtcttgcat tgcctcctgc acactattag   6960
gaatcgcaat cccggataat tcactagtgc taagtgcata ataatctgtt aaatgattat   7020
gtcgaatacc attcttagtt aaaaaattac ttaaatgact atccataaat tcctttgcat   7080
tatcagtttg ccaaactaaa acccatgtac gatattgatt tctaataaaa tttcaaaaat   7140
cacaaaaagc tttacttacc tcacttttgt tccgaagtaa ggttatccaa gtcatacgag   7200
tacattcgtc tataaaagtt ccgaaatatc tagcacctga taatgaagga atttttgcag   7260
gaccccaaac atcagaatgt ataacagcaa atggttcagt actttttatta aaactaggca   7320 aataagtagc acggtggctc ttaccaagtt cacacacatc acaattaaac acggaatcat   7380
ccaaattaac aaacaattca ggttttaatt ttttcaaata actaaatgac aaatgtccaa   7440
ggcgtcgatg ccatagccaa attctttcca ttgtattact taagctttca gtcgtgtaaa   7500
cctcacttat tttcttctct cctatctcag tcaagtctag ataataaagt ttgcctcgtt   7560
taacaccata accaagagtc tcccgagtca ggatgtcctg aaaaacacaa tatgaaggcc   7620
agaaagttac agtacagtta agagacgagg ttatttgtcc aaccgagagt aagttacaag   7680
acagtgtaag aacaatcaat acagatttta aattcagatt ttttgaaaga gtaatggatc   7740
cttctccact aacaatacat ttggatccat ttgttattga cacggtaaaa tgagaggatg   7800
gaatgaaaga ataaattcga tcagaattgc ataccatatg atcagatgca ccagggtcta   7860
ttgtccacaa tgttcacaca gcaagttaca ttttttttcca gctccatttt tcctgttttt   7920
tccataattc tggcaaacct gaaatacagt aggctccaca gttgcatttg ttcctcccat   7980
tgtcttacat tgttgatctt ctcttcgaac ataagcatat gtttgttcta aatcaagttt   8040
agggtctttg cgcaaaatct cacctcggac ttgatcaaag tttgaatcaa gcccactgag   8100
gaagatatgc atgcgtagcc ttgccatggc agaatgcaac gctactactc catccactgt   8160
accttcatgt gactgagtac gatgatctat ctcttgaaag atttccatca actcagagta   8220
atacgtaggc aatggtctgc cctcttgttt gattgcgaaa gacttctgat tcaattcgaa   8280
taacctcgtt tcatcagttc catcataaaa tgttttgct gctgcctccc aaacatcttt   8340
ggcagtagga agtctgatga aatgttgcat cagtgaaggt atcatcgaat caatcagcca   8400
gctctttacc ttttgattct cagttatcca ggtagagtat ctcgtatctg tagttgcagg   8460
```

-continued

```
cttcacttcc gatccggtta aatacccagt tttatttcgt gctccaatac gcatctccat    8520
gagctgtgac catagagaat aattcgattc atccagtata acactggtag ggaatgatac    8580
attatcttgt tgaatgataa tttgattcga agacggattc atgatttgag tatgaggtgg    8640
atcttctgta ctcataattc tgtttaggga ttcagttttg atttgaaaaa aatttgtttt    8700
cagtatggtg agcggctgtt gtgataccat gtgagtaatg aaactctaat aattgattaa    8760
ttttcatcct ttttctctat tcattcaacc tgaatatata caaaagtttg ttacaaggat    8820
aacttctaac tacttatgta acaagcaacc ttatcaaaaa tacaattaga ataacatcta    8880
actactacag cttatacata cttatctcta tactaacaaa ttaactaaat atagttaaca    8940
agttctgaat catagtaatt ttagtctcta taatattaac aaatgaggga ctaaaatact    9000
tttcttttct taaatatgat tctatttttaa aaagcgggag atagaaaaat ttatataatt    9060
tcttactaaa aaaagtaag gataattttta tttaattcta agaacaaag caaggaaaa    9120
tgggaaagtt tataatttga tctaatttct ttgcatgata gacaggtaac tgattctcaa    9180
tacgattcta agatgatcca atataaatta tttgtgggaa ataggttcac gaaaaagcca    9240
tttgttgggg attcaatgtt tattgatttg ttttgtgtag tatgttttgc atcaattaat    9300
tagatcagct agtcatttac atattcttgc aaatttgtgc catttacaaa tgaattatct    9360
gaatttagtg taatttgatt aatttaatta gacgggtttt ccttcttcag taatcaacat    9420
acacaaagtg aaaggcaaac gagttctagc aatttaattg attaggttca agttaattaa    9480
ttaatttgat aatttatggt tcagtccgtt actgaaaatt taaaagaag tagcatgcat    9540
ctttagattc tttctctatt ttatgcatgc cattttctga ttaattgtat atgttcgttc    9600
ttcttgatta agtatttata tttatttttt atttgattag tgagctatat atatttttaa    9660
gagaatcttg atgtatttgg acaactaaaa aaattccaag aattgctaca attggagatg    9720
aaactgaaag gaaacactat ggtgtggata tacgcagtgg caacgtggct ctgcttggga    9780
tcagccttgg ggtggtaatt caatgccact gtaagctaca cattcccaac tgtaagcttt    9840
accactgttg atgccacgga gcaaatgtac agagagtgtt gtagaaaata agaataagta    9900
tatacttta tcggcttagt agccaagaag tcttttggta acctacaact cttaaacatc    9960
atatacttaa tacataagtt acacgcttaa tgaatatata tgtaacttac atatttaata  10020
ggtgactctt taatttcata acttaagcat taaaaactat acataatgat tattaaatta  10080
aatttagttt ttcaacactc cttaaattta atttcagatc aaaccgagtc ttgctcttaa  10140
tctggcaaaa tcttcaaact ttaatgcctt cgtcaaaata tcagcaagtt gatcttgcga  10200
cttgacatac ttcagctcta tttccttctt acggatactt tctctgatga aatgatatct  10260
tctattaatg tatttactct taacatgtaa aataggattc ttgctcaatg ctatagcga  10320
tttattatca ataaaaatat caattggttc ttcgtttgaa accaatagca cctctaacac  10380
ctttcttaac catgtggcat gacaaacaca agcagcagca acaacatact taacttcaca  10440
agttgaaaga attacaatag attacttctt tgaactccat gtaaaagcag tctctccaat  10500
agaaaacaca aaacccattg tactctttcg atcatcaata tcacctcctc aatcactatc  10560
actatagcct actagactga aacttttga aggtgagtaa aacaaaccat aatctaaagt  10620
tccttcgaca tatctcaaaa ttcttttacc agccttcatg tgcgaatctg ttggtgcctc  10680
catgtagcga ctaataagtc ctactccata aagaatatca ggtctagtac aagtcaagta  10740
cctcaagttt ccaacaaatc tttgaaacaa aattggattc accttctcag tattatcata  10800
tcttgacagc tttactccac attcaactag tgtgctgaca agctgacatt gctccatgcc  10860
```

```
aaactcctttt aagatctttc ttacatagct cttgtgagaa ataaaaatgc catcattagt   10920
ttgtttcact ttgattccca gataataaga catcaaccct atatctgtca tctcaaattc   10980
agcagccatc tccttttttga attattcaat cattgctgaa ttattttttct gtaaagatca   11040 aatcatcaac atacaagcac accacaagaa catcaccatt ctctttcttc ttagaataaa   11100
gagaatattc atgaggatat ttcagaaaat ttttctttttt gaataatca tcaatcctgt   11160 tgtaccatgc ccttagtact tgcttcaatc catacaaagg taccttcagt tttaaaactt   11220
tgttttcttc ccctctaaca acatatctga aaggttgttt tagatatcct tcttcttcta   11280
agtatccatt caagaacgcc gatttcacgt ccatttgaaa aattcttcat ctcttttgtg   11340
cagctaaagc aatgattaaa caaattattt ccaatcgagc aactactaca aagacttcat   11400
catagtcaat tccatgttgt tggctaaacc cttttgcaac aagtcgagcc ttgtatttct   11460
cgacatctcc gttttcattc ttttaactt tttataaatc catttcacac caacaacttg   11520
cttgccttag gaaagattgc taattcccaa gtgtcattct tttgaattga ttttatttcg   11580
tcatctatgg ctactctcca ttttttcatttt ttcatcgctt cttcaaaatt cattggttca   11640
gtatctgcag aaatacaata atgaacaaaa tctaaaactt catcaatgtt agcatatatg   11700
tcctacagat ttctcatctt tgtaggtttt tcagatgatc ttgaacgact tgaatctcct   11760
tgaatacttg ctggagttct tggaagtgtc aagttctgta catcaaaatt aaaatgttga   11820
acatcttgat ctgaataatc aaaaattgga aaaaaattat aattttctga ttgattctcc   11880
caatttcatc catcagcttc ctcaaacttg acatctcgac tcaggataat ctttttgctt   11940
gtcggattgt acaacttgta gactttagac tttgcatcat atccaacaaa aatgaatttt   12000
ccacttttat catccagctt aattctggtt tcatctgcaa catgaacata agcaacataa   12060
ccaaaaactc taagatgaga aagagttggc tttcttccac tccatgcttc ctgtggtata   12120
gacttctgca aactctttat aggacatatg                                      12150
```

<210> SEQ ID NO 60
<211> LENGTH: 39
<212> TYPE: DNA
<213> ORGANISM: Artificial sequence
<220> FEATURE:
<223> OTHER INFORMATION: Single strand DNA oligonucleotide

<400> SEQUENCE: 60

```
tcctcagcta gcaccaaggg accatcggtc ttccccctg                              39
```

<210> SEQ ID NO 61
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 61

```
gcagggtgta cacctgtggt tc                                               22
```

<210> SEQ ID NO 62
<211> LENGTH: 51
<212> TYPE: DNA
<213> ORGANISM: Artificial sequence
<220> FEATURE:
<223> OTHER INFORMATION: Single strand DNA oligonucleotide

<400> SEQUENCE: 62
actgaacctt ggagtcaggt accacattga ttattgagta gttattaata g        51

<210> SEQ ID NO 63
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 63
gggcccctgt ggagagaaag gcaaagtgga tg        32

<210> SEQ ID NO 64
<211> LENGTH: 51
<212> TYPE: DNA
<213> ORGANISM: Artificial sequence
<220> FEATURE:
<223> OTHER INFORMATION: Single strand DNA oligonucleotide

<400> SEQUENCE: 64
ctttgccttt ctctccacag gggcccactc cgacattgtg ctgacccaat c        51

<210> SEQ ID NO 65
<211> LENGTH: 67
<212> TYPE: DNA
<213> ORGANISM: Artificial sequence
<220> FEATURE:
<223> OTHER INFORMATION: Single strand DNA oligonucleotide

<400> SEQUENCE: 65
cggtttaaaa aacgggacct ctggagcggc cgcttattaa cactctcccc tgttgaagct        60
ctttgtg        67

<210> SEQ ID NO 66
<211> LENGTH: 51
<212> TYPE: DNA
<213> ORGANISM: Artificial sequence
<220> FEATURE:
<223> OTHER INFORMATION: Single strand DNA oligonucleotide

<400> SEQUENCE: 66
tccagaggtc ccgttttta aaccggtttt ttaaaccgct gatcagcctc g        51

<210> SEQ ID NO 67
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 67
tagctcgatc cgtcgagaga attccccag catgcctgct attg        44

<210> SEQ ID NO 68
<211> LENGTH: 657
<212> TYPE: DNA
<213> ORGANISM: Artificial sequence
<220> FEATURE:
<223> OTHER INFORMATION: Light chain of anti-streptavidin (anti-SA)

<400> SEQUENCE: 68
atggatatcg tgctgactca gccaccctca gcgtctggga ccccggggca gagggtcacc        60
ctctcttgta ctggaagcag ctccaacatc ggaagttatt ctgtaagctg gtaccagcag        120
cttccaggaa cggctcccaa actcctcatc tatgacaata taagcgacc ctcaggggtc        180

```
tctgaccggt tctctggctc caagtctggc acctcagcct ccctggccat cagtgggctc    240
cggtccgagg atgaggctga ttattactgc cagtcctatg acagcagcct gactggttcc    300
gtggtattcg gcggaggcac ccagctcacc gtcctaggtc agcccaaggc tgccccctcg    360
gtcactctgt tcccgccctc ctctgaggag cttcaagcca acaaggccac actggtgtgt    420
ctcataagtg acttctaccc gggagccgtg acagtggcct ggaaggcaga tagcagcccc    480
gtcaaggcgg gagtggagac caccacaccc tccaaacaaa gcaacaacaa gtacgcggcc    540
agcagctatc tgagcctgac gcctgagcag tggaagtccc acagaagcta cagctgccag    600
gtcacgcatg aagggagcac cgtggagaag acagtggccc ctgcagaatg ttcttaa     657
```

<210> SEQ ID NO 69
<211> LENGTH: 218
<212> TYPE: PRT
<213> ORGANISM: Artificial sequence
<220> FEATURE:
<223> OTHER INFORMATION: Light chain of anti-streptavidin (anti-SA)

<400> SEQUENCE: 69

```
Met Asp Ile Val Leu Thr Gln Pro Pro Ser Ala Ser Gly Thr Pro Gly
1               5                   10                  15

Gln Arg Val Thr Leu Ser Cys Thr Gly Ser Ser Ser Asn Ile Gly Ser
                20                  25                  30

Tyr Ser Val Ser Trp Tyr Gln Leu Pro Gly Thr Ala Pro Lys Leu
            35                  40                  45

Leu Ile Tyr Asp Asn Asn Lys Arg Pro Ser Gly Val Ser Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Ser Ser
                85                  90                  95

Leu Thr Gly Ser Val Val Phe Gly Gly Gly Thr Gln Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Ala Glu Cys Ser
    210                 215
```

<210> SEQ ID NO 70
<211> LENGTH: 657
<212> TYPE: DNA
<213> ORGANISM: Artificial sequence
<220> FEATURE:
<223> OTHER INFORMATION: Light chain of anti-PE clone B11

<400> SEQUENCE: 70

```
atggatatcg tgctgactca gccaccctca gcgtctggga cccccgggca gagggtcacc        60
atctcttgct ctggaaccag cagtgatgtt gggaattcta accttgtctc ttggtaccag       120
cagctcccag gaacggctcc caaactcctc atttatggga acagcaatcg gccctcaggg       180
gtccctgacc ggttctctgg ctccaagtct ggcacctcag cctccctggc catcagtggg       240
ctgcggtccg aggatgaggc tgattattac tgctgctcat atgcaggtac tggctcccct       300
gatgtcttcg gaactggcac caagctgacc gtcctaggtc agcccaaggc tgcccccteg       360 gtcactctgt tcccgccctc ctctgaggag cttcaagcca acaaggccac actggtgtgt       420
ctcataagtg acttctaccc gggagccgtg acagtggcct ggaaggcaga tagcagcccc       480
gtcaaggcgg gagtggagac caccacaccc tccaaacaaa gcaacaacaa gtacgcggcc       540
agcagctatc tgagcctgac gcctgagcag tggaagtccc acagaagcta cagctgccag       600
gtcacgcatg aagggagcac cgtggagaag acagtggccc tgcagaatgt tcttaa          657
```

<210> SEQ ID NO 71
<211> LENGTH: 218
<212> TYPE: PRT
<213> ORGANISM: Artificial sequence
<220> FEATURE:
<223> OTHER INFORMATION: Light chain of anti-PE clone B11

<400> SEQUENCE: 71

```
Met Asp Ile Val Leu Thr Gln Pro Pro Ser Ala Ser Gly Thr Pro Gly
1               5                  10                  15

Gln Arg Val Thr Ile Ser Cys Ser Gly Thr Ser Ser Asp Val Gly Asn
            20                  25                  30

Ser Asn Leu Val Ser Trp Tyr Gln Gln Leu Pro Gly Thr Ala Pro Lys
        35                  40                  45

Leu Leu Ile Tyr Gly Asn Ser Asn Arg Pro Ser Gly Val Pro Asp Arg
    50                  55                  60

Phe Ser Gly Ser Lys Ser Gly Thr Ser Ala Ser Leu Ala Ile Ser Gly
65                  70                  75                  80

Leu Arg Ser Glu Asp Glu Ala Asp Tyr Tyr Cys Cys Ser Tyr Ala Gly
                85                  90                  95

Thr Gly Ser Pro Asp Val Phe Gly Thr Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Ala Glu Cys Ser
    210                 215
```

<210> SEQ ID NO 72
<211> LENGTH: 1347
<212> TYPE: DNA
<213> ORGANISM: Artificial sequence
<220> FEATURE:
<223> OTHER INFORMATION: Heavy chain of anti-streptavidin (anti-SA)

<400> SEQUENCE: 72

```
atggaggtgc agctgttgga gtctggggga ggcttggtac agcctggggg gtccctgaga      60
ctctcctgtg cagcctctgg attcaccttc agtggctact ggatgcactg ggtccgccag     120
gctccaggca aggggctgga gtgggtttca gaaattagtg gtagtggtga tagcacacac     180
tacgagact ccgtgaaggg ccggttcacc atctccagag acaattccaa gaacacgctg      240
tatctgcaaa tgaacagcct gagagccgag gacacggccg tgtattactg tgcaagagga     300
cggaacggat ccctcgacta ctgggccag ggcaccctgg tcacagtctc ctcagctagc      360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcaccca gacctacatc      600
tgcaacgtga atcacaagcc cagcaacacc aaggtggaca gagagttga gcccaaatct      660
tgtgacaaaa ctcacacatg cccaccgtgc ccagcacctg aactcctggg gagaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta caacagcacg     900
taccgtgtgg tcagcgtcct caccgtcctg caccaggact ggctgaatgg caaggagtac     960
aagtgcaagg tctccaacaa agccctccca gcccccatcg agaaaaccat ctccaaagcc    1020
aaagggcagc cccgagaacc acaggtgtgc accctgcccc catcccggga ggagatgacc    1080
aagaaccagg tcagcctgag ctgcgcggtc aaaggcttct atcccagcga catcgccgtg    1140
gagtgggaga gcaatgggca gccggagaac aactacaaga ccacgcctcc cgtgctggac    1200
tccgacggct ccttcttcct cgttagcaag ctcaccgtgg acaagagcag gtggcagcag    1260
gggaacgtct tctcatgctc cgtgatgcat gaggctctgc acaaccacta cacgcagaag    1320
agcctctccc tgtccccggg taaatga                                        1347
```

<210> SEQ ID NO 73
<211> LENGTH: 448
<212> TYPE: PRT
<213> ORGANISM: Artificial sequence
<220> FEATURE:
<223> OTHER INFORMATION: Heavy chain of anti-streptavidin (anti-SA)

<400> SEQUENCE: 73

```
Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Gly
            20                  25                  30

Tyr Trp Met His Trp Val Arg Gln Ala Pro Gly Lys Gly Leu Glu Trp
        35                  40                  45

Val Ser Glu Ile Ser Gly Ser Gly Asp Ser Thr His Tyr Gly Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95
```

Cys Ala Arg Gly Arg Asn Gly Ser Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Arg Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 74
<211> LENGTH: 1362
<212> TYPE: DNA
<213> ORGANISM: Artificial sequence
<220> FEATURE:
<223> OTHER INFORMATION: Heavy chain of anti-PE clone B11

<400> SEQUENCE: 74
atggaggtgc agctgttgga gactggggga ggcttggtac agcctggggg gtccctgaga     60
ctctcctgtg cagcctctgg attcaccttt gacaactatg ccataaactg ggtccgccag    120

```
gctccaggca aggggctgga gtgggtctca ggtattagtt ggaatagtgg tagcataggc    180
tatgcggact ctgtgaaggg ccgattcacc atctccagag acaattccaa gaacacgctg    240
tatctgcaaa tgaacagcct gagagccgag gacacggccg tatattactg tgcgagaggg    300
gccccccact acggtgggag gggggagttt gacttctggg gccagggcac cctggtcacg    360
gtctcctcag ctagcaccaa gggcccatcg gtcttccccc tggcaccctc ctccaagagc    420
acctctgggg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt ggacaagaga    660
gttgagccca aatcttgtga caaaactcac acatgcccac cgtgcccagc acctgaactc    720
ctggggagac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa   1020
accatctcca aagccaaagg gcagccccga gaaccacagg tgtgcaccct gcccccatcc   1080
cgggaggaga tgaccaagaa ccaggtcagc ctgagctgcg cggtcaaagg cttctatccc   1140
agcgacatcg ccgtggagtg ggagagcaat gggcagccgg agaacaacta caagaccacg   1200
cctcccgtgc tggactccga cggctccttc ttcctcgtta gcaagctcac cgtggacaag   1260
agcaggtggc agcaggggaa cgtcttctca tgctccgtga tgcatgaggc tctgcacaac   1320
cactacacgc agaagagcct ctccctgtcc ccgggtaaat ga                      1362
```

<210> SEQ ID NO 75
<211> LENGTH: 453
<212> TYPE: PRT
<213> ORGANISM: Artificial sequence
<220> FEATURE:
<223> OTHER INFORMATION: Heavy chain of anti-PE clone B11

<400> SEQUENCE: 75

```
Met Glu Val Gln Leu Leu Glu Thr Gly Gly Gly Leu Val Gln Pro Gly
1               5                   10                  15

Gly Ser Leu Arg Leu Ser Cys Ala Ala Ser Gly Phe Thr Phe Asp Asn
            20                  25                  30

Tyr Ala Ile Asn Trp Val Arg Gln Ala Pro Gly Lys Gly Leu Glu Trp
        35                  40                  45

Val Ser Gly Ile Ser Trp Asn Ser Gly Ser Ile Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Ala Pro His Tyr Gly Gly Arg Gly Glu Phe Asp Phe
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140
```

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Arg Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Glu Glu Met Thr Lys Asn Gln
            355                 360                 365

Val Ser Leu Ser Cys Ala Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
450
```

BI- AND MONOSPECIFIC, ASYMMETRIC ANTIBODIES AND METHODS OF GENERATING THE SAME

RELATED APPLICATIONS

This application is a continuation of U.S. patent application Ser. No. 14/005,580, filed on Sep. 17, 2013, which is a National Phase of PCT Patent Application No. PCT/IL2012/050093 having International Filing Date of Mar. 15, 2012, which claims the benefit of priority of U.S. Provisional Patent Application No. 61/453,591, filed on Mar. 17, 2011. The contents of the above applications are all incorporated by reference as if fully set forth herein in their entirety.

SEQUENCE LISTING STATEMENT

The ASCII file, entitled 69273SequenceListing.txt, created on Feb. 22, 2017, comprising 159,727 bytes, submitted concurrently with the filing of this application is incorporated herein by reference.

FIELD AND BACKGROUND OF THE INVENTION

The present invention, in some embodiments thereof, relates to bispecific antibodies, monospecific, asymmetric antibodies and methods of generating same.

Bispecific antibodies (BsAbs) are antibodies with two binding sites, each directed against a different target antigen, to which they can bind simultaneously (Baeuerle and Reinhardt, 2009). This property enables the development of therapeutic strategies that are not possible with conventional monoclonal antibodies. The primary applications of bispecific antibodies include a) simultaneous inhibition of two targets (e.g. receptors of soluble ligands, a receptor and a ligand or two different ligands), b) retargeting, where one binding specificity is directed against a target cell (usually a tumor cell) whereas the other binding site is used to recruit a toxic activity or moiety to the target cell (T or NK cells; enzyme for prodrug activation; cytokine, radionuclide, virus, toxin), c) increased specificity, when strong binding mediated by simultaneous engagement of both antibody arms can only occur on cells expressing both antigens (Fischer and Leger, 2007; Amann et al., 2009; Lutterbuese et al., 2010). Since bispecific antibodies are regarded as promising therapeutic agents, several bispecific modalities have been developed, but their utility is limited due to problems with stability and manufacturing complexity. Several strategies for the creation of bispecific antibodies have been proposed over the past 20 years but despite numerous attempts and various proposed antibody formats, the BsAbs suffer from lack of product homogeneity and challenging production problems (Fischer and Leger, 2007; Chames and Baty, 2009).

Initially, attempts were made to produce bispecific antibodies by fusing two hybridomas, each producing a different antibody, resulting in what was referred to as "quadromas" or hybrid hybridomas. However, quadromas suffered from genetic instability and yielded heterogeneous mixes of the heavy and light chains. It was found that on average an at random association of L chains with H chains was found of the two antibodies, and only a tiny fraction were the desired bispecific antibodies (De Lau et al., 1991; Massino et al., 1997). If one considers creating a bispecific antibody from two monospecific antibodies, A and B, efficient assembly of a bispecific antibody in an IgG format has two basic requirements, one is that each heavy chain associates with the heavy chain of the second antibody (heavy chain A associates with heavy chain B) and no homoassociation (A+A or B+B) occurs. The second requirement is that each light chain associates with its cognate heavy chain (light chain A with heavy chain A, and not light chain B with heavy chain A or light chain A with heavy chain B). The random association of antibody chains in quadromas could not meet those requirements.

Efficient generation of bispecific antibodies was made possible by advances in antibody engineering. Advanced antibody engineering enabled the creation of new recombinant antibody formats like tandem single-chain variable fragment (scFv) (Robinson et al., 2008), diabodies (Hudson and Kortt, 1999), tandem diabodies (Kipriyanov, 2009), two-in-one antibody (Bostrom et al., 2009), and dual variable domain antibodies (Wu et al., 2007). These new antibody formats solved some of the manufacturing issues, providing homogeneous preparations. However, most of these scaffolds, due to their small size, suffer from poor pharmacokinetics and therefore require frequent dosing or conjugation to larger carrier molecules to improve half-life (Constantinou et al., 2009).

Ridgway et al., 1996 provided a solution to one of the two criteria for making bispecific antibodies making it possible to re-consider IgG-based bispecific antibodies technically feasible. They described an engineering approach termed "knobs into holes" which allows only heterodimerization between the heavy chains of "antibodies A and B" to form, disallowing homodimerization. While studying the rules for heavy chain association, the authors postulated that it is primarily dependent on interfacial interactions between the $C_H3$ domains of the two heavy chains. When protein domains or subdomain interact, a knob is a bulky side chains that protrudes into the opposite domain where it is aligned with a small side chain that makes such invasion possible. In their approach, knob and hole variants were anticipated to heterodimerize by virtue of the knob inserting into an appropriately designed hole on the partner $C_H3$ domain. Knobs were constructed by replacing small side chains with the largest side chains, tyrosine or tryptophan. Holes of identical or similar size to the knobs were created by replacing large side chains with the smaller ones, in this case alanine or threonine. This way, two heavy chains that are knob variants can not homoassociate because of side chain clashes, and the homoassociation of two hole variants is less favored because of the absence of a stabilizing side-chain interaction. Subsequently, this group engineered a disulfide bond near the c-terminus of the CH3 domain to further stabilize the assembled bispecific antibodies (Merchant et al., 1998).

U.S. Pat. No. 7,183,076 teaches a method of generating bifunctional antibodies using the knob and hole approach.

However, the knobs into holes approach provided a solution only for the heteroassociation of the heavy chain and did not provide one for the correct pairing of each heavy chain with its cognate light chain. Therefore, in that study, a bispecific IgG capable of simultaneously binding to the human receptors HER3 and cMpl was prepared by coexpressing a common light chain and the corresponding remodeled heavy chains followed by protein A chromatography. The engineered heavy chains retain their ability to support antibody-dependent cell-mediated cytotoxicity as demonstrated with an anti-HER2 antibody (Merchant et al., 1998).

International application 2010/115589 teaches trivalent bispecific antibodies in which to a monospecific IgG carrying knobs into holes mutations, a $V_H$ and $V_L$ of a second specificity are fused at the C-terminus of the two CH3 domains.

Similar molecules are described in U.S. Patent Application Publication No. 2010/0256340.

Disulfide-stabilized Fvs were first described by the group of Andreas Plückthun (Glockshuber et al., 1990) and later by the group of Ira Pastan (Brinkmann et al., 1993; Reiter et al., 1994a; Reiter et al., 1994b; Reiter et al., 1995). The Pastan group did extensive work on dsFvs, and used molecular modeling to identify positions in conserved framework regions of antibody Fv fragments (Fvs) that are distant from CDRs, and potentially can be used to make recombinant Fv fragments in which the unstable $V_H$ and $V_L$ heterodimer is stabilized by an engineered interchain disulfide bond inserted between structurally conserved framework positions. A disulfide bond was introduced at one of these positions, $V_H44$-$V_L105$ or $V_H111$-$V_L48$ was shown to stabilize various Fvs that retain full binding and specificity.

U.S. Pat. Nos. 5,747,654, 6,147,203 and 6,558,672 teach disulfide-stabilized Fvs, wherein the Fvs are engineered to introduce additional disulfide bonds between the light and heavy chains.

Additional background art includes Jackman et al., Journal of Biological Chemistry Vol 285, No. 27, pp. 20850-20859, Jul. 2, 2010 and Schaefer et al., Proc Natl Acad Sci USA. 2011 July 5; 108(27): 11187-11192.

SUMMARY OF THE INVENTION

According to an aspect of some embodiments of the present invention there is provided an antibody comprising an Fc region and a Fab region, wherein:

(i) the Fc region comprises two non-identical heavy chains, wherein at least one of the two non-identical heavy chains comprises an amino acid modification so as to form complementation between the two non-identical heavy chains thereby increasing the probability of forming heterodimers of the non-identical heavy chains and decreasing the probability of forming homodimers of identical heavy chains; and (ii) the Fab region comprises a first covalent link between a first heavy chain and a first light chain of the Fab region and a second covalent link between a second heavy chain and a second light chain of the Fab region, wherein a position of the first covalent link relative to the first heavy chain is different to a position of the second covalent link relative to the second heavy chain.

According to an aspect of some embodiments of the present invention there is provided a method of preparing an antibody, comprising:

(a) providing a first nucleic acid molecule encoding the first heavy chain;

(b) providing a second nucleic acid molecule encoding the second heavy chain;

(c) providing a third nucleic acid molecule encoding the first light chain;

(d) providing a fourth nucleic acid molecule encoding the second light chain;

(e) culturing host cells comprising the first, second, third and fourth nucleic acid molecules under conditions that permit expression of the nucleic acid molecules; and (f) recovering the antibody.

According to an aspect of some embodiments of the present invention there is provided a pharmaceutical composition comprising as an active agent the antibody disclosed herein and a pharmaceutically acceptable carrier.

According to an aspect of some embodiments of the present invention there is provided an antibody for treating an infection or inflammatory disease or disorder.

According to an aspect of some embodiments of the present invention there is provided a method of treating an infection or an inflammatory disease or disorder in a subject in need thereof, the method comprising administering to the subject a therapeutically effective amount of the antibody disclosed herein, thereby treating the infection or inflammatory disease or disorder.

According to some embodiments of the invention, the antibody is a bispecific antibody.

According to some embodiments of the invention, the antibody is an asymmetric, mono specific antibody.

According to some embodiments of the invention, the complementation comprises a steric complementation.

According to some embodiments of the invention, the complementation comprises a charge complementation.

According to some embodiments of the invention, the Fc region comprises a protuberance of one heavy chain of the Fc region and a sterically compensatory cavity on a second heavy chain of the Fc region, the protuberance protruding into the compensatory cavity.

According to some embodiments of the invention, the protuberance is generated by substituting an amino acid at one position on a CH3 domain of the one heavy chain with another amino acid having a larger side chain volume than the original amino acid.

According to some embodiments of the invention, the compensatory cavity is generated by substituting an amino acid at one position on a CH3 domain of the second heavy chain with another amino acid having a smaller side chain volume than the original amino acid.

According to some embodiments of the invention, the first covalent link is between a CH1 domain of the one heavy chain and a CL domain of the one light chain; and the second covalent link is between a $V_H$ domain of the second heavy chain and a $V_L$ domain of the second light chain.

According to some embodiments of the invention, the first and the second covalent links are disulfide bonds.

According to some embodiments of the invention, the amino acid having a larger side chain volume than the original amino acid is selected from the group consisting of tyrosine, arginine, phenylalanine, isoleucine and tryptophan.

According to some embodiments of the invention, the amino acid having a smaller side chain volume than the original amino acid is selected from the group consisting of alanine, glycine, valine and threonine.

According to some embodiments of the invention, the antibody is selected from the group consisting of a chimeric antibody, a humanized antibody and a fully human antibody.

According to some embodiments of the invention, the CH3 domain of the first heavy chain is covalently linked to the CH3 domain of the second heavy chain.

According to some embodiments of the invention, the first antigen binding site of the antibody binds a first epitope of an antigen and the second antigen binding site of the antibody binds a second epitope of the antigen.

According to some embodiments of the invention, the first antigen binding site of the antibody binds an epitope of a first antigen and the second antigen binding site of the antibody binds an epitope of a second antigen.

According to some embodiments of the invention, each light chain is linked to its cognate heavy chain via a single disulfide bond.

According to some embodiments of the invention, the antibody is an intact antibody.

According to some embodiments of the invention, the antibody is selected from the group consisting of IgA, IgD, IgE and IgG.

According to some embodiments of the invention, the IgG comprises IgG1, IgG2, IgG3 or IgG4.

According to some embodiments of the invention, the first heavy chain comprises a T366W mutation; and the second heavy chain comprises T366S, L368A, Y407V mutations.

According to some embodiments of the invention, the first heavy chain comprises an S354C mutation and the second heavy chain comprises a Y349C mutation.

According to some embodiments of the invention, the first antigen binding site binds CD30 and the second antigen binding site binds erbB2.

According to some embodiments of the invention, the first antigen binding site binds CD30 and the second antigen binding site binds *Pseudomonas Exotoxin* (PE).

According to some embodiments of the invention, the first antigen binding site binds CD30 and the second antigen binding site binds strepavidin.

According to some embodiments of the invention, at least one of the heavy chains is attached to a therapeutic moiety.

According to some embodiments of the invention, at least one of the heavy chains is attached to an identifiable moiety.

According to some embodiments of the invention, the antibody is selected from the group consisting of a primate antibody, a porcine antibody, a murine antibody, a bovine antibody, a goat antibody and an equine antibody.

According to some embodiments of the invention, the host cells comprise bacterial cells.

According to some embodiments of the invention, the host cells comprise mammalian cells.

According to some embodiments of the invention, the expression takes place in inclusion bodies of the bacterial cells.

According to some embodiments of the invention, each of the nucleic acid molecules are transfected into different host cells.

According to some embodiments of the invention, each of the nucleic acid molecules are transfected into the same host cell.

According to some embodiments of the invention, the bacterial cells comprise gram negative bacterial cells.

According to some embodiments of the invention, the method further comprises purifying the antibody on Protein A/G/L following step (f).

According to some embodiments of the invention, the inflammatory disorder is cancer.

According to some embodiments of the invention, the inflammatory disease or disorder is cancer.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
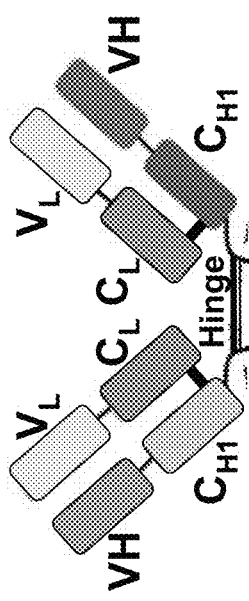
Figure 1B:
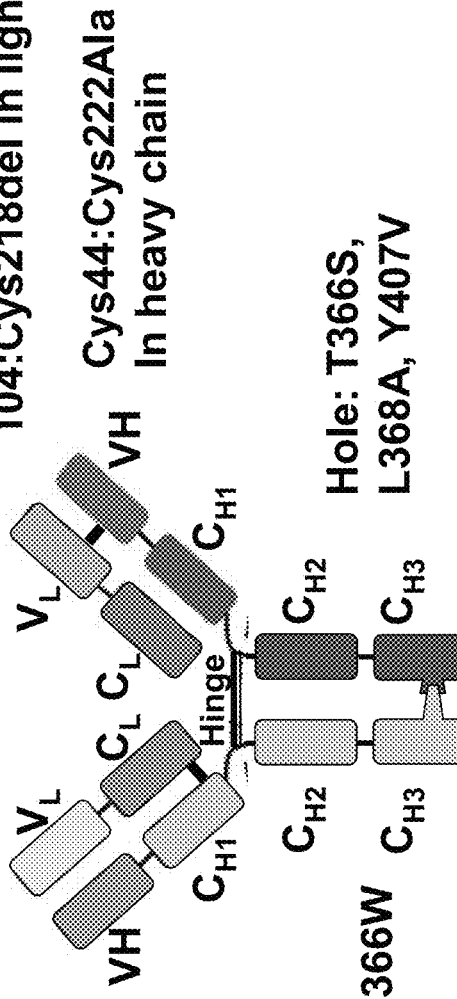
Figure 2B:
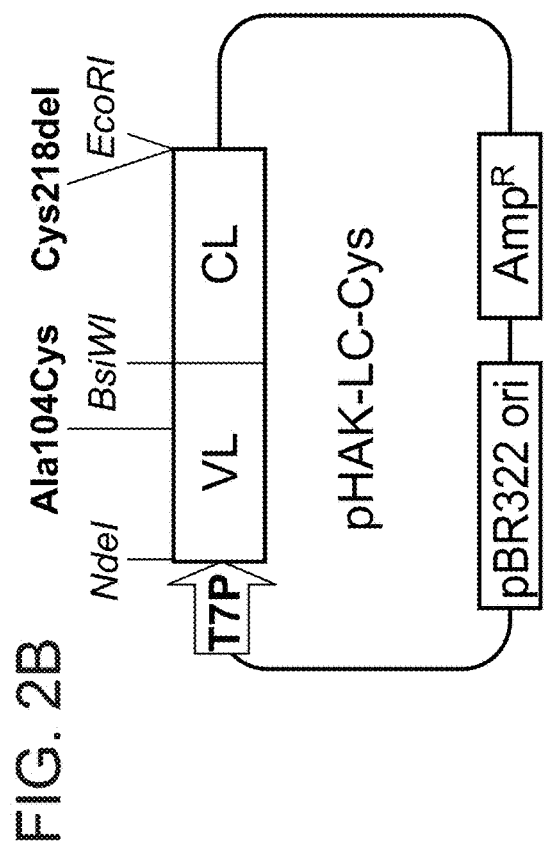
Figure 2D:
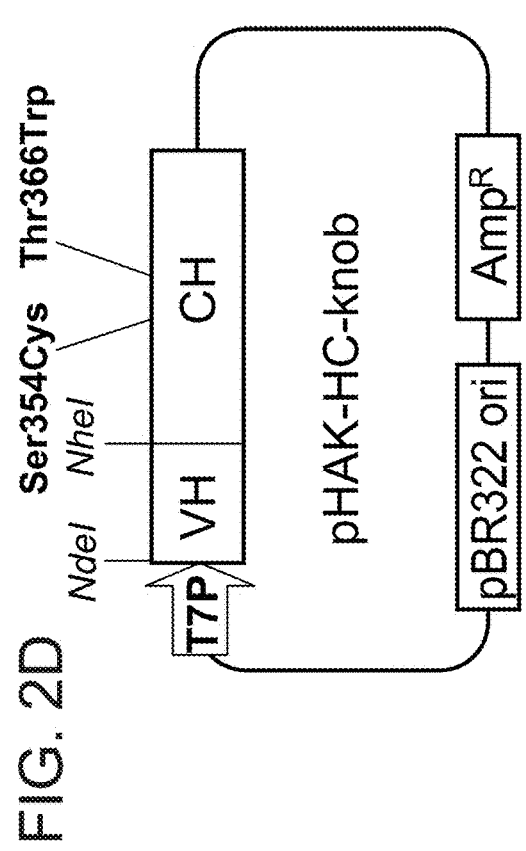
Figure 2A:
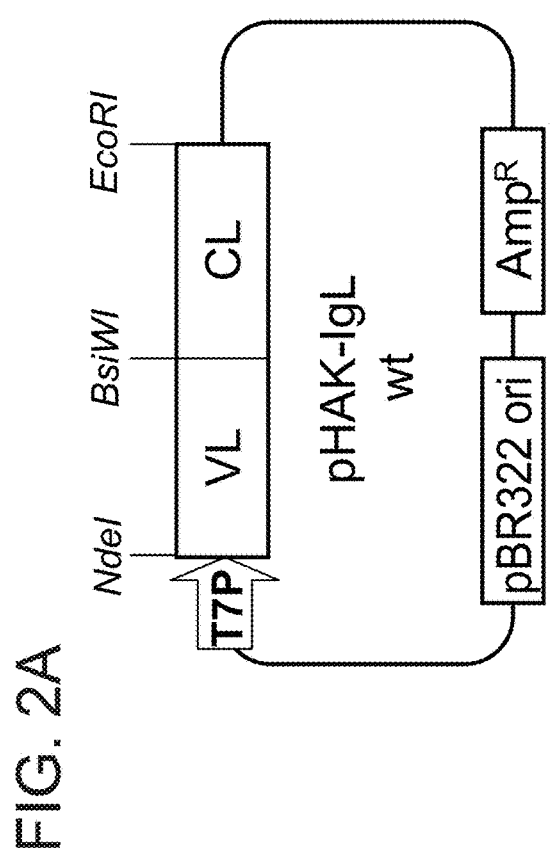
Figure 2C:
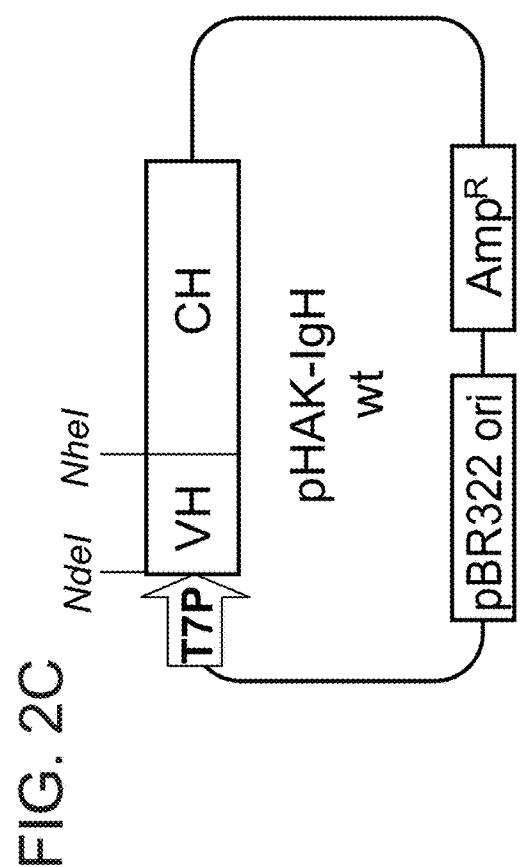
Figure 2E:
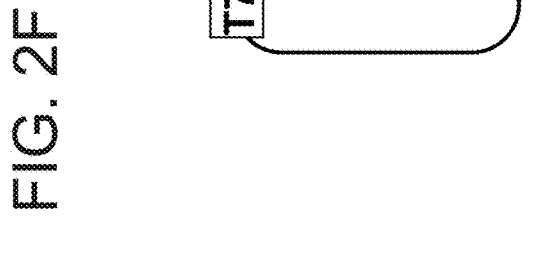
Figure 2F:
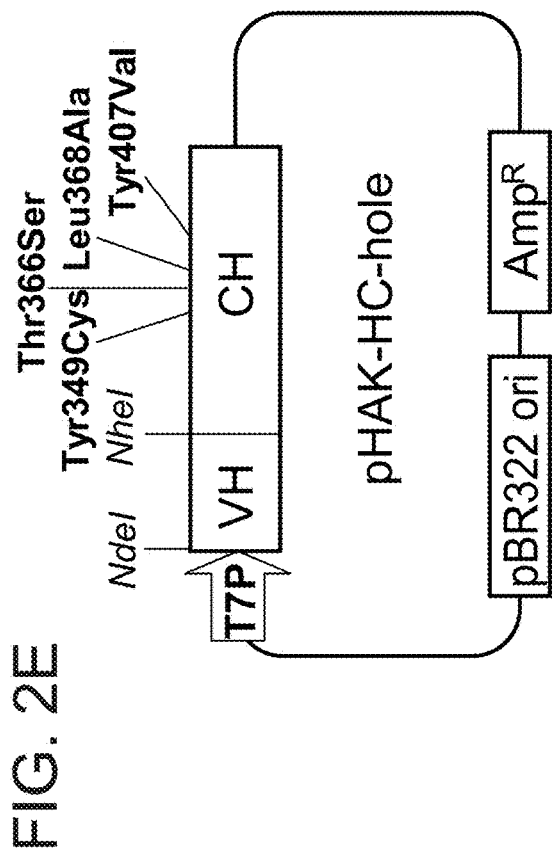
Figure 2G:
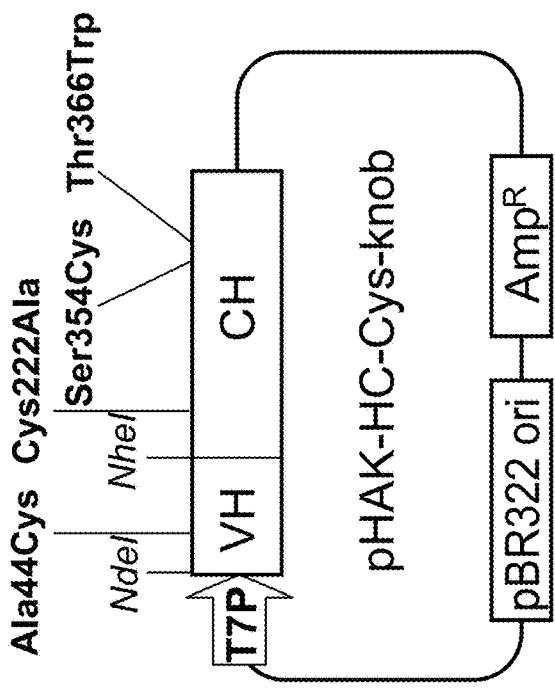
Figure 2H:
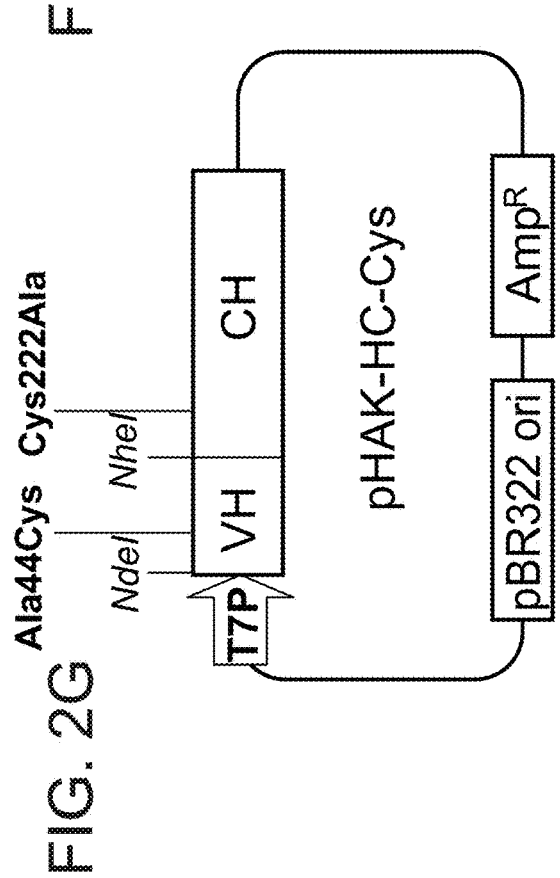

FIGS. 1A-1B are schematic structure of a novel strategy for production of bispecific antibodies. (A) scheme of an IgG antibody produced by the knobs into holes approach, there are two different heavy chains but a common light chain. (B) scheme of a bispecific antibody prepared according to embodiments of the present invention. There are two different heavy chains, each paired to its cognate light chain. The "knob" mutation corresponds to T366W, the "hole" mutations correspond to T366S, L368A Y407V replacements. Cysteine replacement mutations S354C and Y349C at CH3 region of "knob" or "hole" heavy chain, respectively, provide 95% heterodimerization (Merchant et al., 1998).

FIGS. 2A-2H are schematic representation of pHAK-IgH- and pHAK-IgL-based plasmid maps for expression of mono- and bispecific antibodies in *E. coli*: pHAK-IgL for expression of antibodies with human κ or λ light chain, pHAK-LC-Cys for expression of light chains containing dsFv-like intrachain disulfide bond, pHAK-IgH for expression of antibodies with human γ1 heavy chain, pHAK-HC-knob for expression of heavy chain containing S354C and T366W "knob" mutations in the constant region, pHAK-HC-hole for expression of heavy chain containing Y349C, T366S, L368A and Y407V "hole" mutation in constant region, pHAK-HC-hole-PE38 for expression of heavy chain containing "hole" mutations fused to a truncated form of *Pseudomonas* exotoxin A (PE38), pHAK-HC-Cys for expression of heavy chain containing dsFv-like disulfide intrachain bond, pHAK-HC-Cys-knob for expression of heavy chain containing "knob" mutations in constant region and dsFv-like intrachain disulfide bond.

Figure 3:
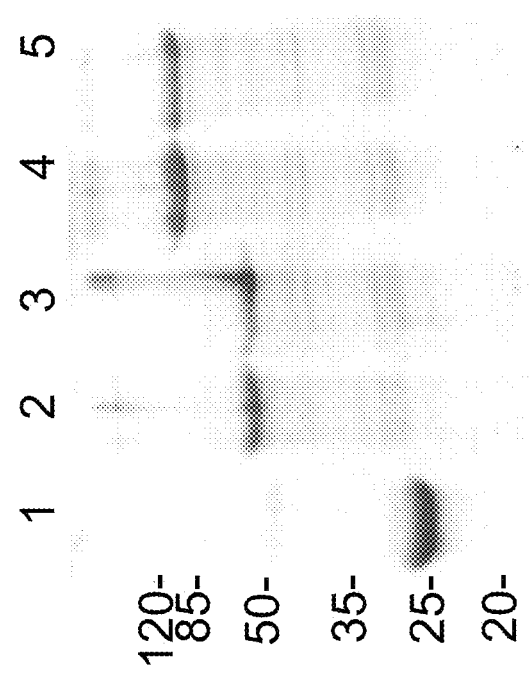

FIG. 3 is a photograph of SDS-PAGE analysis of heavy and light chains purification. The expressed proteins were collected as inclusion bodies, purified by sequential centrifugation steps and dissolved in a 6M guanidinium hydrochloride buffered solution. (1) T427 IgL, (2) T427 IgH, (3) T427-IgH-knob, (4) T427-IgH-PE38, (5) T427-IgH-hole-PE38. "Knob" mutations correspond to S354C:T366W. "Hole" mutations correspond to Y349C:T366S:L368A:Y407V.

FIGS. 4A-4B provide analysis of bispecific IgG-like proteins. (A) The schematic structures of IgG heavy and light chains and the theoretically possible IgG molecules that can be formed. Each variant can be easily detected according the significant differences in molecular weight. (B) SDS-PAGE (10% acrylamide) analysis of protein A purified products: wt T427 antibody displaying PE38 on heavy chain (1), "knobs-into-holes" version (2) of T427 antibody (S354C:T366W/Y349C:T366S:L368A:Y407V mutations), wt FRP5 antibody (3).

FIGS. 5A-5B provide SDS-PAGE (10% acrylamide) analysis of protein A purified products. (1) T427 "knob-knob" version (IgL+IgH-knob S354C:T366W mutations). (2) "Knobs-into-holes" version of T427 antibody (S354C: T366W/Y349C:T366S:L368A:Y407V mutations). (3) T427 "hole-hole" version (IgL+IgH-hole-PE38 Y349C:T366S:

L368A:Y407V mutations). (4) wt T427 antibody displaying PE38 on heavy chain. (M) Marker.

Figure 6:
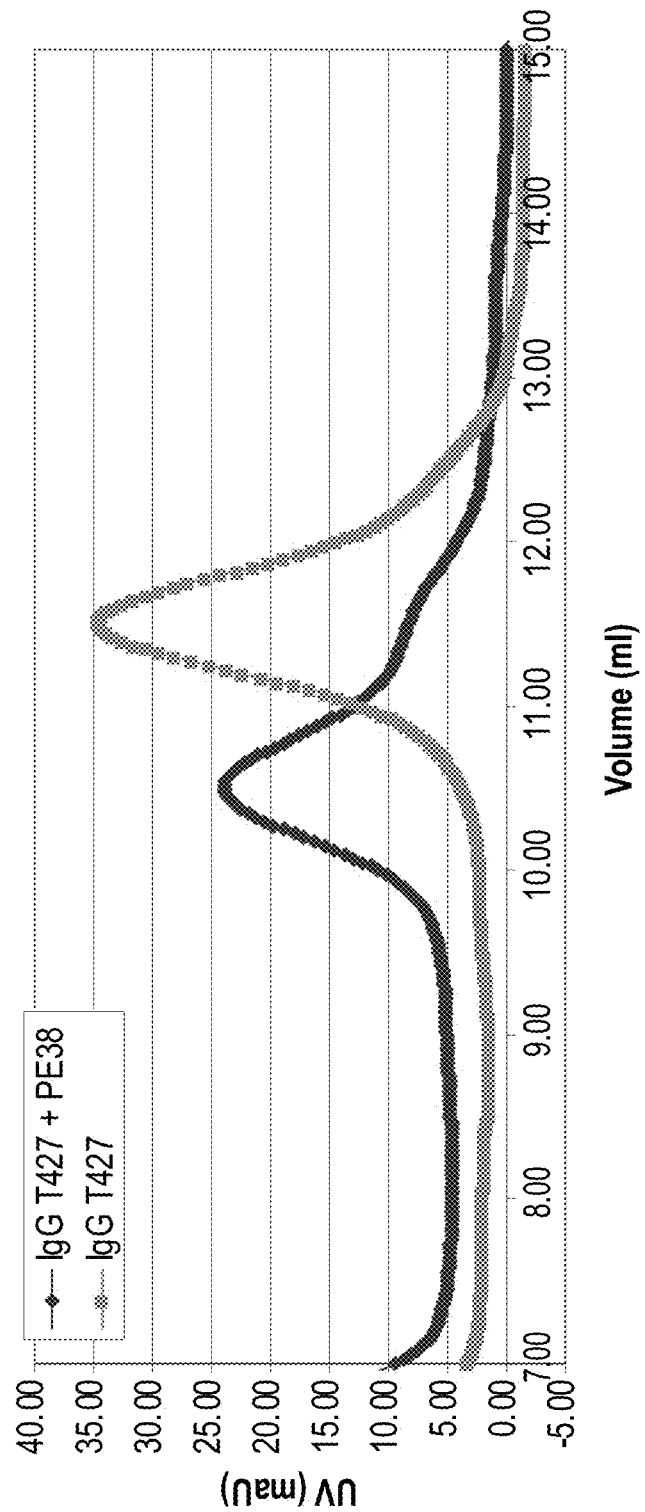

FIG. 6 shows a gel filtration analysis of IgG and IgG-like proteins. T427 IgG antibody (150 kDa) elutes the Sephadex 200 gel filtration column at 11.5 min. The IgG-like T427 heterodimer (2 IgL+IgH-knob+IgH-hole-PE38), 190 kDa elutes at 10.3 min. The small fraction of knob-knob homodimer (150 kDa) elutes at 11.5 min. The hole-hole homodimer (230 kDa) probably elutes at void volume (6.5 min (not shown)).

FIGS. 7A-7C illustrate SDS-PAGE (7.5% acrylamide) and density analysis of protein A purified products. (A) SDS-PAGE analysis of T427 IgG wt (1), T427-knob-hole-PE38 (2) and T427-PE38 (3) proteins. (B) Protein band density analysis of SDS-PAGE by ImageMaster 1D scanning laser densitometry. (C) The pie chart of the heterodimerization yield was measured according the pixel intensity at band position. T427-knob-hole-PE38 (2) consists of 2IgL+IgH-knob+IgH-hole-PE38. T427-PE38 (3) consists of 2IgL+2IgH-PE38. "Knob" mutations correspond to S354C:T366W. "Hole" mutations correspond to Y349C:T366S:L368A:Y407V.

FIGS. 8A-8B illustrate ELISA analysis of IgG and IgG-like proteins. The binding ability of FRP5 IgG and bispecific FRP5-T437-PE38 (PE38 fused to T427 heavy chain). (A) The ELISA plate was coated with erbB2 (antigen of FRP5 antibody) and antibodies were detected with anti-human secondary antibody. (B) The ELISA plate was coated with erbB2 (antigen of FRP5 antibody) and antibodies were detected with anti-PE secondary antibody (detection of bispecific antibodies).

The FRP5-T427-PE38 antibody consists of IgL-FRP5+IgL-T427+IgH-FRP5-knob+IgH-T427-hole-PE38 proteins. "Knobs-into-holes" mutations: S354C:T366W/Y349C:T366S:L368A:Y407V.

FIGS. 9A-9B illustrate SDS-PAGE (12% and 6% acrylamide) analyses of protein A purified IgG and IgG-like proteins. (1) FRP5 IgG wt. (2) T427 IgG wt. (3) T427 IgG-Cys (IgH-Cys44:Cys222Ala+IgL-Cys104:Cys218del). (4) Bispecific T427-FRP5 IgG (IgH-FRP5-hole+IgL-FRP5+IgH-T427-khob-Cys44:Cys222Ala+IgL-T427-Cys104:Cys218del) IgG. "Knob" mutations correspond to S354C:T366W. "Hole" mutations correspond to Y349C:T366S:L368A:Y407V.

FIG. 10 is an SDS-PAGE (10% acrylamide) analysis of protein A purified IgG and IgG-like proteins. (1) T427 IgG wt. (2) Anti-Tac IgG wt. (3) T427 IgG-Cys control A (IgH wt+IgL-Cys104:Cys218del). (4) T427 IgG-Cys control B (IgH-Cys44:Cys222Ala+IgL wt).

FIG. 11 is an SDS-PAGE analysis of heavy and light chains of αPE (B11), T427 and αSA antibodies purified as inclusion bodies and resuspended in 6 M guanidinium hydrochloride. The samples were separated in reducing condition on 12% acrylamide gel.

Figure 12A:
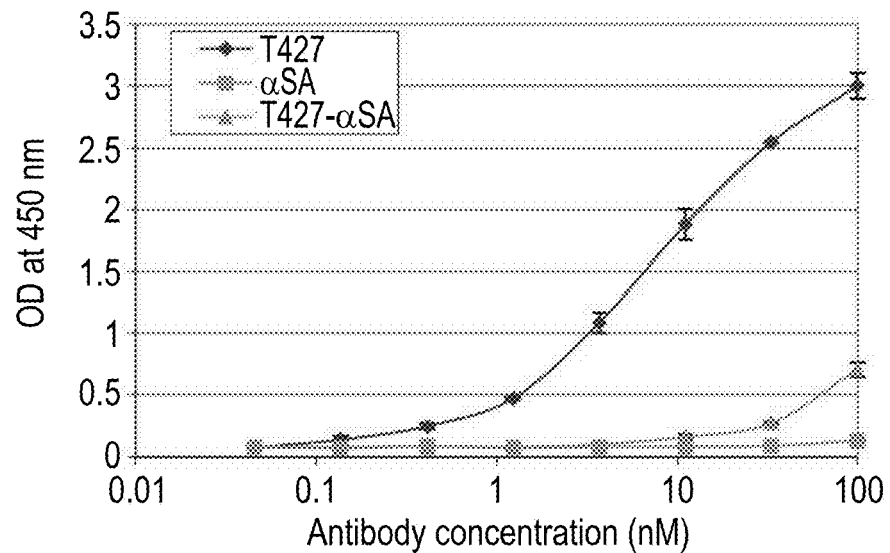
Figure 12B:
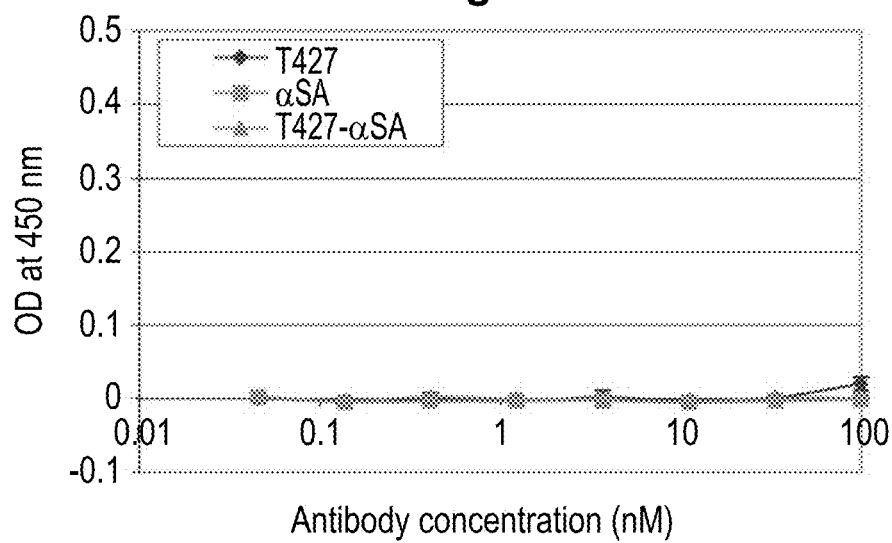

FIGs. 12A-12B is ELISA analysis of αSA (anti-streptavidin) antibodies. The T427, αSA (monoclonal) and T427-αSA (bispecific) protein A purified antibodies were analyzed for their ability to bind CD30 (A). The binding was detected using goat-anti-human HRP conjugated antibodies. Coating with bovine serum albumin (BSA) served as a control (B).

FIGS. 13A-13C is an ELISA analysis of αPE (anti-*Pseudomonas exotoxin* 38 kDa fragment) antibodies. The T427, αPE B11 clone (monoclonal) and T427-αPE (bispecific) protein A purified antibodies were analyzed for their ability to bind avitag-PE38 (A) and dsFv-PE38 (B) antigens. The binding was detected using goat-anti-human HRP conjugated antibodies. Coating with bovine serum albumin (BSA) served as a control (C).

Figure 14:
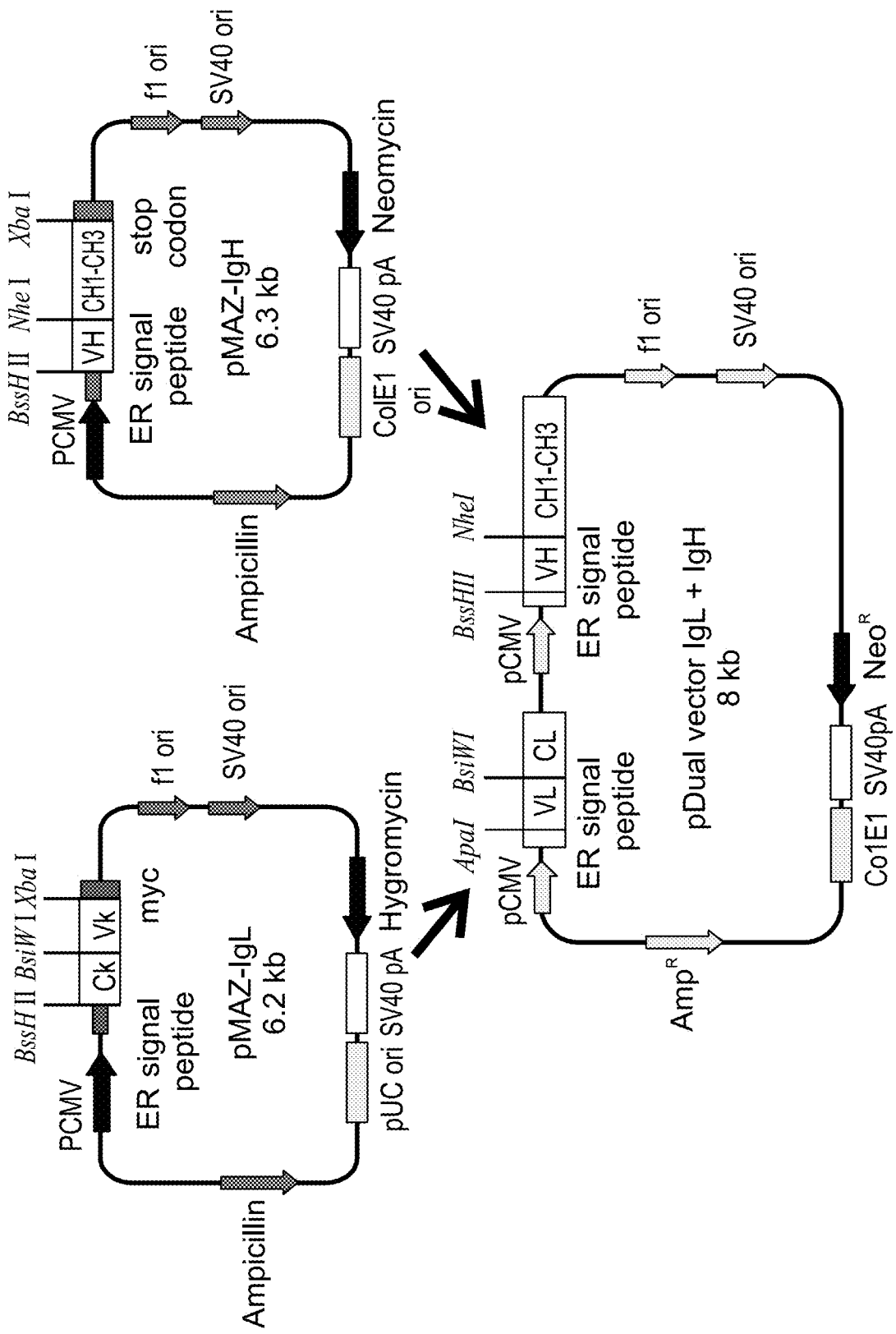

FIG. 14 is a schematic presentation of pDual vector system. pDual vectors are bi-cistronic, CMV promoter-based plasmids for the expression of IgGs in mammalian cells. They were constructed by combining heavy and light chain expression cassettes from the pMAZ vectors (Mazor Y, J Immunol Methods. 2007 Apr. 10; 321(1-2):41-59).

Figures 15A, 15B:
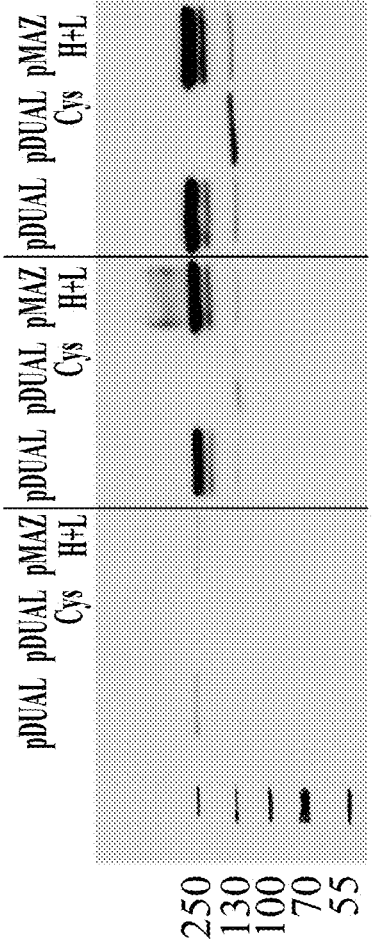

FIGS. 15A-15B illustrate analyses of secreted IgG in medium of $CaCl_2$ transfected 293 Trex cells. (A) Western blot analysis of cell media transfected with pDual wt, pDual L(Cys)+H(wt) or pMAZ-IgL+pMAZ-IgH vectors systems. The antibodies were detected with goat-anti-human HRP conjugated secondary antibody.

The antibody concentration in media was determined in comparison to the secondary dilutions of Erbitux antibody (B).

Figure 16:
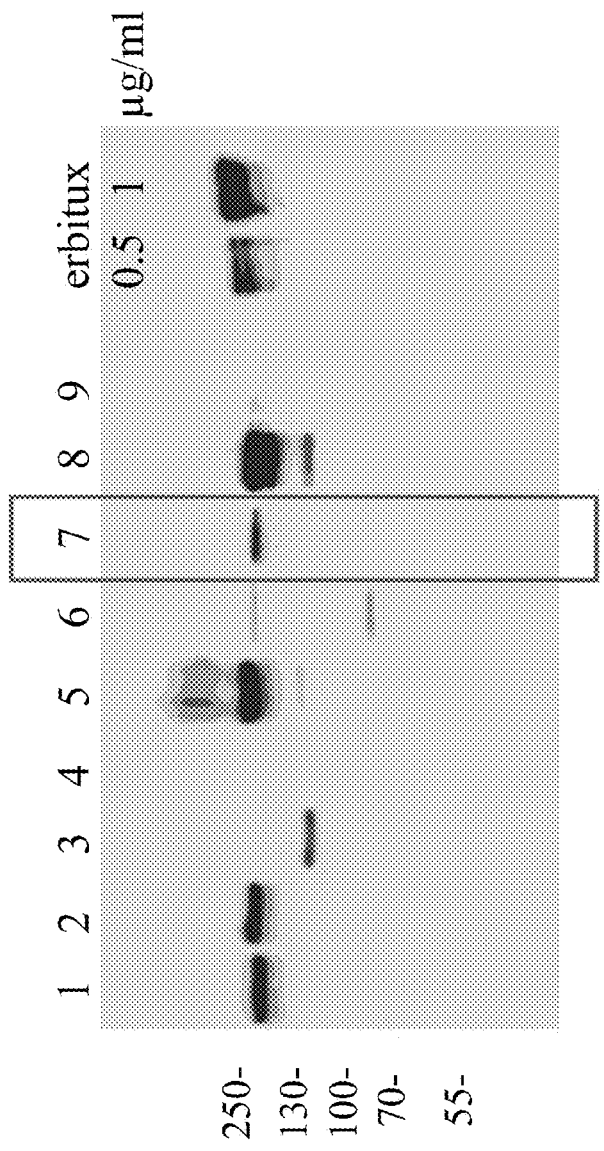

FIG. 16 illustrates a Western blot analysis of 293 Trex cells transfected with pDual mono-specific and bispecific vectors or combination of vectors. The antibodies were detected with goat-anti-human HRP conjugated antibody.

Figure 17:
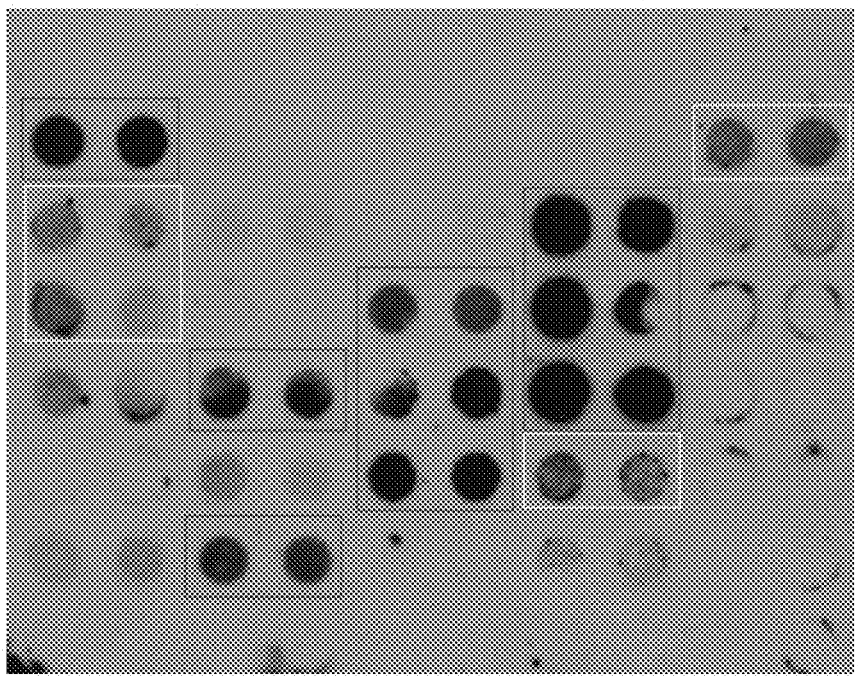

FIG. 17 illustrates exemplary results from a Dot blot analysis of antibody secreting clones. The cell media were absorbed to nitrocellulose membrane and antibodies were detected with goat-anti-human HRP conjugated antibody. The secretion level was determined relatively to other clones. The cell media of non-treated cells served as control.

Figure 18A:
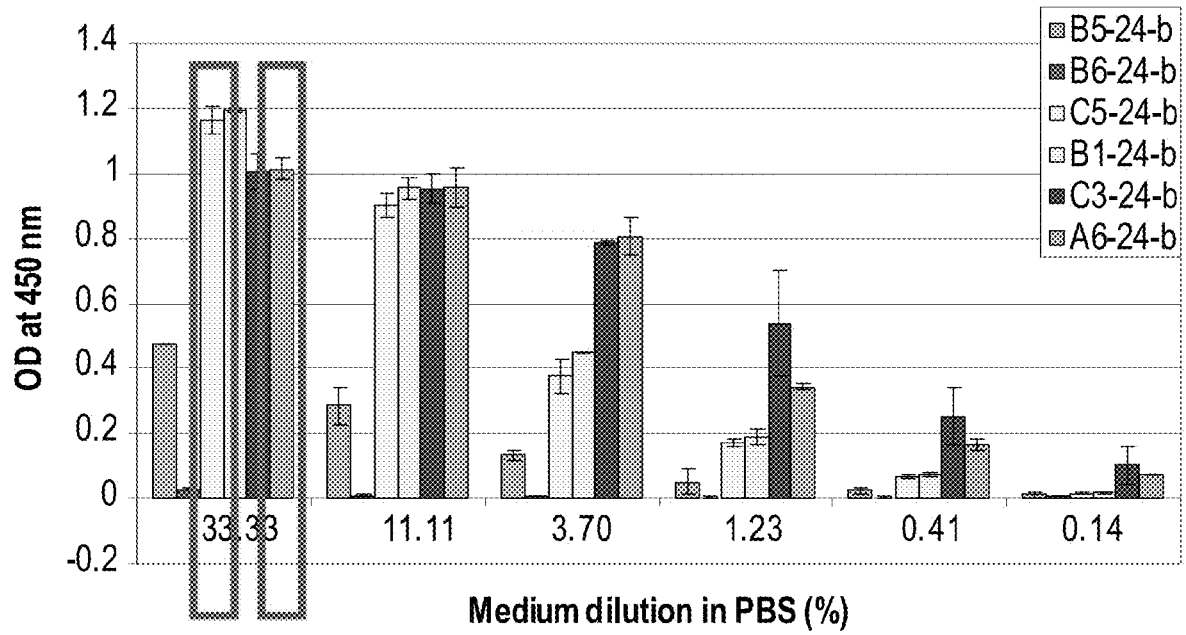
Figure 18B:
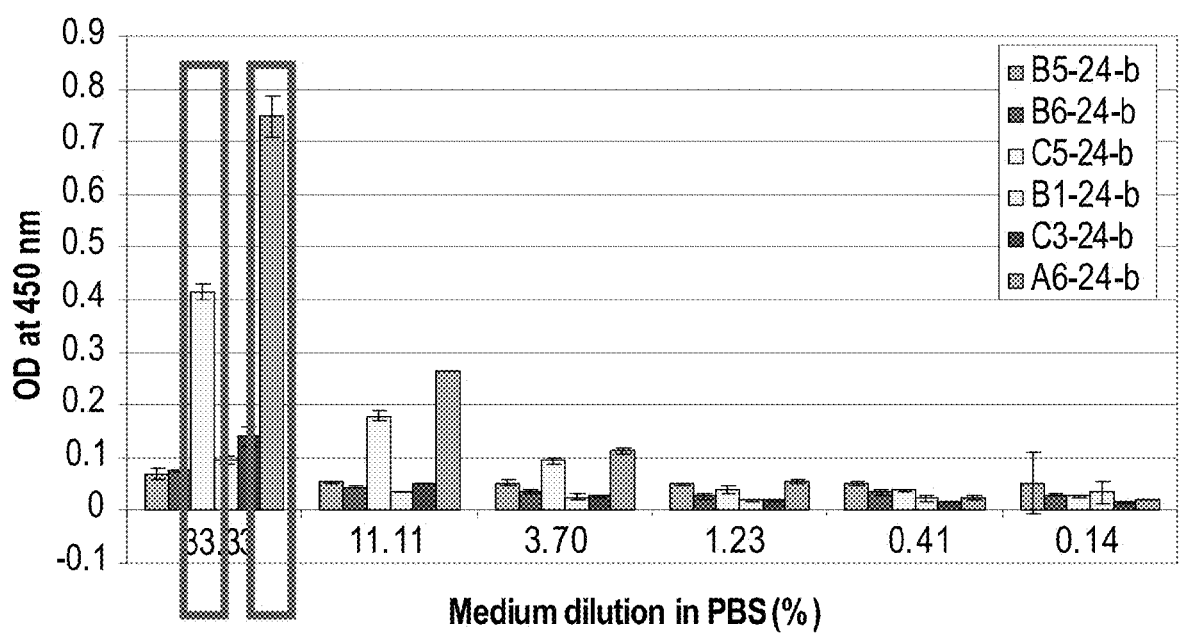

FIGS. 18A-B illustrate validation of binding activity of bispecific clones. The cell media were incubated with either erbB2 (18A) or CD30 (18B) antigens. The binding was detected with goat-anti-human HRP conjugated antibody. The marked clones demonstrated the binding ability to both antigens.

Figures 19A, 19B:
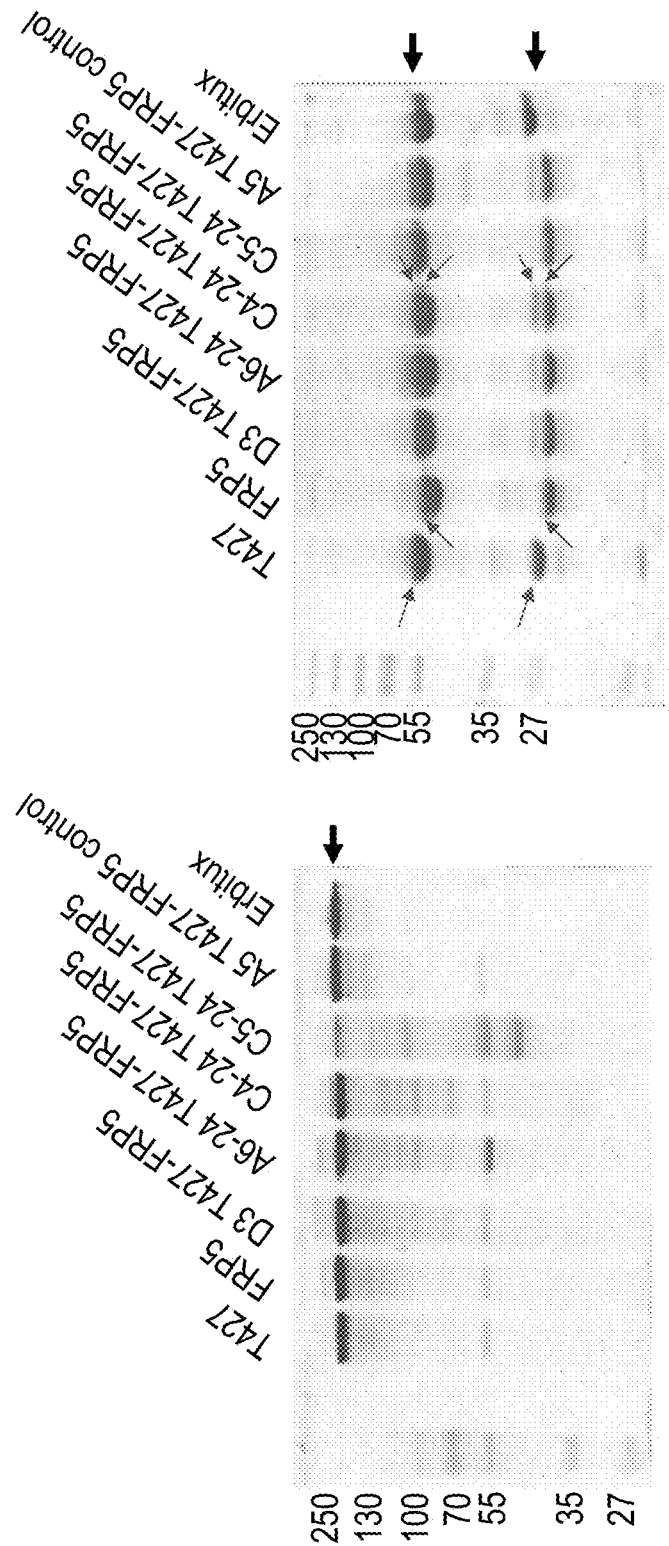

FIGS. 19A-19B illustrates an SDS-PAGE analysis of IgGs produced in HEK 293 T-REx™ mammalian cells followed by protein A purification. The proteins were separated in unreduced conditions on 10% acrylamide gel in order to evaluate the 150 kDa IgGs (A) and in reduced conditions on 12% acrylamide gel (B) in order to evaluate the minimal differences between T427 and FRP5 heavy chains and light chains and determine the double bands in bispecific T427-FRP5 molecules.

Figure 20A:
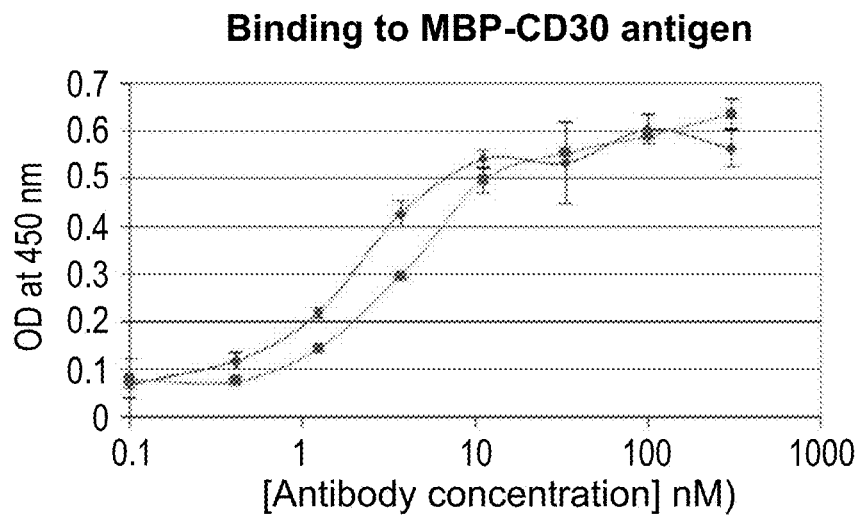
Figure 20B:
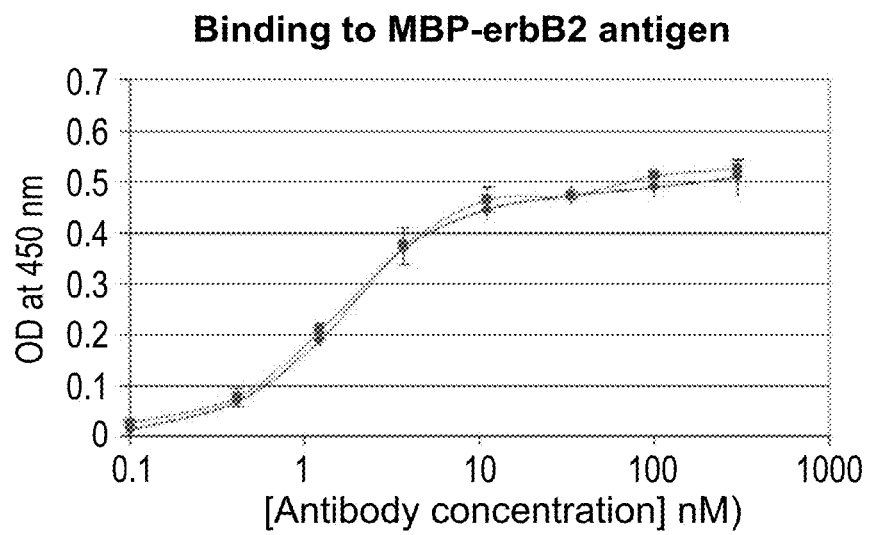

FIGS. 20A-20B illustrate ELISA analysis of protein A purified IgGs produced in mammalian cells. A5 is a control cell line transfected with four plasmids, two encoding the monospecific T427 antibody and two encoding the monospecific FRP5 antibody. Bispecific T427-FRP5 represents bispecific antibody secreting stable clone D3 with monovalent binding ability to each antigen (erbB2 and CD30). The binding was detected using goat-anti-human HRP conjugated secondary antibody.

Figure 21A:
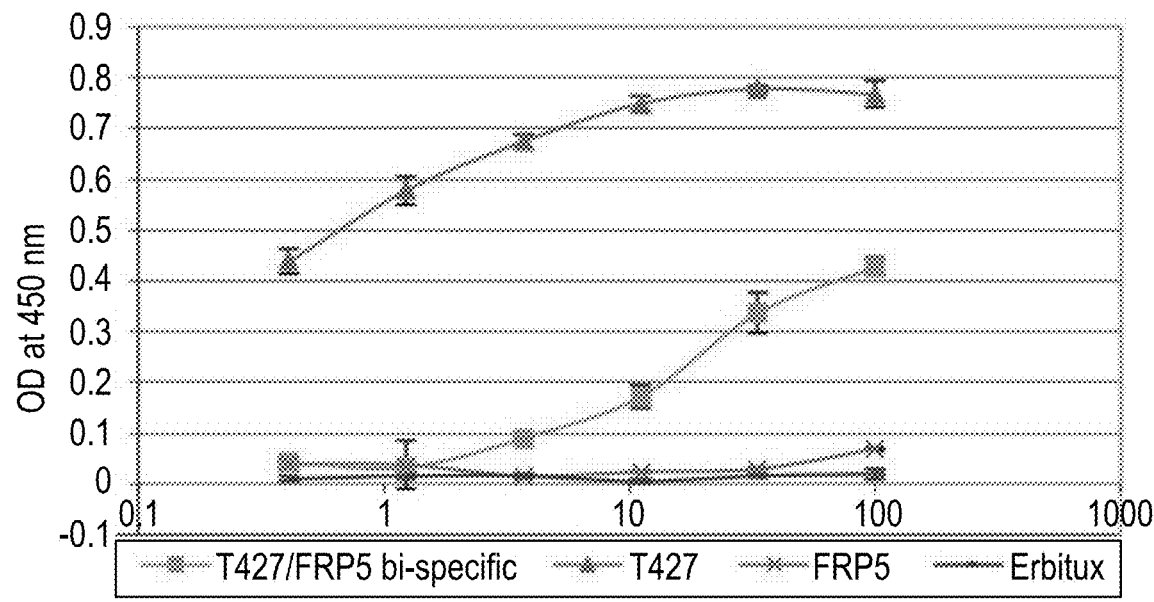
Figure 21B:
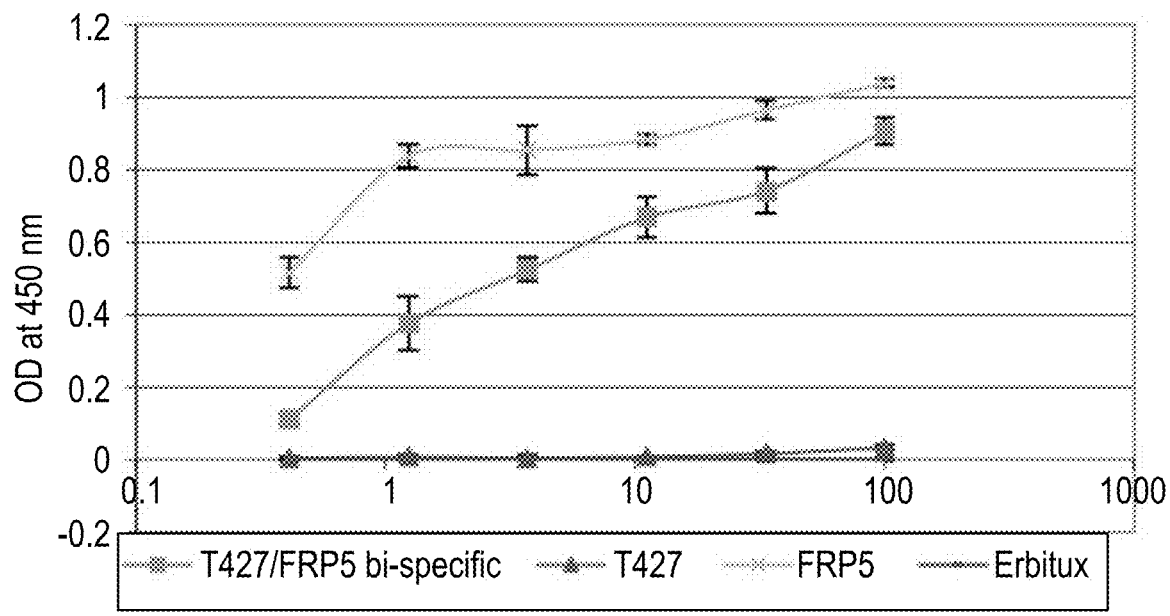

FIGS. 21A-21B are graphs illustrating ELISA analysis of protein A purified IgGs produced in mammalian cells. T427 and FRP5 represent mono-specific antibodies with bi-valent binding activity. Bispecific T427-FRP5 represents bispecific antibody-secreting stable clone D3 with mono-valent binding ability to each antigen (erbB2 and CD30). Erbitux served as a negative control. The binding was detected using goat-anti-human HRP conjugated secondary antibody.

Figure 22:
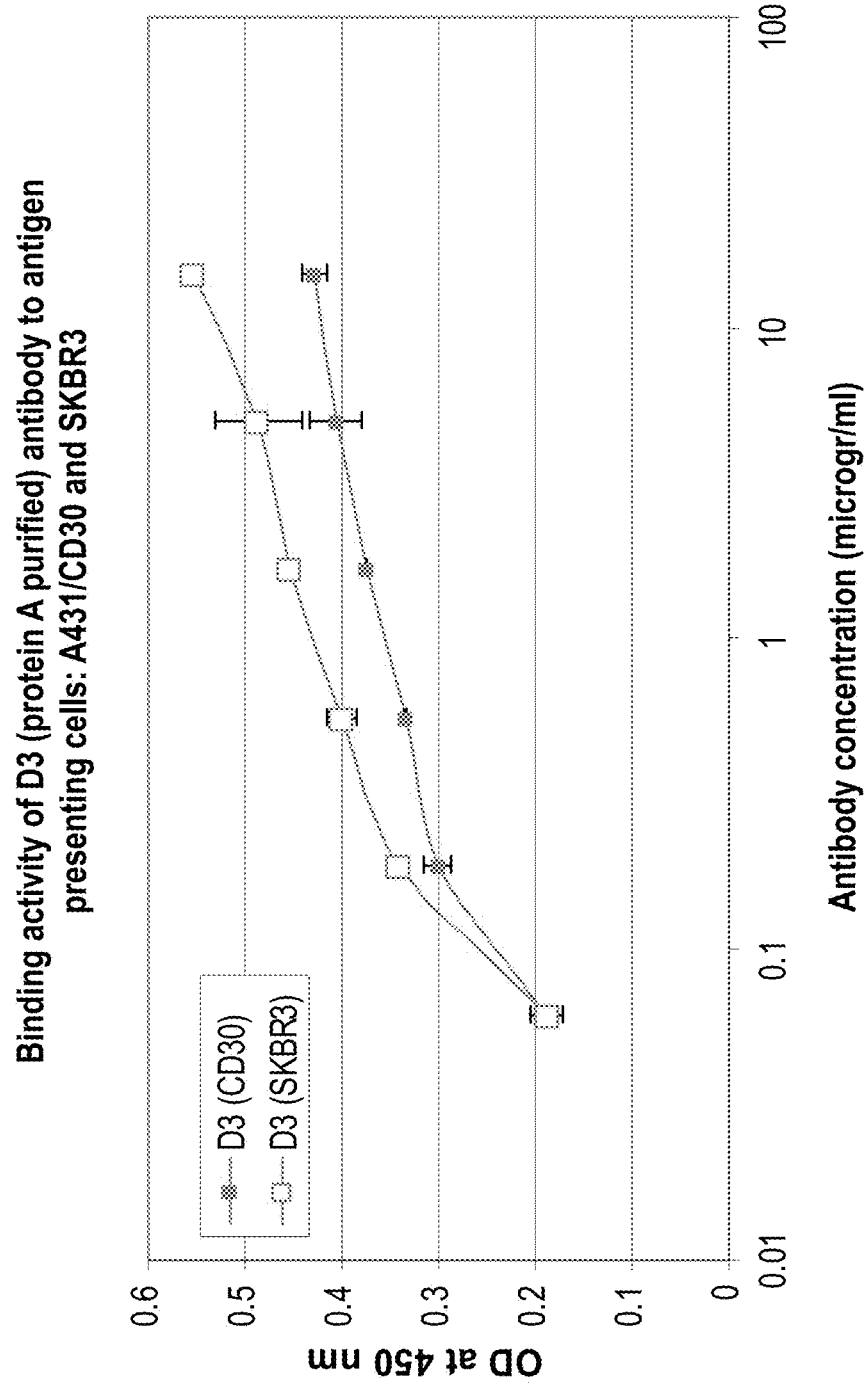

FIG. 22 is a graph illustrating cell-ELISA analysis of binding ability of B3 clone secreting T427-FRP5 bispecific antibody, (protein A-purified from conditioned medium of the stable clone) to A431/CD30 and SKBR3 (erbB2+) cells. The binding was detected using goat-anti-human HRP conjugated secondary antibody.

Figure 23:
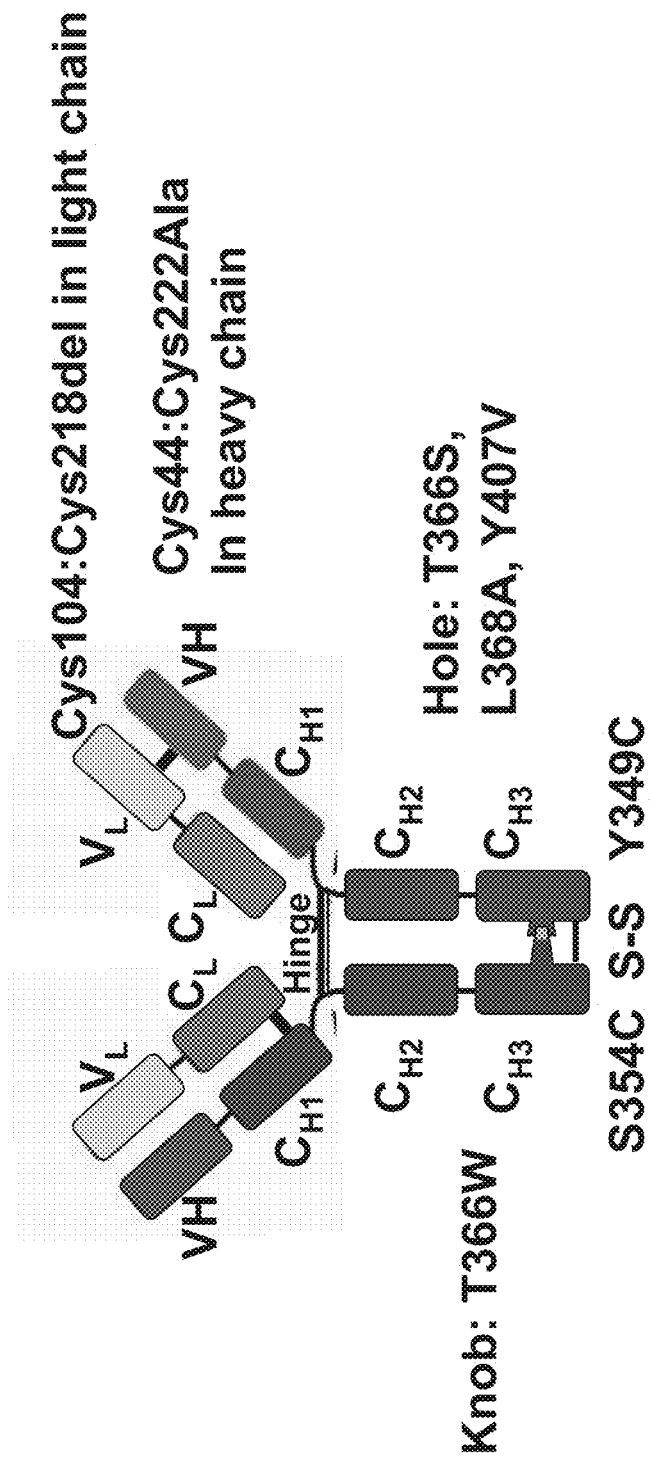

FIG. 23 is a schematic representation of the monospecific antibody of embodiments of the present invention.

FIG. 24 is ELISA analysis of T427 KIH. The binding ability of T427 IgG and T427-PE38 (PE38 fused to heavy chain) in comparison to knobs-into-holes (KIH) version of T427 antibody (2×IgL+IgH-knob+IgH-hole-PE38).

DESCRIPTION OF SPECIFIC EMBODIMENTS OF THE INVENTION

The present invention, in some embodiments thereof, relates to bispecific antibodies, monospecific antibodies, asymmetric antibodies and methods of generating same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

In past years, both laboratory and early clinical studies have demonstrated that bispecific antibodies (BsAbs) may have significant potential application in cancer therapy either by targeting tumor cells with cytotoxic agents including effector cells, radionuclides, drugs, and toxins, or by simultaneously blocking two relevant tumor targets, that is, growth factor receptors or their ligands, thus neutralizing multiple receptor activation and downstream signal transduction pathways. A major obstacle in the development of BsAb has been the difficulty of producing the materials in sufficient quality and quantity by traditional technologies such as the hybrid hybridoma and chemical conjugation methods. Thus, it is believed that the development of IgG-like BsAbs as therapeutic agents will depend heavily on the advances made in the design of recombinant BsAb constructs and production efficiency.

In order to ensure heterodimerization between the heavy chains of antibodies "A" and "B" to form, and to prevent homodimerization of antibody "A" to antibody "A" and antibody "B" to antibody "B", a knob and hole approach has been suggested, as disclosed in U.S. Pat. No. 7,183,076. However, the knobs into holes approach provides a solution only for the heteroassociation of the heavy chains and does not provide one for the correct pairing of each heavy chain with its cognate light chain.

The present invention relates to an approach of efficient assembly of bispecific antibodies in an IgG format. The approach involves heterodimerization of the two heavy chains by applying the knobs into holes approach, combined with facilitation of pairing of each heavy chain with only its cognate light chain.

The present inventors suggest pairing the heavy and light chains of the same antibody using one native CH1-CL binding disulfide bond and one non-native $V_H$-$V_L$ binding dsFv-like di-sulfide bond (as illustrated in FIG. 1B). This way one antibody branch would stay molecularly untouched while the other antibody branch would acquire a new disulfide covalent bond in variable region instead of the wt S—S bond. The mis-paired light and heavy chains would not form the S—S stabilized interface and would not produce stable IgG molecule. Thus this strategy supposes the conversion of one antibody branch into dsFv-like molecule without any affinity or stability loss.

Whilst reducing the present invention to practice, the present inventors generated a bispecific antibody by combining an anti-CD30 (T427) and an anti-erbB2 (FRP5) antibody. In the erbB2 antibody, heavy-light chain association was facilitated by the natural disulfide bond that covalently links the $C_H1$ domain of the heavy chain with the $C_L$ domain of the light chain. In the anti-CD30 antibody, the cysteine in $C_H1$ was mutated to alanine and the C-terminal cysteine of $C_L$ was deleted, preventing the formation of the native H-L disulfide bond. Instead of the eliminated disulfide bond, two cysteines, one in the variable domain of the heavy chain and one in the variable domain of the light chain were introduced according the rules of disulfide-stabilized Fv fragments (dsFvs). As a result, the heavy and light chains of the anti-CD30 antibody associated covalently via a disulfide bond that forms between $V_H$ and $V_L$ through these two cysteine residues. Thus, the present invention contemplates both the generation of a novel disulfide bridge between the heavy chain and its cognate light chain on one arm of the bifunctional antibody and so as to further enhance correct assembly, deletion of the naturally occurring disulfide bridge between the same heavy chain with its cognate light chain.

As illustrated in FIGS. 9A-B, using this approach, full-length bifunctional antibodies were generated in bacterial cells. When the heavy and light chains of the anti-CD30 antibody were not mutated as described above, full length bifunctional antibodies were not generated (FIG. 10).

Further, using bispecific vectors, the present inventors showed that the generation of full-length bifunctional antibodies in mammalian cells was promoted by applying the knobs into holes approach, combined with facilitation of pairing of each heavy chain with only its cognate light chain (as illustrated in FIGS. 17-22).

Thus, according to an aspect of the present invention there is provided an antibody comprising an Fc region and a Fab region, wherein:

(i) the Fc region comprises two non-identical heavy chains, wherein at least one of the two non-identical heavy chains comprises an amino acid modification so as to form complementation between the two non-identical heavy chains thereby increasing the probability of forming heterodimers of the non-identical heavy chains and decreasing the probability of forming homodimers of identical heavy chains; and (ii) the Fab region comprises a first covalent link between a first heavy chain and a first light chain of the Fab region and a second covalent link between a second heavy chain and a second light chain of the Fab region, wherein a position of the first covalent link relative to the first heavy chain is different to a position of the second covalent link relative to the second heavy chain.

An antibody is characterized by a centrally placed disulfide bridge that stabilizes a series of antiparallel beta strands into an immunoglobulin-like fold. An antibody heavy or light chain has an N-terminal ($NH_2$) variable region (V), and a C-terminal (—COOH) constant region (C). The heavy chain variable region is referred to as $V_H$, and the light chain variable region is referred to as $V_L$. $V_H$ and $V_L$ fragments together are referred to as "Fv". The variable region is the part of the molecule that binds to the antibody's cognate antigen, while the constant region determines the antibody's effector function (e.g., complement fixation, opsonization). Full-length immunoglobulin or antibody "light chains" (generally about 25 kilodaltons (Kd), about 214 amino acids) are encoded by a variable region gene at the N-terminus (generally about 110 amino acids) and a constant region gene at the COOH-terminus. Full-length immunoglobulin or antibody "heavy chains" (generally about 50 Kd, about 446 amino acids), are similarly encoded by a variable region gene (generally encoding about 116 amino acids) and one of the constant region genes (encoding about 330 amino acids). An antibody light or heavy chain variable region comprises three hypervariable regions, also called complementarity determining regions or CDRs, flanked by four relatively conserved framework regions or FRs.

According to one embodiment of this aspect of the present invention the antibody is a bispecific antibody.

As used herein, the term "bispecific antibody" refers to an antibody which comprises two antigen binding sites, each binding to a different epitope of an antigen. The bispecific antibodies of this aspect of the present invention do not share common light chains nor common heavy chains.

According to one embodiment, the two antigen binding sites each bind to different epitopes of an identical antigen. According to another embodiment, the two antigen binding sites each bind to different epitopes on different antigens.

According to another embodiment of this aspect of the present invention, the antibody is a monospecific, asymmetric antibody.

The monospecific antibodies of this aspect of the present invention have the same paratope on both arms which bind an identical antigen. However, unlike conventional monoclonal antibodies which are symmetric assemblies of two identical heavy chains and two identical light chains, monospecific antibodies described herein are asymmetric assemblies of two non-identical heavy chains and two non-identical light chains. The differences between the two heavy chains and between the two light chains are in the constant domains and in framework regions of the variable domains that allow heterodimerization of the chains. Accordingly, the CDR loops of the variable domains and supporting variable domain residues that may comprise the paratope are identical in the chain pairs—see FIG. 23.

According to a particular embodiment, the monospecific antibody is an IgG4.

Preferably, the affinity of each of the antigen binding sites of the antibody for its target is not substantially reduced as compared with one arm of its corresponding monoclonal antibody for the identical target. According to a specific embodiment, the affinity is not reduced more than 100 fold, more preferably is not reduced more than 50 fold, more preferably is not reduced more than 20 fold, more preferably is not reduced more than 10 fold and even more preferably is not reduced more than 5 fold.

Examples of bispecific antibodies include those with one antigen binding site directed against a first growth factor ligand and a second antigen binding site directed against a second growth factor ligand; one antigen binding site directed against a first growth factor receptor and a second antigen binding site directed against a second growth factor receptor; one antigen binding site directed against a first cytokine and a second antigen binding site directed against a second cytokine; one antigen binding site directed against a first cytokine receptor and a second antigen binding site directed against a second cytokine receptor; one antigen binding site directed against a growth factor receptor and a second antigen binding site directed against a growth factor ligand; one antigen binding site directed against a cytokine receptor and a second antigen binding site directed against a cytokine ligand. Additional combinations of growth factors, growth factor receptors, cytokines and cytokine receptors are also contemplated.

According to another embodiment, the bispecific antibody block two pathways of angiogenesis, one antigen binding site is directed towards a receptor or ligand associated with the first pathway and the other antigen binding site is directed towards a receptor or ligand associated with the second pathway.

According to a specific embodiment, the bispecific antibody comprises one antigen binding site directed against a tumor cell antigen and the other antigen binding site directed against a cytotoxic trigger molecule such as anti-Fcγ-RI/anti-CD15, anti-p185$^{HER2}$/Fcγ-RIII (CD16), anti-CD3/anti-malignant B-cell (1D10), anti-CD 3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3.

Bispecific antibodies with one antigen binding site binding specifically to a tumor antigen and one antigen binding site binding to a toxin include for example anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid.

Other contemplated bispecific antibodies include those for converting enzyme activated prodrugs such as anti-CD30/anti-alkaline phosphatase (which catalyzes conversion of mitomycin phosphate prodrug to mitomycin alcohol).

Other contemplated bispecific antibodies include those which can be used as fibrinolytic agents such as anti-fibrin/anti-tissue plasminogen activator (tPA), anti-fibrin/anti-urokinase-type plasminogen activator (uPA).

Additional contemplated bispecific antibodies include those for targeting immune complexes to cell surface receptors such as anti-low density lipoprotein (LDL)/anti-Fc receptor (e.g. Fcγ-RI, Fcγ-RII or Fcγ-RIII).

Additional contemplated bispecific antibodies include those for use in therapy of infectious diseases such as anti-CD3/anti-herpes simplex virus (HSV), anti-T-cell receptor:CD3 complex/anti-influenza, anti-FcγR/anti-HIV. Further bispecific antibodies for tumor detection in vitro or in vivo include anti-CEA/anti-EOTUBE, anti-CEA/anti-DPTA, anti-p185HER2/anti-hapten.

Bispecific antibodies may be used as vaccine adjuvants (see Fanger et al., Critical Reviews in Immunology 12(3, 4):101-124 (1992)).

Bispecific antibodies may be used as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase.

Additional contemplated bispecific antibodies include ones where the first antigen binding site binds CD30 and the second antigen binding site binds erbB2; ones where the first antigen binding site binds CD30 and the second antigen binding site binds *Pseudomonas Exotoxin* (PE); ones where the first antigen binding site binds CD30 and the second antigen binding site binds Streptavidin.

Examples of trispecific antibodies include anti-CD3/anti-CD4/anti-CD37, anti-CD3/anti-CD5/anti-CD37 and anti-CD3/anti-CD8/anti-CD37.

The Fc region of the antibodies of the present invention may be may be obtained from any antibody, such as IgG$_1$, IgG$_2$, IgG$_3$, or IgG$_4$ subtypes, IgA, IgE, IgD or IgM.

According to one embodiment, the Fc region is an IgG Fc region.

As mentioned, the Fc region of the antibodies described herein comprises two non-identical heavy chains (e.g. that differ in the sequence of the variable domains), wherein at least one of the two non-identical heavy chains comprises an amino acid modification so as to increase the probability of forming a stable heterodimer of the non-identical heavy chains and decrease the probability of forming a stable homodimer of identical heavy chains.

According to one embodiment, at least one heavy chain is genetically modified such that an altered charge polarity across the interface is created. As a consequence, a stable heterodimer between electrostatically matched Fc chains is promoted, and unwanted Fc homodimer formation is suppressed due to unfavorable repulsive charge interactions.

Determination of which amino acids to modify and to which amino acids is further explained in Gunasekaran K, Pentony M, Shen M, Garrett L, Forte C, Woodward A, Ng S B, Born T, Retter M, Manchulenko K, Sweet H, Foltz I N, Wittekind M, Yan W. Enhancing antibody Fc heterodimer formation through electrostatic steering effects: applications to bispecific molecules and monovalent IgG. J Biol Chem. 2010 Jun. 18; 285(25):19637-46. Epub 2010 Apr. 16, incorporated herein by reference.

According to one embodiment, the amino acid modifications (that affect charge complementarity) are effected at the rim of the interface between the two heavy chains and not in structurally conserved buried residues at the hydrophobic core of the interface.

According to another embodiment, at least one heavy chain is genetically modified, to generate a heavy chain with a 3D structure which binds more efficiently to the non-identical heavy chain (i.e. a heterodimer) as opposed to an identical heavy chain (i.e. a homodimer). The generation of heterodimers is encouraged due to steric complementation and the generation of homodimers is discouraged due to steric hindrance.

According to this embodiment, one heavy chain is genetically modified to generate a protuberance and the second heavy chain is genetically modified to generate a sterically compensatory cavity, the protuberance protruding into the compensatory cavity.

"Proturbances" are constructed by replacing small amino acid side chains from the interface of the first heavy chains with larger side chains (e.g. tyrosine, arginine, phenylalanine, isoleucine, leucine or tryptophan). Compensatory "cavities" of identical or similar size to the protuberances are optionally created on the interface of the second heavy chain by replacing large amino acid side chains with smaller ones (e.g. alanine, glycine, serine, valine, or threonine).

The protuberance or cavity can be "introduced" into the interface of the first or second heavy chain by synthetic means, e.g. by recombinant techniques, in vitro peptide synthesis, those techniques for introducing non-naturally occurring amino acid residues previously described, by enzymatic or chemical coupling of peptides or some combination of these techniques. According, the protuberance, or cavity which is "introduced" is "non-naturally occurring" or "non-native", which means that it does not exist in nature or in the original polypeptide (e.g. a humanized monoclonal antibody).

Preferably the import amino acid residue for forming the protuberance has a relatively small number of "rotamers" (e.g. about 3 6). A "rotamer" is an energetically favorable conformation of an amino acid side chain. The number of rotamers of the various amino acid residues are reviewed in Ponders and Richards, J. Mol. Biol. 193:775 791 (1987).

As a first step to selecting original residues for forming the protuberance and/or cavity, the three-dimensional structure of the antibodies are obtained using techniques which are well known in the art such as X-ray crystallography or NMR. Based on the three-dimensional structure, those skilled in the art will be able to identify the interface residues.

The preferred interface is the $C_{H3}$ domain of an immunoglobulin constant domain. It is preferable to select "buried" residues to be replaced. The interface residues of the CH3 domains of IgG, IgA, IgD, IgE and IgM have been identified (see, for example, PCT/US96/01598, herein incorporated by reference in its entirety), including those which are optimal for replacing with import residues; as were the interface residues of various IgG subtypes and "buried" residues. The preferred $C_{H3}$ domain is derived from an IgG antibody, such as an human $IgG_1$.

The $C_{H3}/C_{H3}$ interface of human $IgG_1$ involves sixteen residues on each domain located on four anti-parallel β-strands which buries 1090 $ANG^2$ from each surface. Mutations are preferably targeted to residues located on the two central anti-parallel β-strands. The aim is to minimize the risk that the protuberances which are created can be accommodated by protruding into surrounding solvent rather than by compensatory cavities in the partner $C_{H3}$ domain. Methods of selection particular sites on the heavy chains have been disclosed in U.S. Pat. No. 7,183,076, incorporated herein by reference.

According to a specific embodiment, the first heavy chain comprises a T366W mutation (i.e. threonine to tryptophan); and the second heavy chain comprises T366S, L368A, Y407V mutations (i.e. threonine to serine; leucine to alanine; and tyrosine to valine).

According to one embodiment, the amino acid modifications (that affect structural complementarity) are effected at structurally conserved buried residues at the hydrophobic core of the interface, and not in at the rim of the interface between the two heavy chains.

The effect of replacing residues on the heavy chains can be studied using a molecular graphics modeling program such as the Insight™ program (Biosym Technologies).

Once the preferred original/import residues are identified by molecular modeling, the amino acid replacements may be introduced into the heavy chains using techniques which are well known in the art.

Oligonucleotide-mediated mutagenesis is a preferred method for preparing substitution variants of the DNA encoding the first or second heavy chain. This technique is well known in the art as described by Adelman et al., DNA, 2:183 (1983). Briefly, first or second polypeptide-coding DNA is altered by hybridizing an oligonucleotide encoding the desired mutation to a DNA template, where the template is the single-stranded form of a plasmid or bacteriophage containing the unaltered or native DNA sequence of heteromultimer. After hybridization, a DNA polymerase is used to synthesize an entire second complementary strand of the template that will thus incorporate the oligonucleotide primer, and will code for the selected alteration in the heteromultimer DNA.

Cassette mutagenesis can be performed as described Wells et al. Gene 34:315 (1985) by replacing a region of the DNA of interest with a synthetic mutant fragment generated by annealing complimentary oligonucleotides. PCR mutagenesis is also suitable for making variants of the first or second polypeptide DNA. While the following discussion refers to DNA, it is understood that the technique also finds application with RNA. The PCR technique generally refers to the following procedure (see Erlich, Science, 252:1643 1650 (1991), the chapter by R. Higuchi, p. 61 70).

Additional modifications are also contemplated to further enhance the specificity of interaction between the two heavy chains. Accordingly, the present invention incorporates a covalent link between the two heavy chains (e.g. on the CH3 domains).

Examples of covalent links contemplated by the present invention include amide links and disulfide links.

Thus, for example the present invention contemplates introduction of a free thiol which forms an intermolecular disulfide bond between the two heavy chains of the antibody. The free thiol may be introduced into the interface of one of the heavy chains by substituting a naturally occurring residue of the heavy chain with, for example, a cysteine at a position allowing for the formation of a disulfide bond between the heavy chains.

The phrase "free thiol-containing compound" as used herein refers to a compound that can be incorporated into or reacted with an amino acid of a polypeptide interface of the invention such that the free thiol moiety of the compound is positioned to interact with a free thiol of moiety at the interface of additional polypeptide of the invention to form a disulfide bond. Preferably, the free thiol-containing compound is cysteine.

According to a specific embodiment, the first heavy chain comprises a S354C mutation (i.e. serine to cysteine); and the second heavy chain comprises a Y349C mutation (tyrosine to cysteine).

As well as having modifications in their heavy chains, at least one light chain of the antibodies described herein is also modified such that there is a first covalent link between a first heavy chain and a first light chain and a second covalent link between a second heavy chain and a second light chain, wherein a position of the first covalent link relative to the first heavy chain is different to a position of the second covalent link relative to the second heavy chain.

The positioning of the first and second covalent link is selected such that pairing between a heavy chain with its cognate light chain is facilitated, whilst the specificity and stability of the antibody is not reduced by more than 20% or preferably by more than 10% or even more preferably by more than 5% as compared to the individual antibodies from which it is generated.

According to another embodiment, the covalent link between the first heavy chain to its cognate light chain is positioned between the $C_{H1}$ and the $C_L$ region and the covalent link between the second heavy chain to its cognate light chain is positioned between the $V_H$ and the $V_L$ region.

Examples of covalent links contemplated by the present invention include for example amide links, disulfide links and additional forms of covalent bonds occurring between site-specifically inserted amino acid residues, including non-natural amino acids (see Wu, X., Schultz, P. G. "Synthesis at the Interface of Chemistry and Biology." J. Am. Chem. Soc., 131(35):12497-515, 2009; Hutchins B M, Kazane S A, Staflin K, Forsyth J S, Felding-Habermann B, Schultz P G, Smider V V. Site-specific coupling and sterically controlled formation of multimeric antibody fab fragments with unnatural amino acids J Mol Biol. 2011 Mar. 4; 406(4):595-603. Epub 2011 Jan. 13; Liu C C, Schultz P G. Adding new chemistries to the genetic code. Annu Rev Biochem. 2010; 79:413-44. Review, all of which are incorporated herein by reference).

Accordingly, the present invention contemplates mutating at least one of the heavy chains and its cognate light chain such that at least one naturally occurring (i.e. native) disulfide bond that connects the two molecules can no longer be generated. Typically, this is effected by deleting (or substituting) the cysteines at the positions described herein above.

As used herein, the phrase "native disulfide bond" refers to the interchain disulfide bond that connects a heavy chain to its cognate light chain (typically between the constant region of the light chain and the CH1 region of the heavy chain) encoded in a naturally occurring germline antibody gene.

Substitution of the cysteine is typically effected by replacing the amino acid with one similar in size and charge (i.e. a conservative amino acid, such as cysteine to alanine).

The present invention contemplates that the first covalent link is a naturally occurring disulfide bond and the second covalent link is a non-naturally occurring covalent bond, (e.g. an engineered disulfide bond), wherein at least one cysteine amino acid residue has been inserted into the chain—i.e. an engineered cysteine.

The term "engineered cysteine" as used herein, refers to a cysteine which has been introduced into the antibody fragment sequence at a position where a cysteine does not occur in the natural germline antibody sequence.

Alternatively, both the first and second covalent links may be non-naturally occurring and the cysteines (which in the non-modified antibody serve as amino acid residues to generate disulfide bonds) may be replaced by other amino acids that are not capable of serving as amino acid residues to generate covalent bonds.

Information regarding the antibody of interest is required in order to produce proper placement of the disulfide bond. The amino acid sequences of the variable regions that are of interest are compared by alignment with those analogous sequences in the well-known publication by Kabat and Wu [Sequences of Proteins of Immunological Interest," E. Kabat, et al., U.S. Government Printing Office, NIH Publication No. 91-3242 (1990], incorporated herein by reference, to determine which sequences can be mutated so that cysteine is encoded for in the proper position of each heavy and light chain variable region to provide a disulfide bond in the framework regions of the desired antibody.

After the sequences are aligned, the amino acid positions in the sequence of interest that align with the following positions in the numbering system used by Kabat and Wu are identified: positions 43, 44, 45, 46, and 47 (group 1) and positions 103, 104, 105, and 106 (group 2) of the heavy chain variable region; and positions 42, 43, 44, 45, and 46 (group 3) and positions 98, 99, 100, and 101 (group 4) of the light chain variable region. In some cases, some of these positions may be missing, representing a gap in the alignment.

Then, the nucleic acid sequences encoding the amino acids at two of these identified positions are changed such that these two amino acids are mutated to cysteine residues. Contemplated pairs of amino acids to be selected are: $V_H44$-$V_L100$, $V_H105$-$V_L43$, $V_H105$-$V_L42$, $V_H44$-$V_L101$, $V_H106$-$V_L43$, $V_H104$-$V_L43$, $V_H44$-$V_L99$, $V_H45$-$V_L98$, $V_H46$-$V_L98$, $V_H103$-$V_L43$, $V_H103$-$V_L44$, $V_H103$-$V_L45$.

Most preferably, substitutions of cysteine are made at the positions: $V_H44$-$V_L100$; or $V_H105$-$V_L43$. (The notation $V_H44$-$V_L100$, for example, refers to a polypeptide with a $V_H$ having a cysteine at position 44 and a cysteine in $V_L$ at position 100; the positions being in accordance with the numbering given by Kabat and Wu.)

Note that with the assignment of positions according to Kabat and Wu, the numbering of positions refers to defined conserved residues and not to actual sequentially numbered amino acid positions in a given antibody. For example, CysL100 (of Kabat and Wu) which is used to generate ds(Fv)B3 as described in the example below, actually corresponds to position 105 of B3($V_L$).

According to one embodiment, selection of which amino acid to mutate may be effected according to the rules set out in U.S. Pat. No. 5,747,654, incorporated herein by reference.

The sites of mutation to the cysteine residues can be identified by review of either the actual antibody or the model antibody of interest as exemplified below. Computer programs to create models of proteins such as antibodies are generally available and well-known to those skilled in the art (see Kabat and Wu; Loew, et al., Int. J. Quant. Chem., Quant. Biol. Symp., 15:55-66 (1988); Bruccoleri, et al., Nature, 335:564-568 (1988); Chothia, et al., Science, 233:755-758 (1986), all of which are incorporated herein by reference. Commercially available computer programs can be used to display these models on a computer monitor, to calculate the distance between atoms, and to estimate the likelihood of different amino acids interacting (see, Ferrin, et al., J. Mol. Graphics, 6:13-27 (1988), incorporated by reference herein). For example, computer models can predict charged amino acid residues that are accessible and relevant in binding and then conformationally restricted organic molecules can be synthesized. See, for example, Saragovi, et al., Science, 253:792 (1991), incorporated by referenced herein. In other cases, an experimentally determined actual structure of the antibody may be available.

According to one embodiment, a pair of suitable amino acid residues should (1) have a $C_\alpha$—$C_\alpha$ distance between the two residues less than or equal to 8 ANG, preferably less than or equal to 6.5 ANG (determined from the crystal structure of antibodies which are available such as those from the Brookhaven Protein Data Bank) and (2) be as far away from the CDR region as possible. Once they are identified, they can be substituted with cysteins.

Modifications of the genes to encode cysteine at the target point may be readily accomplished by well-known techniques, such as oligonucleotides-directed mutagenesis (as described herein above), site-directed mutagenesis (see, Gillman and Smith, Gene, 8:81-97 (1979) and Roberts, S., et al, Nature, 328:731-734 (1987), both of which are incorporated herein by reference), by the method described in Kunkel, Proc. Natl. Acad. Sci. USA 82:488-492 (1985), incorporated by reference herein, by total gene synthesis (Hughes, R. A. et al, Methods in Enzymology, Volume 498 p. 277-309 (2011)) or by any other means known in the art.

Antibodies of some embodiments of the present invention may be from any mammalian origin including human, porcine, murine, bovine, goat, equine, canine, feline, ovine and the like. The antibody may be a heterologous antibody.

As used herein a "heterologous antibody" is defined in relation to a transgenic host such as a plant expressing the antibody.

According to some embodiments of the invention, the antibody is an isolated intact antibody (i.e., substantially free of cellular material other antibodies having different antigenic specificities and/or other chemicals).

As used herein "recombinant antibody" refers to intact antibodies that are prepared, expressed, created or isolated by recombinant means, such as (a) antibodies isolated from an animal (e.g., mouse) that is transgenic for immunoglobulin genes (e.g., human immunoglobulin genes) or hybridoma prepared therefrom; (b) antibodies isolated from a host cell transformed to express the antibody; (c) antibodies isolated from a recombinant antibody library; and (d) antibodies prepared, expressed, created or isolated by any other means that involve splicing of immunoglobulin gene sequences to other DNA sequences. In certain embodiments immunoglobulin of the present invention may have variable and constant regions derived from human germline immunoglobulin sequences. In other embodiments, such recombinant human antibodies can be subjected to in vitro mutagenesis and thus the amino acid sequences of the $V_H$ and $V_L$ regions of the recombinant antibodies comprise sequences that while derived from and related to human germline $V_H$ and $V_L$ sequences, may not naturally exist within the human antibody germline repertoire in vivo.

The following exemplary embodiments of antibodies are encompassed by the scope of the invention.

A used herein "human antibody" refers to intact antibodies having variable regions in which both the framework and CDR regions are derived from human germline immunoglobulin sequences as described, for example, by Kabat et al. (see Kabat 1991, Sequences of proteins of immunological Interest, 5$^{th}$ Ed. NIH Publication No. 91-3242). The constant region of the human antibody is also described from human germline immunoglobulin sequences. The human antibodies may include amino residues not encoded by human germline immunoglobulin sequences (e.g., mutations introduced by random or site directed mutagenesis in vitro or somatic mutation in vivo). However, the term "human antibody", as used herein, is not intended to include antibodies in which CDR sequences derived from the germline of another mammalian species, such as a mouse, have been grafted onto human framework sequences.

As used herein, a "chimeric antibody" refers to an intact antibody in which the variable regions derive from a first species and the constant regions are derived from a second species. Chimeric immunoglobulins can be constructed by genetic engineering from immunoglobulin gene segments belonging to different species (e.g., VH and VL domains from a mouse antibody with constant domains of human origin).

As used herein "humanized immunoglobulin" refers to an intact antibody in which the minimum mouse part from a non-human (e.g., murine) antibody is transplanted onto a human antibody; generally humanized antibodies are 5-10% mouse and 90-95% human.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

The antibodies of the present invention may be conjugated to a functional moiety such as a detectable or a therapeutic moiety.

Various types of detectable or reporter moieties may be conjugated to the antibody of the invention. These include, but not are limited to, a radioactive isotope (such as [125] iodine), a phosphorescent chemical, a chemiluminescent chemical, a fluorescent chemical (fluorophore), an enzyme, a fluorescent polypeptide, an affinity tag, and molecules (contrast agents) detectable by Positron Emission Tomagraphy (PET) or Magnetic Resonance Imaging (MRI).

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, U K. (2001); U.S. Pat. No. 6,350,466 to Targesome, Inc.]. Fluorescence detection methods which can be used to detect the antibody when conjugated to a fluorescent detectable moiety include, for example, fluorescence activated flow cytometry (FACS), immunofluorescence confocal microscopy, fluorescence in-situ hybridization (FISH) and fluorescence resonance energy transfer (FRET).

Numerous types of enzymes may be attached to the antibody of the invention [e.g., horseradish peroxidase (HRP), beta-galactosidase, and alkaline phosphatase (AP)] and detection of enzyme-conjugated antibodies can be performed using ELISA (e.g., in solution), enzyme-linked immunohistochemical assay (e.g., in a fixed tissue), enzyme-linked chemiluminescence assay (e.g., in an electrophoretically separated protein mixture) or other methods known in the art [see e.g., Khatkhatay M I. and Desai M., 1999. J Immunoassay 20:151-83; Wisdom G B., 1994. Methods Mol Biol. 32:433-40; Ishikawa E. et al., 1983. J Immunoassay 4:209-327; Oellerich M., 1980. J Clin Chem Clin Biochem. 18:197-208; Schuurs A H. and van Weemen B K., 1980. J Immunoassay 1:229-49).

The affinity tag (or a member of a binding pair) can be an antigen identifiable by a corresponding antibody [e.g., digoxigenin (DIG) which is identified by an anti-DIG antibody) or a molecule having a high affinity towards the tag [e.g., streptavidin and biotin]. The antibody or the molecule which binds the affinity tag can be fluorescently labeled or conjugated to enzyme as described above.

Various methods, widely practiced in the art, may be employed to attach a streptavidin or biotin molecule to the antibody of the invention. For example, a biotin molecule may be attached to the antibody of the invention via the recognition sequence of a biotin protein ligase (e.g., BirA) as described in the Examples section which follows and in Denkberg, G. et al., 2000. Eur. J. Immunol. 30:3522-3532. Alternatively, a streptavidin molecule may be attached to an antibody fragment, such as a single chain Fv, essentially as described in Cloutier S M. et al., 2000. Molecular Immunology 37:1067-1077; Dubel S. et al., 1995. J Immunol Methods 178:201; Huston J S. et al., 1991. Methods in Enzymology 203:46; Kipriyanov S M. et al., 1995. Hum Antibodies Hybridomas 6:93; Kipriyanov S M. et al., 1996. Protein Engineering 9:203; Pearce L A. et al., 1997. Biochem Molec Biol Intl 42:1179-1188).

Functional moieties, such as fluorophores, conjugated to streptavidin are commercially available from essentially all major suppliers of immunofluorescence flow cytometry reagents (for example, Pharmingen or Becton-Dickinson).

According to some embodiments of the invention, biotin conjugated antibodies are bound to a streptavidin molecule to form a multivalent composition (e.g., a dimmer or tetramer form of the antibody).

Table 1 provides non-limiting examples of identifiable moieties which can be conjugated to the antibody of the invention.

TABLE 1

| Identifiable Moiety | Amino Acid sequence (GenBank Accession No.) | Nucleic Acid sequence (GenBank Accession No.) |
| --- | --- | --- |
| Green Fluorescent protein | AAL33912 | AF435427 |
| Alkaline phosphatase | AAK73766 | AY042185 |
| Peroxidase | CAA00083 | A00740 |
| Histidine tag | Amino acids 264-269 of GenBank Accession No. AAK09208 | Nucleotides 790-807 of GenBank Accession No. AF329457 |
| Myc tag | Amino acids 273-283 of GenBank Accession No. AAK09208 | Nucleotides 817-849 of GenBank Accession No. AF329457 |
| Biotin ligase tag | LHHILDAQKMVWNHR SEQ ID NO: 76 | |
| orange fluorescent protein | AAL33917 | AF435432 |
| Beta galactosidase | ACH42114 | EU626139 |
| Streptavidin | AAM49066 | AF283893 |

As mentioned, the antibody may be conjugated to a therapeutic moiety. The therapeutic moiety can be, for example, a cytotoxic moiety, a toxic moiety, a cytokine moiety and a second antibody moiety comprising a different specificity to the antibodies of the invention.

Non-limiting examples of therapeutic moieties which can be conjugated to the antibody of the invention are provided in Table 2, hereinbelow.

TABLE 2

| Therapeutic moiety | Amino acid sequence (GenBank Accession No.) | Nucleic acid sequence (GenBank Accession No.) |
|---|---|---|
| Pseudomonas exotoxin | ABU63124 - SEQ ID NO: 42 | EU090068 - SEQ ID NO: 51 |
| Diphtheria toxin | AAV70486 - SEQ ID NO: 43 | AY820132.1 - SEQ ID NO: 52 |
| interleukin 2 | CAA00227 - SEQ ID NO: 44 | A02159 - SEQ ID NO: 53 |
| CD3 | P07766 - SEQ ID NO: 45 | X03884 - SEQ ID NO: 54 |
| CD16 | NP_000560.5 - SEQ ID NO: 46 | NM_000569.6 - SEQ ID NO: 55 |
| interleukin 4 | NP_000580.1 - SEQ ID NO: 47 | NM_000589.2 - SEQ ID NO: 56 |
| HLA-A2 | P01892 - SEQ ID NO: 48 | K02883 - SEQ ID NO: 57 |
| interleukin 10 | P22301 - SEQ ID NO: 49 | M57627 - SEQ ID NO: 58 |
| Ricin toxin | EEF27734 - SEQ ID NO: 50 | EQ975183 - SEQ ID NO: 59 |

The functional moiety may be conjugated to the $V_H$ or the $V_L$ sequence at either the N- or C-terminus or be inserted into other protein sequences in a suitable position. For example, for *Pseudomonas exotoxin* (PE) derived fusion proteins, either $V_H$ or $V_L$ should be linked to the N-terminus of the toxin or be inserted into domain III of PE. For Diphtheria toxin-derived antibodies, $V_H$ or $V_L$ is preferably linked to the C-terminus of the toxin.

It will be appreciated that such fusions can also be effected using chemical conjugation (i.e., not by recombinant DNA technology).

The $V_H$ and $V_L$ sequences for application in this invention can be obtained from antibodies produced by any one of a variety of techniques known in the art.

Methods of producing polyclonal and monoclonal antibodies are well known in the art (See for example, Harlow and Lane, Antibodies: A Laboratory Manual, Cold Spring Harbor Laboratory, New York, 1988, incorporated herein by reference).

Typically, antibodies are provided by immunization of a non-human animal, preferably a mouse, with an immunogen comprising a desired antigen or immunogen. Alternatively, antibodies may be provided by selection of combinatorial libraries of immunoglobulins, as disclosed for instance in Ward et al (Nature 341 (1989) 544). Thus any method of antibody production is envisaged according to the present teachings as long as an immunoglobulin antibody is finally expressed in the bacterial host.

The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988)). In a preferred embodiment, the non-human animal is a mammal, such as a rodent (e.g., mouse, rat, etc.), bovine, porcine, horse, rabbit, goat, sheep, etc. As mentioned, the non-human mammal may be genetically modified or engineered to produce "human" antibodies, such as the Xenomouse™ (Abgenix) or HuMAb-Mouse™ (Medarex). Typically, the immunogen is suspended or dissolved in a buffer, optionally with an adjuvant, such as complete Freund's adjuvant. Methods for determining the amount of immunogen, types of buffers and amounts of adjuvant are well known to those of skill in the art and are not limiting in any way on the present invention. These parameters may be different for different immunogens, but are easily elucidated.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with adjuvant such as incomplete Freund's adjuvant. The recall injections are performed intravenously or intraperitoneally and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be utilized as long as they result in the production of B cells expressing an antibody directed to the antigen used in immunization.

In an alternate embodiment, lymphocytes from a non-immunized non-human mammal are isolated, grown in vitro, and then exposed to the immunogen in cell culture. The lymphocytes are then harvested and the fusion step described below is carried out.

For monoclonal antibodies, the next step is the isolation of splenocytes from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule and through a nylon mesh of a cell strainer into an appropriate buffer so as to produce a single cell suspension. The cells are washed, centrifuged and re-suspended in a buffer that lyses any red blood cells. The solution is again centrifuged and remaining lymphocytes in the pellet are finally re-suspended in fresh buffer.

Once isolated and present in single cell suspension, the lymphocytes are fused to an immortal cell line. This is typically a mouse myeloma cell line, although many other immortal cell lines useful for creating hybridomas are known in the art. Preferred murine myeloma lines include, but are not limited to, those derived from MOPC-21 and MPC-11 mouse tumors available from the Salk Institute Cell Distribution Center, San Diego, Calif. U.S.A., X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

The hybridomas are typically grown on a feeder layer of macrophages. The macrophages are preferably from littermates of the non-human mammal used to isolate splenocytes and are typically primed with incomplete Freund's adjuvant or the like several days before plating the hybridomas. Fusion methods are described in (Goding, "Monoclonal Antibodies: Principles and Practice," pp. 59-103 (Academic Press, 1986.

The cells are allowed to grow in the selection media for sufficient time for colony formation and antibody production. This is usually between 7 and 14 days. The hybridoma colonies are then assayed for the production of antibodies that bind the immunogen/antigen. The assay is typically a colorimetric ELISA-type assay, although any assay may be employed that can be adapted to the wells that the hybridomas are grown in. Other assays include immunoprecipitation and radioimmunoassay. The wells positive for the desired antibody production are examined to determine if one or more distinct colonies are present. If more than one colony is present, the cells may be re-cloned and grown to ensure that only a single cell has given rise to the colony producing the desired antibody. Positive wells with a single apparent colony are typically recloned and re-assayed to insure only one monoclonal antibody is being detected and produced.

Hybridomas that are confirmed to be producing a monoclonal antibody are then grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Amersham Biosciences, publication No. 18-1037-46, Edition A C, the disclosure of which is hereby incorporated by reference). The bound antibody is typically eluted from protein A, protein G or protein L columns by using low pH buffers (glycine or acetate buffers of pH 3.0 or less) with immediate neutralization of antibody-containing fractions. These fractions are pooled, dialyzed, and concentrated as needed.

DNA encoding the heavy and light chains of the antibody may be readily isolated and sequenced using conventional procedures (e.g., by using oligonucleotide probes that are capable of binding specifically to genes encoding the heavy and light chains of antibodies such as murine or human). Once isolated, the DNA can be ligated into expression vectors, which are then transfected into host cells.

The antibodies according to the invention are typically produced by recombinant means.

The DNA sequences encoding the immunoglobulin light chain and heavy chain polypeptides may be independently inserted into separate recombinant vectors or one single vector, which may be any vector, which may conveniently be subjected to recombinant DNA procedures, and the choice of vector will often depend on the host cell into which it is to be introduced.

Methods for recombinant production are widely known in the state of the art and comprise protein expression in prokaryotic and eukaryotic cells with subsequent isolation of the antibody and usually purification to a pharmaceutically acceptable purity.

For the expression of the antibodies as aforementioned in a host cell, nucleic acids encoding the respective modified light and heavy chains are inserted into expression vectors by standard methods.

The procedures used to ligate the DNA sequences coding for the polypeptides, the promoter (e.g., constitutive or inducible) and optionally the terminator sequence, respectively, and to insert them into suitable vectors containing the information necessary for replication, are well known to persons skilled in the art (see, for instance, Sambrook et al., Molecular Cloning: A Laboratory Manual, Cold Spring Harbor, N.Y., 1989).

Expression is performed in appropriate prokaryotic or eukaryotic host cells like CHO cells, NSO cells, SP2/0 cells, HEK293 cells, COS cells, PER.C6 cells, yeast, or bacterial cells, and the antibody is recovered from the cells (supernatant or cells after lysis).

The present invention contemplates expressing each component of the antibody in its own individual host cell, or various combinations of the antibody components in their own host cells. Thus for example, the light chains may be expressed in one host cell and the heavy chains in another host cell. Alternatively, one light chain and one heavy chain is expressed in one host cell and the second light chain and the second heavy chain is expressed in another host cell. Still alternatively, both the heavy chains and both the light chains may be expressed in the same host cell.

It will be appreciated that when both the heavy chains and both the light chains are expressed in the same host cell, in vitro assembly of the chains is not necessary and only purification of the antibodies form the conditioned medium i.e. by protein A chromatography is required (See for example: Jackman J, J Biol Chem. 2010 Jul. 2; 285(27): 20850-9. Epub 2010 May 5).

When at least one of the chains is expressed in a different host cell to the other three chains, in vitro assembly of the chains is required.

According to a specific embodiment, the host cell comprises bacterial cells.

According to another embodiment the antibodies are generated as inclonals as described in WO2009/107129 incorporated herein by reference.

The bacterial host may be selected capable of producing the recombinant proteins (i.e., heavy and light chains) as inclusion bodies (i.e., nuclear or cytoplasmic aggregates of stainable substances).

The host cells (e.g., first host cell and second host cell) used can be of identical species or different species.

According to specific embodiments of the present invention the host cells are selected from a Gram-negative bacterium/bacteria.

As used herein "Gram negative bacteria" refers to bacteria having characteristic staining properties under the microscope, where they either do not stain or are decolorized by alcohol during Gram's method of staining. Gram negative bacteria generally have the following characteristics: (i) their cell wall comprises only a few layers of peptidoglycans (which is present in much higher levels in Gram positive bacteria); (ii) the cells are surrounded by an outer membrane containing lipopolysaccharide (which consists of Lipid A, core polysaccharide, and 0-polysaccharide) outside the peptideglycan layer; (iii) porins exist in the outer membrane, which act like pores for particular molecules; (iv) there is a space between the layers of peptidoglycan and the secondary cell membrane called the periplasmic space; (v) the S-layer is directly attached to the outer membrane, rather than the peptidoglycan (vi) lipoproteins are attached to the polysaccharide backbone, whereas in Gram positive bacteria no lipoproteins are present.

Examples of Gram-negative bacteria which can be used in accordance with the present teachings include, but are not limited to, Escherichia coli Pseudomonas, erwinia and Serratia. It should be noted that the use of such Gram-negative bacteria other than E. coli such as Pseudomonas as a host cell would provide great economic value owing to both the metabolic and physiologic properties of pseudomonas. Under certain conditions, pseudomonas, for example, can be grown to higher cell culture densities than E. coli thus providing potentially greater product yields.

Examples of bacterial expression vectors suitable for use in accordance with the present teachings include, but are not limited to, pET™ systems, the T7 systems and the pBAD™ system, which are well known in the art.

Methods of introducing expression vectors into bacterial host cells are well known in the art and mainly depend on the host system used.

The host cells can either be co-cultured in the same medium, or cultured separately.

Host cells are cultured under effective conditions, which allow for the expression of high amounts of recombinant heavy and light chain. Effective culture conditions include, but are not limited to, effective media, bioreactor, temperature, pH and oxygen conditions that permit recombinant protein production. An effective medium refers to any medium in which a bacterium is cultured to produce the recombinant protein of the present invention. Such a medium typically includes an aqueous solution having assimilable carbon, nitrogen and phosphate sources, and appropriate salts, minerals, metals and other nutrients, such as vitamins. Bacterial hosts of the present invention can be cultured in conventional fermentation bioreactors, shake flasks, test tubes, microtiter dishes, and petri plates, dependent on the desired amount. Culturing can be carried out at a temperature, pH and oxygen content appropriate for a recombinant host. Such culturing conditions are within the expertise of one of ordinary skill in the art.

Once appropriate expression levels of immunoglobulin heavy and light chains are obtained, the polypeptides are recovered from the inclusion bodies. Methods of recovering recombinant proteins from bacterial inclusion bodies are well known in the art and typically involve cell lysis followed by solubilization in denaturant [e.g., De Bernardez-Clark and Georgiou, "Inclusion bodies and recovery of proteins from the aggregated state" Protein Refolding Chapter 1:1-20 (1991). See also Examples section which follows, under "*Expression of Inclonals in E. coli*"].

Briefly, the inclusion bodies can be separated from the bulk of cytoplasmic proteins by simple centrifugation giving an effective purification strategy. They can then be solubilized by strong denaturing agents like urea (e.g., 8 M) or guanidinium hydrochloride and sometimes with extremes of pH or temperature. The denaturant concentration, time and temperature of exposure should be standardized for each protein. Before complete solubilization, inclusion bodies can be washed with diluted solutions of denaturant and detergent to remove some of the contaminating proteins.

Finally, the solubilized inclusion bodies can be directly subjected to further purification through chromatographic techniques under denaturing conditions or the heavy and light chains may be refolded to native conformation before purification.

Thus, further purification of the reconstituted/refolded heavy and light chain polypeptides (i.e., solubilized reduced polypeptides) can be effected prior to, and alternatively or additionally, following refolding.

Methods of antibody purification are well known in the art and are described hereinabove and in the Examples section which follows. Other methods for purification of IgG are described in "Purification of IgG and insulin on supports grafted by sialic acid developing "thiophilic-like" interactions Hamid Lakhiaria and Daniel Mullerb, Journal of Chromatography B Volume 818, Issue 1, 15 Apr. 2005, Pages 53-59.

Alternatively or additionally, purification can be affinity-based through the identifiable or therapeutic moiety (e.g., using affinity columns which bind PE38 to purify antibodies that are fused to PE38).

Further purification of antibodies may be performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

To improve the refolding yield, the reconstituted heavy chains and reconstituted light chains are provided at a ratio selected to maximize the formation of an intact antibody. To this end, a heavy to light chain molar ratio of about 1:1 to 1:3, 1:1.5 to 1:3, 1:2 to 1:3 is. In an exemplary embodiment the heavy to light chain molar ratio is about 1:1.

When desired the immunoglobulin may be subjected to directed in vitro glycosylation, which can be done according to the method described by Isabelle Meynial-salles and Didier Combes. In vitro glycosylation of proteins: An enzymatic approach. Journal of Biotechnology Volume 46, Issue 1, 18 Apr. 1996, Pages 1-14.

One aspect of the invention is a pharmaceutical composition comprising an antibody according to the invention. Another aspect of the invention is the use of an antibody according to the invention for the manufacture of a pharmaceutical composition. A further aspect of the invention is a method for the manufacture of a pharmaceutical composition comprising an antibody according to the invention. In another aspect, the present invention provides a composition, e.g. a pharmaceutical composition, containing an antibody according to the present invention, formulated together with a pharmaceutical carrier.

Antibodies and compositions (e.g., pharmaceutical composition) comprising same may be used in diagnostic and therapeutic applications and as such may be included in therapeutic or diagnostic kits.

Thus, compositions of the present invention may, if desired, be presented in a pack or dispenser device, such as an FDA approved kit, which may contain one or more unit dosage forms containing the active ingredient i.e., antibody. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

One use of the antibody according to the invention is for the treatment of diseases related to inflammation and infections.

As used herein the term "inflammation" refers to any medical condition which comprises an inflammatory response in which migration of cells (e.g. to the lymph nodes) contributes to inflammation onset or progression.

A number of diseases and conditions, which involve an inflammatory response, can be treated using the methodology described hereinabove including both chronic inflammatory diseases and acute inflammatory diseases.

Examples of such diseases include inflammatory diseases associated with hypersensitivity.

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Other types of inflammatory diseases which may be treated with the bifunctional antibodies disclosed herein are autoimmune diseases, infectious diseases, graft rejection diseases, allergic diseases and cancerous diseases.

The term "cancer" as used herein refers to proliferative diseases including by not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphocytic leukemia, such as Acute lymphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

Treatment of diseases may be effected by administering the antibody alone, or together with a carrier as a pharmaceutical composition.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent.

Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions.

In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

Other contemplated uses of the bispecific antibodies of the present invention include purification of analytes; in immunohistochemistry and enzyme immunoassays; for radioimaging and radioimmunotherapy and for drug delivery.

Other contemplated uses are set forth in Cao Y, Suresh M R. Bispecific antibodies as novel bioconjugates. Bioconjug Chem. 1998 November-December; 9(6):635-44, incorporated herein by reference.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods for Examples 1-4

Construction of Expression Vectors for Heavy and Light Chains:

The vector for production of antibody heavy and light chains in *E. coli* were constructed on the backbone of pHAK vectors (Hakim and Benhar, 2009). The heavy chains vectors were modified at the CH2-CH3 constant regions using Kunkel mutagenesis (Kunkel, 1985) to contain heavy-heavy heterodimer-preferable mutations according to "knobs-into-holes" approach (Merchant et al., 1998). To that end, DNA of the pHAK-IgH vector was prepared in *E. coli* CJ236 strain, infected with M13KO7 helper phage and released single-stranded uracil-containing plasmid DNA was collected the next day using phenol-chloroform purification. The DNA samples were incubated with either primer 1 (for introduction of "knob" mutations) or the mixture of primer 2, primer 3 and primer 4 (for introduction of "hole" mutations) (Table 3, herein below) in TM buffer (0.01 M $MgCl_2$, 0.05 M Tris pH 7.5). In the next step, the DNA samples were incubated in presence of T7 polymerase and T4 ligase enzymes (supplied by 0.4 mM ATP, 0.4 mM dNTPs, 6 mM DTT) and transformed into DH5α *E. coli* bacteria. The resulted constructs were named pHAK-HC-knob (carrying mutations T366W, S354C) and pHAK-HC-hole (carrying mutations T366S, L368A, Y407V, Y349C). The mutation-containing regions were subcloned using NsiI-NdeI restriction enzymes into pHAK-IgH-PE38 vector (Hakim and Benhar, 2009) that resulted in pHAK-HC-knob-PE38 and pHAK-HC-hole-PE38 vectors. The above constructs provided expression of antibody heavy chain fused to PE38 toxin.

TABLE 3

| Primer name | Sequence 5' to 3' | Notes |
|---|---|---|
| Primer1 S→C: T→W | GAAGCCTTTGACCAGGCAccaCAG GCTGACCTGGTTCTTGGTCATCTC CTCCCGGcATGGGGGCAGGGTGT ACAC - SEQ ID NO: 1 | Reverse primer for Kunkel mutagenesis that provides S354C and T366W replacements on pHAK-IgH vector. |
| Primer2 Y→C | GGATGGGGGCAGGGTGcACACCT GTGGTTCTCGG - SEQ ID NO: 2 | Reverse primer for Kunkel mutagenesis that provides Y349C replacement on pHAK-IgH vector. |
| Primer3 T→S: L→A | GGATAGAAGCCTTTGACCgcGC AGcTCAGGCTGACCTGGTTCTTG - SEQ ID NO: 3 | Reverse primer for Kunkel mutagenesis that provides L368A and T366S replacements on pHAK-IgH vector. |
| Primer4 Y→V | GTCCACGGTGAGCTTGCTAacG AGGAAGAAGGAGCCGTC - SEQ ID NO: 4 | Reverse primer for Kunkel mutagenesis that provides Y407 replacement on pHAK-IgH vector. |
| Primer5 | ATATACATATGGACATTGTGCTG NdeI - SEQ ID NO: 5 | Forward primer for PCR amplification of variable region of light chain on pHAK-T427-IgL vector |
| Primer6 | tatatacgtacgTTTGATTTCCAGTTTGG BstWI TGCCgcaACCGAACGTCCGAGG - SEQ ID NO: 6 | Reverse primer for A104C replacement in variable domain of T427-IgL. |
| Primer7 | tatataGAATTCTTACTCTCCCCTGTT EcoRI GAAGCTCTTTGTG - SEQ ID NO: 7 | Reverse primer for removal of C218 amino acid codon from light chain sequence. |
| Primer8 | AAACAGAGGCCTGGACAGtGTC StuI TGGAATGGATTG - SEQ ID NO: 8 | Forward primer for G44C replacement in variable domain of T427-IgH. |
| Primer9 | tatataGCTAGCGGAGGAGACTGTG NheI AG - SEQ ID NO: 9 | Reverse primer for PCR amplification of variable region of heavy chain on pHAK-T427-IgH vector. |
| Primer10 | GCCCAAATCTgccGACAAAACTCA CACATGCCCACC - SEQ ID NO: 10 | Forward primer for C222A replacement in heavy chain constant region on pHAK-IgH vector. |
| Primer11 | TGTGTGAGTTTTGTCggcAGATTTG GGCTCAACTCTCTTG - SEQ ID NO: 11 | Reverse primer for C222A replacement in heavy chain constant region on pHAK-IgH vector. |
| Primer12 | GAGGAGATGACCAAGAACCAGGT - SEQ ID NO: 12 | Reverse primer for amplification of heavy chain constant region of pHAK-IgH vector. |
| Primer13 | atataCATATGCAGGTCAAACTGC NdeI - SEQ ID NO: 13 | Forward primer for amplification of heavy chain variable region of pHAK-T427-IgH vector. |

To provide for efficient pairing of the heavy-light chains, the native interchain di-sulfide bond was replaced with an engineered bond at an alternative position in one IgH/IgL pair. The mutations that were inserted in pHAK-LC-Cys were A104C in $V_L$, and a C218del in C-Kappa. The mutations that were inserted in pHAK-HC-Cys were A44C in $V_H$ and C222A in CH1. The construction of pHAK-LC-Cys vector included two sequential cloning steps. First, the light chain variable domain of the selected antibody was amplified with primer 5 and primer 6, digested with NdeI-BsiWI restriction enzymes and cloned to pHAK-IgL previously digested with the same enzymes. The resulted vector served as a template for amplification of IgL with primer 5 and primer 7, which was digested with NdeI-EcoRI enzymes and cloned to pHAK-IgL (NdeI-EcoRI digested). In order to construct pHAK-HC-Cys (A44C), the heavy chain variable region of selected antibody was amplified with primer 8 and primer 9, following StuI-NheI digestion and cloning into pHAK-IgH vector. The insertion of the C222A mutations into CH1 was carried out by amplification of two of the two PCR fragments that were generated by either 10 and 12 primers or 11 and 13 primers, followed by assembly PCR with primer 12 and primer 13. The assembled DNA fragment was digested with NdeI and BsrGI restriction enzymes and cloned into previously constructed pHAK-HC-Cys (A44C) vector.

The combined pHAK-HC-Cys-knob vector (A44C, C222A, T366W, and S354C) was constructed by insertion of NdeI-SacII digested region of pHAK-HC-Cys to pHAK-HC-knob vector. The light or heavy variable regions of desired antibody were cloned on either pHAK-LC-based vector (using NdeI-BsiWI subcloning) or pHAK-HC-based vector (using NdeI-NheI subcloning).

IgG Production in E. coli:

Heavy and light chains constructs based on pHAK-IgH and pHAK-IgL, respectively, were expressed in separate E. coli BL21 (DE3) pUBS500 bacterial cultures as inclusion bodies. The inclusion bodies were purified, denatured, mixed and refolded according to the Inclonals IgG production method (Hakim and Benhar, 2009). For bispecific IgG production the complement heavy chains were added at 1:1 molar ratio. The same rule was applied for the light chains.

Protein A Purification:

Following the refolding process IgG and IgG-based fusion proteins were loaded on a protein A affinity column and separated from bacterial contaminants and not efficiently refolded proteins. The proteins were eluted with 0.1 mM citric acid neutralized with 1M Tris (HCl) pH 8.5 followed by dialysis against 20 mM phosphate buffer solution (PBS) pH 7.4. The protein final concentration was determined by absorbance at 280 nm.

Gel Filtration Chromatography:

Gel filtration analysis was carried out on Amersham Pharmacia ÄKTA FPLC System to determine the molecular mass of the purified antibodies. The protein A purified proteins were applied to a Superdex 200 column, previously equilibrated with PBS (pH 7.4), and separated using the same buffer at a flow rate of 0.5 ml/min. The molecular weight of examined IgG-like proteins was determined by comparing its elution volume with that of standard IgG (150 kDa) and IgG-based immunotoxin IgG-PE38 (225 kDa).

SDS-PAGE Analysis:

Polyacrylamide gel electrophoresis of proteins was performed according to Laemmli (Laemmli, 1970) ⅕ volume of 5× sample buffer was added to the protein samples followed by boiling for 5 min prior to the loading onto the gel. 7.5%, 10% and 12% mini-gels were run at 120 V. For evaluation of full length IgG, the non-reduced samples (without β-mercaptoethanol) were loaded, while the reduced protein samples separated into heavy and light chains components. Gels were stained with Coomassie blue solution (0.05% Coomassie R-250, 20% ethanol, 10% glacial acetic acid) for 2 hours and washed in destain solution (20% ethanol, 10% glacial acetic acid) until protein bands could be clearly seen. The protein band density was analyzed by ImageMaster 1D scanning laser densitometer (Pharmacia, Sweden). Gels that were stained were loaded with 20 μg of protein per lane for non-purified fraction or 3-5 μg for purified proteins. Gels that were further processed by immunoblotting were loaded with 1/10 that quantity.

Western Blot Analysis:

Proteins resolved by SDS-PAGE were electro-transferred onto the nitrocellulose membrane according to (Towbin et al., 1992). The membrane was blocked for at least 1 hour with PBS containing 5% non-fat milk powder at room temperature with slow agitation. The membrane was washed with PBS followed by incubation HRP conjugated goat-anti-human secondary antibodies (Jackson Immunoresearch Laboratories, West Grove, Pa.). After three washes with PBS containing 0.05% Tween-20 (PBST) and one wash with PBS the nitrocellulose filter was developed with the SuperSignal West Pico Chemiluminescent Substrate (Thermo Scientific, USA) as described by the vendor.

ELISA Analysis:

The antigen binding by mono- and bispecific IgGs was determined as follows: the 96-well ELISA plate was coated with 5 μg/ml of pure antigen in PBS 100 μl/well for overnight at 4° C. and blocked with 3% skim milk (in PBS) for 1 hour at 37° C. All subsequent steps were carried out at room temperature (25° C.). Protein A purified proteins were applied onto the plates in a three-fold dilution series in PBST for 1 hour incubation and washed with PBST for three times. Following the 1 hour incubation with HRP conjugated secondary antibodies (1:5000 dilution in PBST, 100 μl/well), the plates were washed in PBST and developed using chromogenic HRP substrate TMB and colour development was terminated with 1M $H_2SO_4$. The plated were read at 450 nm.

Example 1

Production of Full-Length IgG in E. coli Using Inclonals Method

The Inclonals method for production of full-length IgG in E. coli bacteria (Hakim and Benhar, 2009) includes using pHAK-IgH and pHAK-IgL vectors for production of IgH and IgL, respectively in separate bacterial cultures. The variable regions of heavy and light chains define the antibody specificity while the constant region is common for each vector. The protein expression, purification and refolding was carried out according to the Inclonals protocol and the purified proteins were evaluated using SDS-PAGE, Western blot, size exclusion chromatography and antigen binding analysis. As opposed to mono-specific antibody, the bispecific IgGs consists of 2 different heavy chains and 2 different light chains, thus expression and refolding steps include concomitant work with 4 proteins.

Example 2

Construction and Evaluation of Heavy-Heavy Chain Heterodimers

The "knobs-into-holes" approach (Ridgway et al., 1996) was implemented as a solution to preferable heterodimerization of different heavy chains for bispecific IgG production in E. coli. It was previously demonstrated that introduction of 4 mutations (T366W in "knob" heavy chain and T366S, L368A, Y407V in "hole" heavy chain) and the asymmetric disulfide bond (S354C and Y349C on complement heavy chains) provided high (>95%) heterodimerization level of heavy chains in IgG produced in mammalian cells (Merchant et al., 1998), (FIG. 1A). The above mutations were used for construction of pHAK-HC-knob and pHAK-HC-hole vectors that were used for expression and examination of heavy chains, while the common unmodified light chain served for all IgG constructs (FIG. 2A-H). T427 (anti-CD30) and FRP5 (anti-erbB2) antibodies were used as model IgGs for method evaluation (Harwerth et al., 1992; Nagata et al., 2004). The antibody heavy and light chains were expressed as inclusion bodies, purified by centrifugation and analyzed by SDS-PAGE (FIG. 3). The refolding of 4 antibody chains together followed by protein A purification according to Inclonals protocol enabled production of full-length IgG.

For detailed characterization of heterodimerization yield the "hole-heavy" chain was expressed as fusion protein with PE38 toxin (Kreitman et al., 1992) that provided additional 38 kDa to protein molecular weight. As illustrated in FIGS. 4A-B, using SDS-PAGE analysis it was possible to distinguish between the homodimer of "knob" heavy chains (150 kDa), the homodimer of "hole" toxin-fused heavy chains (230 kDa) and the heterodimer of two different heavy chains (190 kDa). FIG. 4B demonstrates that Inclonals' produced T427 "knobs-into-holes" antibody migrated as 190 kDa band on a non-reducing polyacrylamide gel and could be separated to 3 components (IgL, IgH and IgH-PE38) under reducing conditions.

The attempt to produce "knob-knob" and "hole-hole" versions of IgG by supplying the refolding solution with only one heavy chain type (either "knob" or "hole") resulted in assembly failure of IgG and performance of partial-sized molecules (FIGS. 5A-B).

The evaluation of bispecific inclonals "knobs-into-holes" antibodies using size-exclusion chromatography demonstrated that protein majority migrated as a 190 kDa molecules while only small protein fraction represented homodimers (FIG. 6). Density analysis SDS-PAGE of the Inclonals "knobs-into-holes" antibody concluded that >90% of *E. coli* produced IgGs underwent heavy chains heterodimerization (FIGS. 7A-C).

In order to evaluate the binding activity of bispecific molecules the "knobs-into-holes" bispecific T427-FRP5 antibody was constructed. This IgG consisted of 4 different chains: FRP5-knob and T427-hole-PE38 heavy chains, and FRP5 wt and T427 wt light chains. The PE38 toxin in this construct was used as a detection signal for T427 heavy chain presence. The mono-specific T427 and FRP5 IgGs served as controls. Using indirect ELISA the present inventors demonstrated the antibodies' binding ability to each one of its antigens (erbB2 for FRP5 (FIG. 8A) and CD30 for T427 (not shown)). The special ELISA (FIG. 8B) analysis examines the antibody binding to FRP5 antigen while T427-PE38 chain was detected. This assay demonstrated the presence of T427-FRP5 heterodimer that was able to bind its' two antigens.

Example 3

Construction and Evaluation of Heavy-Light Chains Specific Pairing

In order to introduce the disulfide bond between the two variable domains to replace the native heavy-light interchain S—S bond, the T427 antibody was used. This antibody has been extensively studied and its' cysteine positions for dsFv have been well defined (Nagata et al., 2004). Vectors pHAK-HC-Cys and pHAK-LC-Cys were constructed by replacement of conventional cysteine position by dsFv defined. The production of dsFv-like modified mono-specific IgG demonstrated the efficient formation of full length IgG stabilized by a single dsFv-like heavy-light interchain S—S bond (FIG. 9, lane 3).

The construction of pHAK-HC-Cys-knob enabled the production of fully bispecific full length T427-FRP5 IgG (FIG. 9, lane 4). Heterodimerization of heavy chains was provided by "knobs-into-holes" strategy and heavy-light pair matching was ensured by asymmetric interchain disulfide bond. Further, the IgG refolding solutions provided with unpaired heavy and light chains did not generate complete IgG molecules (FIG. 10).

Example 4

Two additional bispecific antibodies were produced, purified and evaluated, as described above in the materials and methods.
 1. T427-αSA IgG: binding to CD30 and streptavidin (SA). The bispecific antibody consisted of 4 chains: IgL-T427-Cys (Cys104:Cys218del), IgH-T427-knob-Cys (Cys44:Cys222Ala+S354C:T366W), IgL-αSA and IgH-αSA-hole (Y349C:T366S:L368A:Y407V).
 2. T427-αPE (B11 clone) IgG: binding to CD30 and PE38 (*Pseudomonas* exotoxin 38 kDa fragment). The bispecific antibody consisted of 4 chains: IgL-T427-Cys (Cys104:Cys218del), IgH-T427-knob-Cys (Cys44: Cys222Ala+S354C:T366W), IgL-αPE and IgH-αPE-hole (Y349C:T366S:L368A:Y407V).

The anti-streptavidin (αSA) and anti-PE B11 clone (αPE) antibodies were isolated as scFvs by affinity selecting the "Ronit1" antibody phage display library (Azriel-Rosenfeld et al., 2004, J Mol Biol 335, 177-92). The heavy and light domains were cloned into the pHAK-IgH-hole and pHAK-IgL, respectively (as mentioned above). The chains were produced in *E. coli* bacteria as inclusion bodies, purified by centrifugation and analyzed by SDS-PAGE electrophoresis (FIG. 11). The appropriate heavy and light chains were mixed, refolded and purified by Protein A affinity purification for production of mono-specific T427, αSA, αPE and bispecific T427-αSA and T427-αPE antibodies according to Inclonals protocol (Hakim and Benhar, 2009). The antibodies were analyzed by ELISA for binding activity to each antigen (FIGS. 12 and 13). As shown, these bispecific antibodies were successfully produced and bound the two antigens according to the specificities of the two arms. Specificity was demonstrated by negligible binding to bovine serum albumin (BSA).

Materials and Methods for Examples 5-9

Construction of pDual Vectors for Expression of IgGs in Mammalian Cells

The vector for production of antibody heavy and light chains in *E. coli* were constructed on the backbone of pMAZ vectors (Mazor Y., et al. J Immunol Methods. 2007 Apr. 10; 321(1-2):41-59.). Two bi-cistronic pMAZ vectors were constructed—pMAZ-IgH that carried the heavy chain and a Neomycin selection marker; and pMAZ-IgL that carried the light chain and a hygromycin selection marker. IgG expression was mediated by co-transfection of the two vectors, followed by double drug selection for obtaining stable transfectants.

The pDual vector was based on pMAZ-IgH vector that was previously mutated using IgH-Apadel-NheI-For and IgH-BsrGI-Rev primers in order to delete the ApaI restriction site in the constant region. The next step was the construction of pCMV-IgL-term cassette and cloning it between the KpnI-EcoRI restriction sites of pMAZ-IgH-Apadel vector. The pCMV-IgL-term cassette was built by assembly of three PCR products that included: 1) amplification of pCMV promoter using pCMV-KpnI-For and pCMV-Rev primers that provided the replacement of BssHI by ApaI restriction site (this ApaI site will be unique in the plasmid since the ApaI site that was present in the Fc coding region was mutated); 2) amplification of the T427 light chain antibody (VL+LC) using T427L-For and T427L-Rev primers that provided the replacement of XbaI by NotI restriction site; 3) amplification of the BGH polyadenylation site using BGH-polyA-For and BGH-polyA-EcoRI-Rev primers. The above PCR products were assembled into pCMV-IgL-term cassette by overlap-extension polymerase chain reaction (assembly PCR) followed by digestion with KpnI and EcoRI restriction enzymes and cloning into pMAZ-IgH-Apadel vector as described above. The resulted vector was named pDual that was further used for cloning of variable domains of different antibodies using ApaI-BsiWI restriction sites for VL (kappa light chains, for lambda light chains, a separate vector is required that carries a lambda light chain, into which V-lambda variable domain should be cloned as ApaI-AvrII restriction fragments) and BssHI-NheI restriction sites for VH.

A similar pDual vector was constructed that carries the hygromycin selection marker.

The list of primers used for generating the above described pDual vectors is summarized in Table 4, herein below.

cells were harvested 24 hours post transfection and seeded on DMEM supplemented with appropriate antibiotics (1.2 mg/ml G418 and 0.2 mg/ml Hygromycin). The stable clones were collected and their media were evaluated for the presence of antibody.

IgG Production in HEK293 T-REx™ Cells:

The previously obtained stable clones were transferred to tissue culture flasks (250 cm$^3$) in DMEM supplement with 0.9 mg/ml G418 and 0.15 mg/ml Hygromycin (75% of the regular concentration). The next day (or when the cells reached 80% confluence) the medium was changed to 50% DMEM (+L-Glu, PNS and bovine serum) and 50% DCCM1 (+L-Glu, PNS, serum free)+75% of antibiotics concentration (0.9 mg/ml G418 and 0.15 mg/ml of Hygromycin) for 24 hours. The next day the medium was changed to 100% serum free DCCM1 (+L-Glu, PNS). The DCCM1 media

TABLE 4

| Primer name | Sequence 5' to 3' | Notes |
|---|---|---|
| IgH-Apadel-NheI-For | tcctcaGCTAGCaccaagggAccatcggtcttcccctg<br>NheI<br>SEQ ID NO: 60 | Forward primer for removal of ApaI restriction site at IgH constant domain by silent mutation |
| IgH-BsrGI-Rev | gcagggTGTACActgtggttc<br>BsrGI<br>SEQ ID NO: 61 | Reverse primer for IgH-ApadeI-NheI-For |
| pCMV-KpnI-For | actgaaccttggagtcaGGTACCacattgat<br>KpnI<br>Tattgagtagttattaatag<br>SEQ ID NO: 62 | Forward primer for amplification of CMV promoter |
| pCMV-Rev | GGGCCCctgtggagagaaaggcaaagtggatg<br>ApaI<br>SEQ ID NO: 63 | Reverse primer for amplification of CMV promoter and insertion of ApaI restriction site between ER secretion signal and VL antibody region. |
| T427L-For | ctttgcctttctctccacagGGGCCCactccgac<br>ApaI<br>attgtgctgacccaatc<br>SEQ ID NO: 64 | Forward primer for amplification of T427 IgL and assembly with pCMV fragment. |
| T427L-Rev | cggtttaaaaaacgggacctctggaGCGGCCGCtt<br>NotI<br>attaacactctcccctgttgaagctctttgtg<br>SEQ ID NO: 65 | Reverse primer for amplification of T427 IgL that allows the replacement of XbaI by NotI restriction site. |
| BGH-polyA-For | tccagaggtcccgttttttaaaccggttttttaaaccgctg<br>atcagcctcg<br>SEQ ID NO: 66 | Forward primer for amplification of polyadenylation site and assembly with T427 IgL fragment. |
| BGH-polyA-EcoRI-Rev | tagctcgatccgtcgagaGAATTCccccagcat<br>EcoRI<br>gcctgctattg<br>SEQ ID NO: 67 | Reverse primer for amplification of polyadenylation site. |

Transfection of HEK293 T-REx™ Cells:

The calcium-phosphate transfection method was applied for introducing 1 μg of the pDual or pMAZ plasmids into T-REx 293 cells, seeded 3×10$^5$ cells/well on 6-well plate 24 hours before transfection. For transient transfection, the medium samples were collected 24, 48 and 72 hours post transfection. In order to obtain the stable transfectants, the from cells were collected every 2-4 days and gently changed to new serum-free media. It was possible to collect up to 4 harvests from the flask.

Protein A Purification of IgG Produced in Mammalian Cells:

The collected DCCM1 medium from antibody secreting cells was centrifuged at 5500 rpm for 15 minutes and filtered using 0.45 µm filtrap. The medium was diluted 1:20 with ×20 concentration phosphate buffer (400 mM) to final concentration of 20 mM $Na_2HPO_4$ and 20 mM $NaH_2PO_4$ and the mixture was loaded onto protein A column at a flow rate of 1 ml/min. The proteins were eluted with 0.1 mM citric acid (pH 3), neutralized with 1M Tris (HCl) pH 8.5 which was followed by dialysis against 20 mM phosphate buffer solution (PBS) pH 7.4. The protein final concentration was determined by absorbance at 280 nm.

ELISA Analysis:

The antigen binding by mono- and bispecific IgGs was determined as follows: 96-well ELISA plates were coated with 5 µg/ml of pure antigen in PBS 100 µl/well for overnight at 4° C. and blocked with 3% milk (in PBS) for 1 hr at 37° C. All subsequent steps were carried out at room temperature (25° C.). Protein-A purified proteins (or conditioned media) were applied onto the plates in a three-fold dilution series in PBST for 1 hour incubation and washed with PBST for three times. Following the 1 hour incubation with HRP-conjugated secondary antibody (1:5000 dilution in PBST, 100 µl/well), the plates were washed in PBST and developed using chromogenic HRP substrate TMB and colour development was terminated with 1 M $H_2SO_4$. The plates were read at 450 nm.

Cell ELISA Analysis:

The A431/CD30 (expressing CD30, target antigen for T427) and SKBR3 (expressing ErbB2, target antigen for FRP5) cell lines were maintained in DMEM supplemented by 10% fetal calf serum, 1% L-glutamine and 1% penicillin-streptomycin and grown at 37° C. with 5% $CO_2$. The cells ($2×10^4$/well) were seeded onto 96-well tissue culture plates in 100 µl medium and grown at 37° C. for overnight. Following the overnight growth the medium was gently poured out and the cells were fixed with 3% glutaraldehyde solution in water for 15 minutes at room temperature. The cells were washed with PBS and blocked with 5% BSA in PBS for 2 hours at 37° C. All subsequent steps were carried out according the regular ELISA protocol at room temperature (25° C.).

Dot Blot Analysis:

The 100 µl samples of 72 hours post-transfection cell conditioned media were diluted in an equal volume of PBS and applied via a vacuum manifold onto a nitrocellulose membrane filter using a dot-blot apparatus (Schleicher and Schuell, USA). After blocking the membranes with 3% (v/v) non-fat milk in PBS for 1 hour at 37° C., the membrane was washed briefly with PBS followed by incubation with goat-anti-human HRP conjugated secondary antibody for 1 hour at room temperature. After three washes with PBS the membrane was developed with the ECL reagent (Pierce, USA).

SDS-Page Analysis:

Polyacrylamide gel electrophoresis of proteins was performed according to Laemmli (Laemmli, 1970) 1/5 volume of 5× sample buffer was added to the protein samples followed by boiling for 5 minutes prior to loading onto the gel. 7.5%, 10% and 12% mini-gels were run at 120 V. For evaluation of full length IgG, non-reduced samples (without β-mercaptoethanol) were loaded, while the reduced protein samples separated into heavy and light chains components. Gels were stained with Coomassie blue solution (0.05% Coomassie R-250, 20% ethanol, 10% glacial acetic acid) for 2 hours and washed in destain solution (20% ethanol, 10% glacial acetic acid) until protein bands could be clearly seen. The protein band density was analyzed by ImageMaster 1D scanning laser densitometer (Pharmacia, Sweden). Gels that were stained were loaded with 20 µg of protein per lane for non-purified fraction or 3-5 µg for purified proteins. Gels that were further processed by immunoblotting were loaded with 1/10 that quantity.

Western Blot Analysis:

Proteins resolved by SDS-PAGE were electro-transferred onto the nitrocellulose membrane according to (Towbin et al., 1992). The membrane was blocked for at least 1 hour with PBS containing 5% non-fat milk powder at room temperature with slow agitation. The membrane was washed with PBS followed by incubation HRP conjugated goat-anti-human secondary antibodies (Jackson Laboratories, West Grove, Pa.). After three washes with PBS containing 0.05% Tween-20 (PBST) and one wash with PBS the nitrocellulose filter was developed with the SuperSignal West Pico Chemiluminescent Substrate (Thermo Scientific, USA) as described by the vendor.

Example 5

The Production of IgG in Mammalian Cells

The vector system used for the production of IgG in mammalian cells for production of bispecific antibodies was based on pMAZ vectors for production of monoclonal antibodies in mammalian cell culture (Mazor Y et al, 2007). Vector pMAZ-IgH was designed for human γ1 heavy chain expression and pMAZ-IgL for human κ light chain expression. The variable domains of light and heavy chains were introduced to the appropriate vector, co-transfected into HEK293 cells and stable antibody secreting clones were identified and kept. The starvation of cell clones to serum resulted in secretion of the desired antibody at a total yield of up to 20 mg per liter of culture.

Example 6

The Construction of Dual Vector for Production of IgG Molecules in Mammalian Cells The pDual vector was constructed by fusion of DNA fragments derived from the pMAZ-IgL and pMAZ-IgH vectors (Mazor Y et al, 2007) that were previously used for production of antibodies' light and heavy chains independently (FIG. 14), in order to build chimeric construct for production of light and heavy antibody chains using the same vector. The IgL and IgH were constructed in pDual vector as separate cassettes under the control of separate CMV promoters. The replacement of BssHI by ApaI restriction site in the light chain cassette simplified the following cloning of variable light and heavy domains into dual vector: ApaI-BsiWI were used for cloning of VL and BssHI-NheI were used for cloning of VH.

Example 7

The Construction of Bispecific Vectors for Transfection to Mammalian Cells

In order to construct the pDual-based vectors for production of bispecific molecules, the "knob", "hole" and "Cys" related mutations were cloned from the pHAK vectors into the pDual system. The cloning process resulted in the series of constructs listed in Table 5. The replacement of Neo® with Hygro resistance cassette in pDual-T427 vectors was carried out by subcloning of the cassette from pMAZ-IgL vector using AvrII and KpnI restriction enzymes. The resulted pDual-Neo® and pDual-Hygro® vectors' pair can be used for transfection in mammalian cells and selection of stable clones that produce 4 different antibody chains: two heavy and two light chains within one cell line.

TABLE 5

| Vector name | Product |
| --- | --- |
| pDual-T427 wt Neo$^R$ | IgL-T427 + IgH-T427 |
| pDual-FRP5 wt Neo$^R$ | IgL-FRP5 + IgH-FRP5 |
| pDual-T427-L(wt)-H(knob) Neo$^R$ | IgL-T427 + IgH-T427(knob) |
| pDual-FRP5-L(wt)-H(hole) Neo$^R$ | IgL-FRP5 + IgH-FRP5(hole) |
| pDual-T427-L(Cys)-H(wt) Neo$^R$ | IgL-T427(Cys) + IgH-T427 |
| pDual-T427-L(Cys)-H(knob) Neo$^R$ | IgL-T427(Cys) + IgH-T427(knob) |
| pDual-T427-L(wt)-H(Cys-knob) Neo$^R$ | IgL-T427 + IgH-T427(Cys-knob) |
| pDual-T427-L(Cys)-H(Cys-knob) Neo$^R$ | IgL-T427(Cys) + IgH-T427(Cys-knob) |
| pDual-T427 wt Hygro$^R$ | IgL-T427 + IgH-T427 |
| pDual-T427-L(Cys)-H(Cys-knob) Hygro$^R$ | IgL-T427(Cys) + IgH-T427(Cys-knob) |

Example 8

The Production and Evaluation of Bispecific IgG Molecules in Transient Transfected HEK293 T-REx™ Cells The following example demonstrates the importance of the S—S bridge between the light and heavy chain of the antibody in IgG secretion system and proves that the "alternative Cysteine" theory for coupling the appropriate light and heavy chain of bispecific antibody is relevant in mammalian production system as well as it had been demonstrated in the E. coli produced bispecific "Inclonals". The HEK293 T-REx™ cell line was used for this study. The cells were transiently transfected with either pDual-T427 wt (encoding wt IgG), pDual-T427-L(Cys)-H(wt) (encoding wt heavy chain and light chain that lacks the C-kappa cysteine and does contain the e engineered cysteine in VL, this should be a pair of chains that should not form an IgG) or with pMAZ-IgL+pMAZ-IgH (previous system for wt IgG production) pair as control. The evaluation of post-transfection medium by Western blot analysis showed that no full-size antibodies were detected in media of pDual-T427-L(Cys)-H(wt) transfected cells, while the transfection of pDual wt construct produced the detectable levels of the secreted antibody (up to 1 µg/ml in comparison to Erbitux dilutions) (FIGS. 15A and B).

The secretion of bispecific IgG molecules was also demonstrated and the preference of bispecific IgG formation using "knobs-into-holes" and "alternative Cysteine" (also called "disulfide stabilization") approaches was also estimated. The pDual vectors were transiently transfected to HEK293 TRex cells and the secreted antibodies were detected by Western blot analysis of conditioned media. The cells that were transfected with four pMAZ vectors (pMAZ-T427-IgL, pMAZ-T427-IgH, pMAZ-FRP5-IgL and pMAZ-FRP5-IgH) served as a control. The analysis of experiment demonstrated: 1) the "knobs-into-holes" approach is a solution for efficient heterodimerization of different heavy chains, 2) "alternative Cys" approach provide the solution for coupling of light and heavy chains of the same antibody arm, 3) the combination of the two above approaches provides the secretion of full-length bispecific IgG antibodies in mammalian cells production systems. As shown in FIG. 16, when "wrong" combinations of chains are used, no full size IgG can be seen in the immunoblot analysis of conditioned media. Intact IgG can be observed in cells that express monospecific IgG (lanes 1 and 2), in cells that express two monospecific IgGs (lanes 5, two pDual vectors and lane 4 four pMAZ vectors) and in cells that express a bispecific IgG (lane 7).

Example 9

The Production and Evaluation Bispecific IgG Molecules in Stable Transfected HEK293 T-REx™ Cells and Evaluation of Antigen Binding In order to obtain stable antibody-secreting clones, the present inventors co-transfected HEK293 T-REx™ cells with pDual-FRP5-L(wt)-H(hole) Neo® and pDual-T427-L(Cys)-H(Cys-knob) Hygro® vectors. The resultant Neo+ Hygro resistant clones were verified for their ability: 1) to secrete antibody, 2) to bind both antigens, 3) to secret full-length IgG for further purification. The preliminary antibody secretion test was performed using Dot blot analysis (the test example demonstrated in FIG. 17) and identified the low, medium and high secreting clones. The clones marked as medium and high secretors were examined for their antigen binding activity. ELISA was carried out to evaluate the binding level of each clone to erbB2 (FRP5) and CD30 (T427) recombinant antibodies (FIG. 18). The several clones that were able to bind each of the antigens continued to the third step and were purified on protein A affinity column (FIG. 19). The purified antibodies were analyzed to determine their size, purity and binding activity to either recombinant antigens or antigen-presenting cells (FIGS. 20 and 21). As shown in FIG. 18, the binding signal in ELISA correlated to the secretion level of these clones. As shown in FIGS. 20 and 21, a protein A-purified bispecific IgG bound to both CD30 and ErbB2 antigens. In such an ELISA (FIG. 21) it was expected that the monospecific IgGs (which are bi-valent) will show a more intense binding signal, each on its cognate antigen, due to avidity effect. A preliminary cell-ELISA (FIG. 22) shows that the bispecific antibody secreted by clone D3 stains antigen-positive cells.

Example 10

Construction of Monospecific Antibodies

First, a mono-specific antibody (T427 IgG) was generated that comprised the knobs into hole (KIH) mutation. In order to evaluate the binding activity of KIH T427 IgG molecules, ELISA was carried out. The ELISA plate was coated with MBP-CD30 and incubated with T427 KIH IgG (fused to PE38). It was demonstrated that the binding ability of T427 KIH molecule was similar to the binding of unmodified T427 IgG and T427-PE38 IgG-PE38 (FIG. 24).

Subsequently, a mono-specific antibody (T427 IgG) was generated that comprised both the KIH mutation and the cysteine mutations in the light chains as described herein above.

In order to produce the mono-specific T427 antibody, 4 chains were constructed: IgL-PE38, IgH-knob, IgH-Cys-hole and IgL-Cys. The presence of 38 kDa PE38 fused to VL-unmodified light chain provided the possibility to analyze the pairing of the appropriate heavy and light chains (analogous to KIH heterodimerization analysis) and the formation of the full-sized mono bi-specific molecule (Figure not shown).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A bispecific antibody comprising an Fc region and a Fab region, wherein:
said Fab region comprises a first covalent link between a first heavy chain and a first light chain of said Fab region and a second covalent link between a second heavy chain and a second light chain of said Fab region, wherein said first covalent link is a naturally occurring disulfide bond between a CH1 domain of said first heavy chain and a CL domain of said first light chain; and said second covalent link is a disulfide bond between an engineered cysteine of a $V_H$ domain of said second heavy chain and an engineered cysteine of a $V_L$ domain of said second light chain, wherein said second heavy chain is devoid of its native disulfide bond with said second light chain, wherein:
(i) said first heavy chain has a tryptophan at position 366 on a $C_{H3}$ domain which generates a protuberance;
(ii) said second heavy chain has a serine at position 366, an alanine at position 368 and a valine at position 407 on a $C_{H3}$ thereof wherein the $V_H$ domain of said second heavy chain further comprises a cysteine at position 44 and an alanine at position 222;
(iii) said first light chain is a native first light chain; and
(iv) said second light chain has a cysteine at position 100 of the $V_L$ domain and has a cysteine deletion at the position of its native disulfide bond with said second heavy chain, wherein the numbering of said position is according to Kabat and Wu.

2. The antibody of claim 1, being selected from the group consisting of a chimeric antibody, a humanized antibody and a fully human antibody.

3. The antibody of claim 1, wherein each light chain is linked to its cognate heavy chain via a single disulfide bond.

4. The antibody of claim 1 being an intact antibody.

5. The antibody of claim 1, wherein the antibody is selected from the group consisting of IgA, IgD, IgE and IgG.

6. The antibody of claim 5, wherein said IgG comprises IgG1, IgG2, IgG3 or IgG4.

7. The antibody of claim 1, wherein said first heavy chain comprises an S354C mutation and said second heavy chain comprises a Y349C mutation, wherein the numbering of the position of the mutation is according to Kabat and Wu.

8. The antibody of claim 1, wherein at least one of said heavy chains is attached to a therapeutic moiety.

9. The antibody of claim 1, wherein at least one of said heavy chains is attached to an identifiable moiety.

10. The antibody of claim 1, being selected from the group consisting of a primate antibody, a porcine antibody, a murine antibody, a bovine antibody, a goat antibody and an equine antibody.

11. The antibody of claim 1, wherein said native disulfide bond is between CH1 of said second heavy chain and CL of said second light chain.

* * * * *